United States Patent
Ito et al.

(10) Patent No.: US 8,475,940 B2
(45) Date of Patent: Jul. 2, 2013

(54) ANTHRACENE DERIVATIVE AND LIGHT-EMITTING DEVICE

(75) Inventors: Yuichi Ito, Tokyo (JP); Kazuhiko Tsuchiya, Tokyo (JP); Toshinobu Shinnai, Tokyo (JP); Junpei Takahashi, Tokyo (JP)

(73) Assignee: Toppan Printing Co., Ltd., Tokyo (JP)

(*) Notice: Subject to any disclaimer, the term of this patent is extended or adjusted under 35 U.S.C. 154(b) by 0 days.

(21) Appl. No.: 13/495,698

(22) Filed: Jun. 13, 2012

(65) Prior Publication Data

US 2012/0248973 A1  Oct. 4, 2012

Related U.S. Application Data

(63) Continuation of application No. PCT/JP2010/072235, filed on Dec. 10, 2010.

(30) Foreign Application Priority Data

Dec. 14, 2009  (JP) ................................. 2009-283206

(51) Int. Cl.
   C09K 11/06  (2006.01)
   C07D 403/10  (2006.01)
   H01L 51/50  (2006.01)

(52) U.S. Cl.
   USPC ........... 428/690; 428/917; 313/504; 313/506; 544/180; 252/301.16

(58) Field of Classification Search
   None
   See application file for complete search history.

(56) References Cited

U.S. PATENT DOCUMENTS

| | | | |
|---|---|---|---|
| 5,935,721 A | 8/1999 | Shi et al. | |
| 2007/0131929 A1* | 6/2007 | Bae et al. | 257/40 |
| 2008/0111473 A1* | 5/2008 | Kawamura et al. | 313/504 |

FOREIGN PATENT DOCUMENTS

| JP | 11-329732 | 11/1999 |
|---|---|---|
| JP | 2002-324401 | 11/2002 |

(Continued)

OTHER PUBLICATIONS

Translation for JP 2004-002297 (publication date Jan. 2004).*

(Continued)

*Primary Examiner* — Dawn Garrett

(57) ABSTRACT

According to the invention, there is provided a compound represented by a formula (1) below:

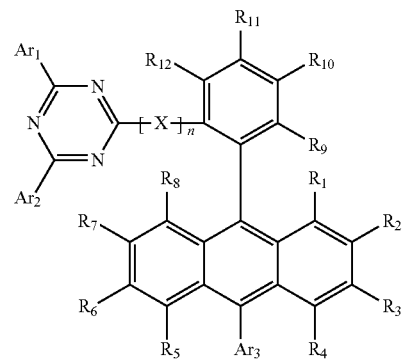

Formula (1)

wherein X represents a residue derived from an aryl ring or a heteroaryl ring, or a single bond, $Ar_1$ and $Ar_2$ respectively represent a phenyl group or heteroaryl group, $Ar_3$ represents a group having 60 or less carbon atoms, the group represents a structure in which six or less aryl or heteroaryl groups which may have one or more substituents are conjugatedly linked, or the same group as a substituent at the ninth or tenth position on the anthracene ring, and n represents an integer of 0 or 1.

9 Claims, 15 Drawing Sheets

FOREIGN PATENT DOCUMENTS

| | | | |
|---|---|---|---|
| JP | 2004-002297 | * | 1/2004 |
| JP | 3588978 | | 8/2004 |
| JP | 3769934 | | 2/2006 |
| JP | 2006-176448 | | 7/2006 |
| JP | 2007-80906 | | 3/2007 |
| JP | 2007-527361 | | 9/2007 |
| JP | 2008-124156 | | 5/2008 |
| JP | 2008-270557 | | 11/2008 |
| JP | 2009-33146 | | 2/2009 |
| JP | 2009-516652 | | 4/2009 |
| JP | 2009-246097 | | 10/2009 |
| KR | 10-2008-0037302 | | 4/2008 |
| KR | 10-2010-0007143 | | 1/2010 |
| WO | WO 2008/023628 | | 2/2008 |

OTHER PUBLICATIONS

Jianmin Shi et al., "Anthracene derivatives for stable blue-emitting organic electroluminescence devices", Applies Physics Letters, vol. 80, No. 17, Apr. 2002, pp. 3201-3203.

E. Kitazume et al., "41.2: Development of Polymer Light-Emitting Diode (PLED) Displays using the Relief Printing Method", SID 06 Digest, 2006, pp. 1467-1470.

William F. Feehery, "69.1 *Invited Paper*: Solution Processing of Small-Molecule OLEDs", SID 07 Digest, 2007, pp. 1834-1836.

M. Masuichi et al., "30.1: New Nozzle-printing Method for Large-Size Organic EL Device", SID 05 Digest, 2005, pp. 1192-1195.

Tadashi Gohda et al., "58.3: A 3.6-in. 202-ppi Full-Color AMPLED Display Fabricated by Ink-Jet Method", SID 06 Digest, 2006, pp. 1767-1770.

David Albertalli, "30.0: Gen 7 FPD Inkjet Equipment—Development Status", SID 05 Digest, 2005, pp. 1200-1203.

Tatsuya Shimoda, "39.1: *Invited Paper*. Ink-jet Technology for Fabrication Processes of Flat Panel Displays", SID 03 Digest, 2003, pp. 1178-1181.

Tatsuaki Funamoto et al., "27.5L: *Late-News Paper*. A 130-ppi, Full-Color Polymer OLED Display Fabricated Using an Ink-jet Process", SID 02 Digest, 2002, pp. 899-901.

Takashi Hirano et al., "53.2: *Distinguished Paper*. Novel Laser Transfer Technology for Manufacturing Large-Sized OLED Displays", SID 07 Digest, 2007, pp. 1592-1595.

Michael Boroson et al., "16.5L: *Late-News Paper*. Non-Contact OLED Color Patterning by Radiation-Induced Sublimation Transfer (RIST)", SID 05 Digest, 2005, pp. 972-975.

Kyung-Jin Yoo et al., "38.2: 302-ppi High-Resolution AMOLED using Laser-Induced Thermal Imaging", SID 05 Digest, 2005, pp. 1344-1347.

Hiroshi Kimura et al., "22.3: New Full Color OLEDs Technology based on Advanced Color Conversion Method using Ink-Jet Printing", SID 08 Digest, 2008, pp. 299-302.

Devin MacKenzie et al., "4.3: Printed, Doped Flexible P-OLED Displays and Lighting", SID 09 Digest, 2009, pp. 20-24.

S. Enomoto et al., "Liquid Light-Emitting Display based on Electrochemiluminescence with Interdigitated Microelectrodes", IDW 06 Preprints, 2006, pp. 1331-1333.

Kazuki Nishimura et al., "Solution Electrochemiluminescent Cell with a High Luminance Using an Ion Conductive Assistant Dopant to Improve Transportation of Carrier", The Institute of Electronics, Information and Communication Engineers Transactions, vol. J85-C, No. 12, Dec. 2002, pp. 1108-1112.

Yuichi Ito, M&BE, vol. 11, No. 1, 2000, pp. 32-41.

International Search Report of Corresponding PCT Application PCT/JP2010/072235 mailed Feb. 15, 2011.

Molecular Tectonics. Porous Hydrogen-Bonded Networks Built from Derivatives of 2,2'7,7'-Tetraphenyl-9,9'-spirobi[9*H*-fluorenet] Eric Demers et al., Department de Chimie, Universite de Montreal, 2005, Crystal Growth & Design vol. 5, No. 3.

* cited by examiner

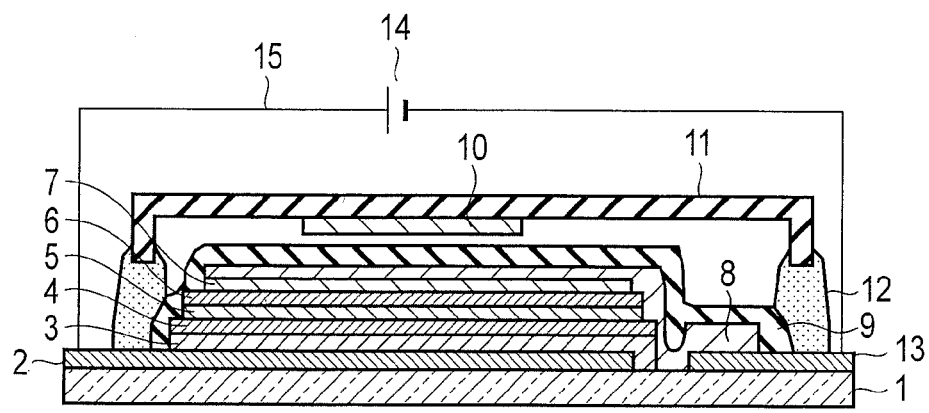
F I G. 1
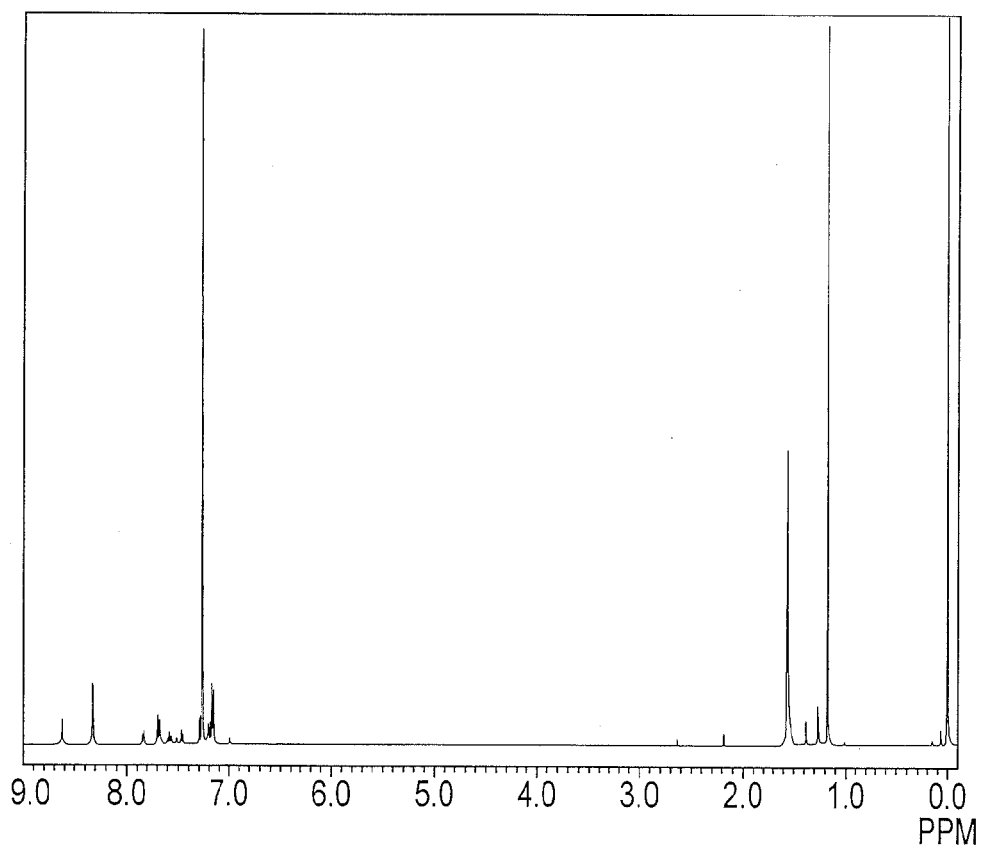
F I G. 2A

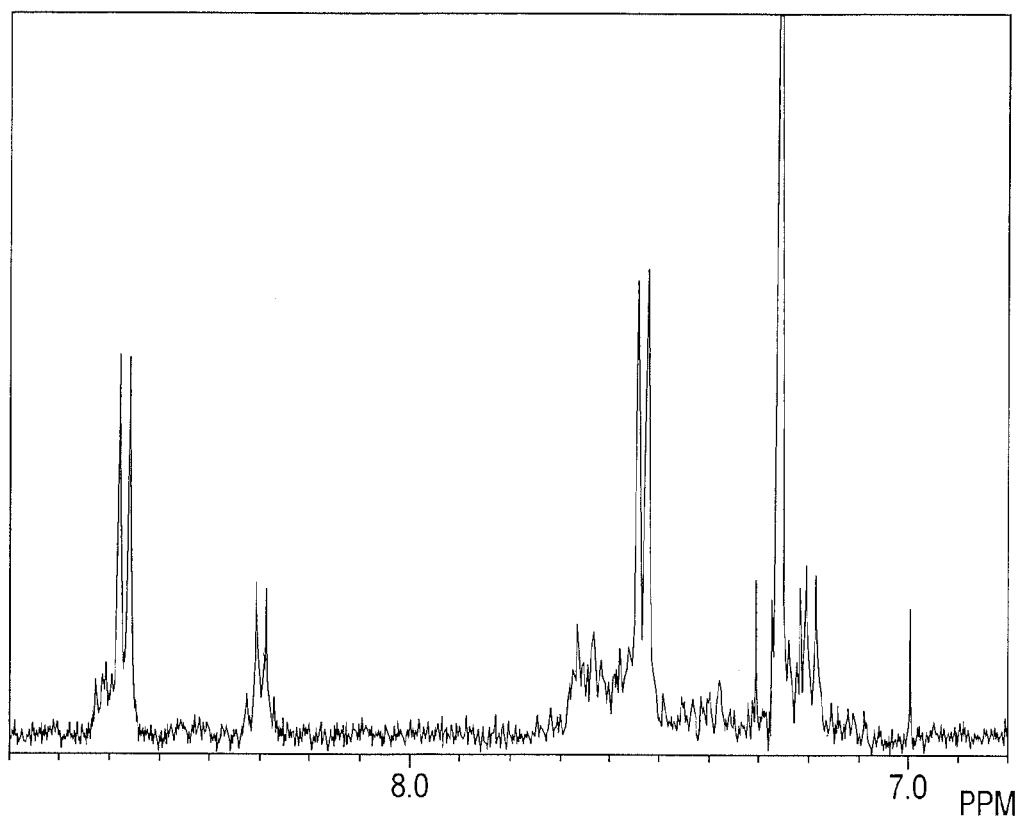
F I G. 5B

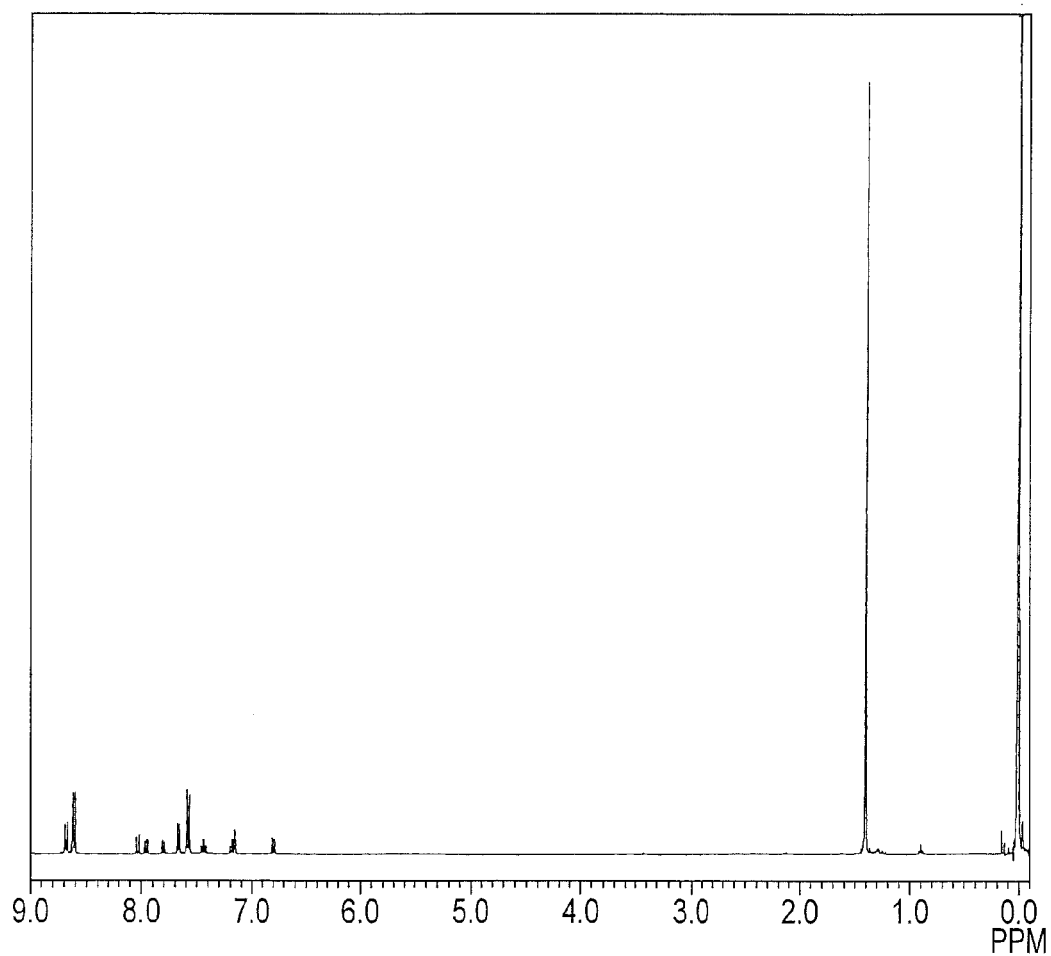
F I G. 7A

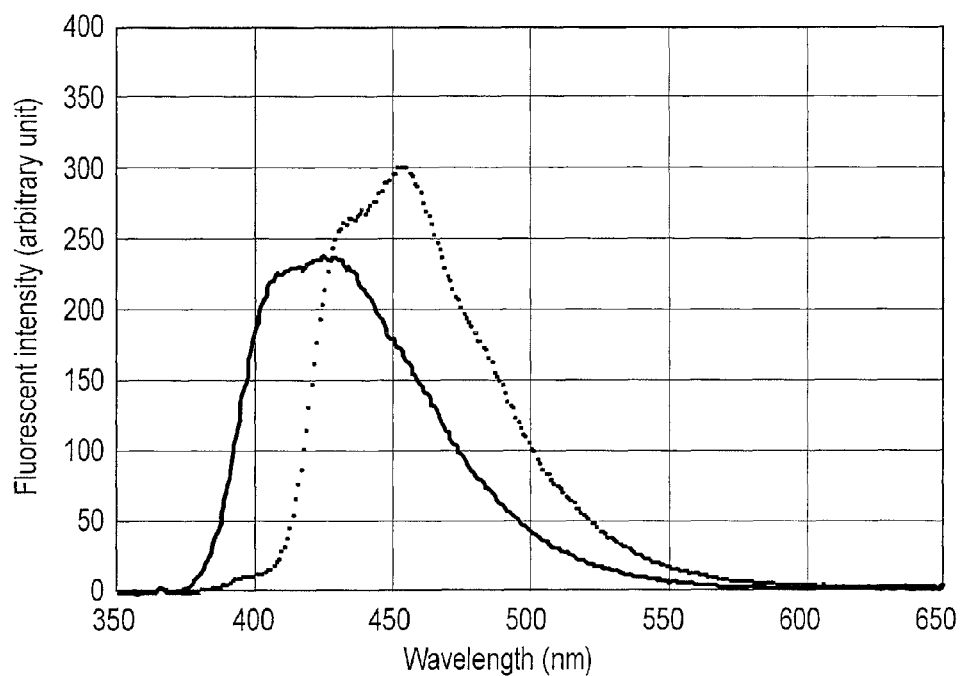
F I G. 10
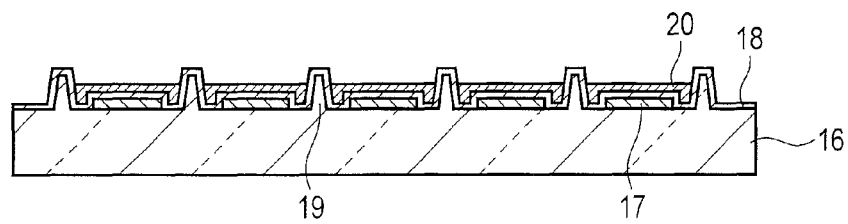
F I G. 11

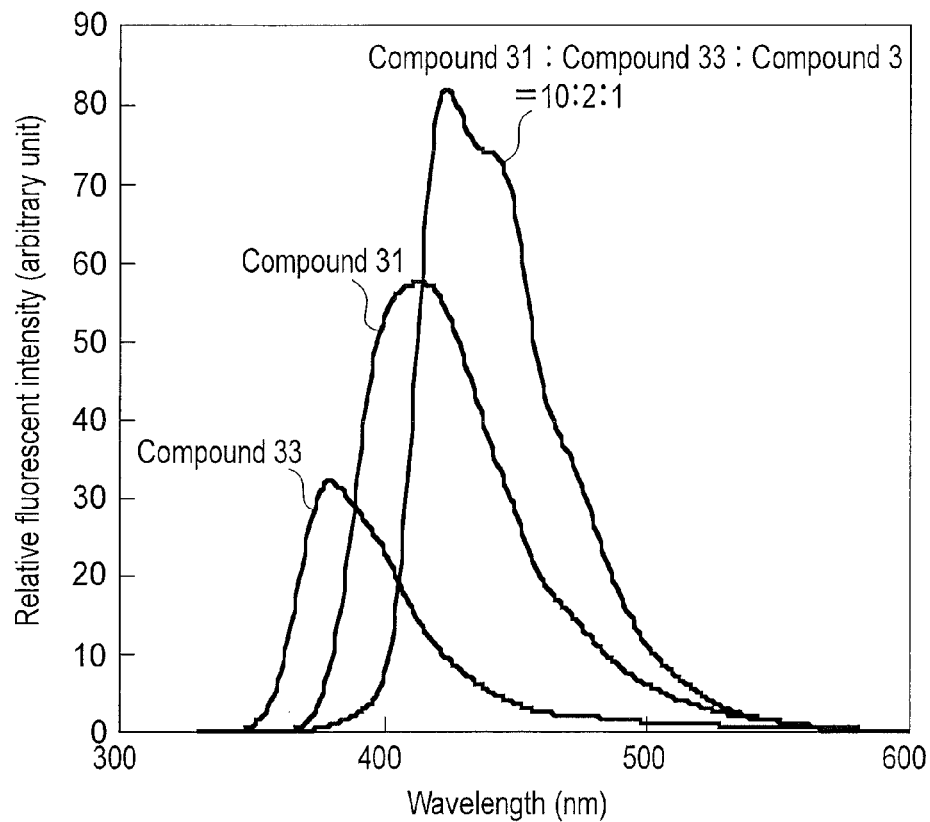
F I G. 12
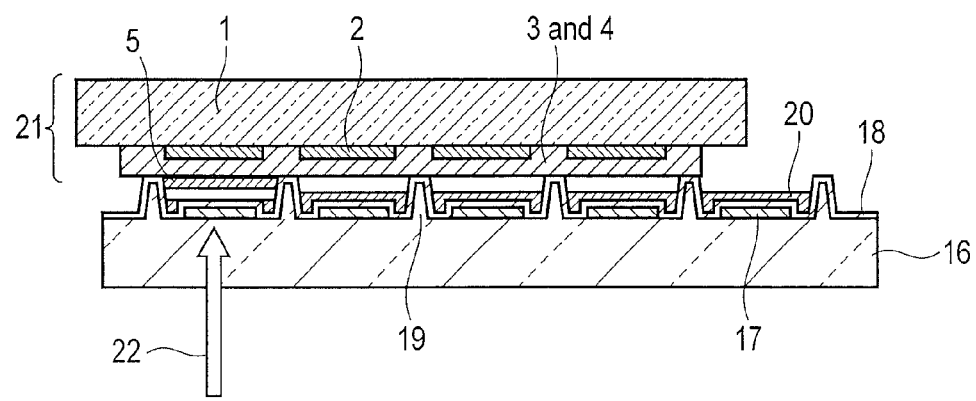
F I G. 13

ANTHRACENE DERIVATIVE AND LIGHT-EMITTING DEVICE

CROSS REFERENCE TO RELATED APPLICATIONS

This application is a Continuation Application of PCT Application No. PCT/JP2010/072235, filed Dec. 10, 2010 and based upon and claiming the benefit of priority from prior Japanese Patent Application No. 2009-283206, filed Dec. 14, 2009, the entire contents of which are incorporated herein by reference.

BACKGROUND OF THE INVENTION

1. Field of the Invention

The present invention relates generally to an anthracene derivative which can be used as a fluorescent material, light-emitting material, host material, carrier transport material or carrier injection material for holes or electrons used in an organic electroluminescent (hereinafter abbreviated as "organic EL") device and display, and to an organic electroluminescent device using these materials.

2. Description of the Related Art

Organic electroluminescent devices are those which are provided with a solid or liquid light-emitting layer containing a fluorescent or phosphorescent organic luminescent material as one layer between electrodes facing each other and emit light by applying a voltage across the electrodes. Generally, a device containing a solid organic light-emitting layer is called an organic electroluminescent device and a device containing a liquid light-emitting layer is called an organic electroluminescent device or an organic electrochemical luminescent device. Broadly speaking, a device constituted of an organic light-emitting material that emits light by electric energy is an organic electroluminescent device, and such organic electroluminescent devices can include the device containing a liquid light-emitting layer.

Generally, an organic electroluminescent device having a solid light-emitting layer is provided with at least a light-emitting layer between a positive electrode and negative electrode which comprises a low-molecular-weight or polymer organic material that emits fluorescence or phosphorescence with high luminous efficiency.

The Light-emitting layer is generally sandwiched between a hole transport layer and an electron transport layer and further sandwiched between the positive electrode and negative electrode.

As the positive electrode, a transparent conductive film such as indium-tin complex oxide (hereinafter abbreviated as "ITO") and indium-zinc complex oxide (hereinafter abbreviated as "IZO") having a large ionization potential (hereinafter abbreviated as "Ip") is used to reduce the energy barrier to inject holes into the organic light-emitting layer. There is the case where an oxide of tungsten, vanadium, molybdenum, ruthenium, titanium etc. are disposed on the surface of the positive electrode or blended in a material of the transparent conductive film to obtain a larger Ip.

As the negative electrode, a metal layer containing an alkali metal, alkali earth metal, or rare earth elements which have a low ionization potential and hence have a low electron injection barrier is used. However, they have the problem that it is necessary to sealed strictly because they are easily corroded by water.

General organic electroluminescent device has rectification characteristics and when a direct voltage is applied to this organic electroluminescent device, holes and electrons are transported from the positive electrode and negative electrode to the light-emitting layer through the hole transport layer and electron transfer layer, respectively, then, these holes and electrons are recombined with each other in the light-emitting layer to emit light. The organic electroluminescent device emits light when a forward bias is applied in the case of alternating voltage drive.

The luminous efficacy of an organic electroluminescent device is improved by keeping a carrier balance between holes and electrons to be injected. Further, it is effective to prevent carriers from being accumulated at the interface and inside of the organic layer for inhibition of deterioration and extension of life of the organic layer. In light of this, the film thickness and carrier transport ability of each layer and energy barrier of interlayer are regulated to manufacture organic electroluminescent device having a high efficiency and long-life.

As to the light-emitting mechanism of an organic electroluminescent device using a solution as the light-emitting layer, radical anions of a light-emitting material which are generated by the injection of electrons from the negative electrode and radical cations of a light-emitting material which are generated by the deprivation of electrons by the positive electrode were diffused in a solution and collided with each other, causing the light-emitting material to enter into an excited state to emit light. Although a luminance of hundreds to thousands of candelas ($cd/m^2$) is obtained, the organic electroluminescent device has a problem concerning a too retarded response speed for use as a display, due to ionic diffusion-based conductance.

Hamada et al. dissolved about 0.5 wt % of a fluorescent compound having condensed aromatic rings such as rubrene in a mixed organic solvent of orthodichlorobenzene and toluene and added 1,2-diphenoxyethane as a positive ion conductive assist dopant to obtain a luminance of 100 $cd/m^2$ at 80 V (Patent reference 1 and Non-patent reference 1).

Enomoto et al. dissolved rubrene and tetra-n-butylammoniumhexafluorophosphate as a supporting electrolyte in a mixed solvent of orthodichlorobenzene and acetonitrile (3:1) and applied alternating voltage drive under the condition of 30 Hz and ±1.9 V by using a comb-shaped electrode having a width of 8 μm and a gap of 4 μm, with the result that the positive electrode and the negative electrode are switched therebetween in the same electrode, so that both anionic and cationic radicals are generated around the electrode and recombined, which provides light emission with high efficiency and a luminance of 220 $cd/m^2$ at a response speed of 3 ms (Non-patent reference 2).

Although organic electroluminescent devices of electrochemiluminescence type have an advantage that a stable metal can be used as the electrode material, they have the problem that they each have a shorter life than all-solid type organic electroluminescent devices due to the influence of oxygen, water and impurities in the solution and side reaction with the supporting electrolyte. However, these organic electroluminescent devices have been improved, for example, by using sparingly volatile ionic liquids as the mediums, by using a solid electrolyte to prevent deterioration, or by using a porous electrode to increase the surface area of the electrode, thereby developing electroluminescent devices having high luminance. As the light-emitting materials, phosphorescent materials besides low-molecular-weight fluorescent materials and polymer materials may be used and studies have been continued as to developments of the organic electroluminescent devices which have long life, high luminance and high efficiency. Recently, Add-vision Inc. have reported that an organic electroluminescent device which generate white color light of initial luminance of 100 $cd/m^2$ and a long life exceeding 6000 hr (half-life) (Non-patent reference 3).

Hereinafter, a general organic electroluminescent device using a solid light-emitting layer will be explained in more detail.

Typically, an organic electroluminescent device has a structure in which layers such as a hole injection layer, an electron-block hole transport layer, a light-emitting layer, a hole-block electron transport layer, an electron transport layer, an electron injection layer, and a negative electrode are formed in this order on a transparent positive electrode formed on a transparent substrate such as glass and hermetically sealed.

Red, blue, or green light emission can be obtained easily by changing the molecular structure of the organic material contained in the light-emitting layer.

A method for obtaining white light emission includes, for example, a method in which a bluish green light-emitting material is doped with a yellowish orange light-emitting material to obtain a wide range spectrum, a method in which two light-emitting layers consisting of bluish green and yellow layers are stacked, a method in which structural units of red, green and blue light-emitting layers are stacked through a carrier-generating layer, and a method in which using an excimer light-emitting material, a bluish green monomer light emission is overlapped on a yellow to red color excimer light emission spectrum.

Examples of a system used to develop a color display of an organic electroluminescent device include a method in which red, blue, and green colors are separately applied to each pixel, a method in which a red, blue, green, or white color filter is superposed on a white light-emitting device to obtain spectral colors, and a method in which a film of, for example, a polymer electroluminescent material is formed on a blue or ultraviolet light-emitting device to obtain green or red color emission as a fluorescent conversion film (Non-patent reference 4).

As a method of forming the light-emitting layer, various methods have been developed. Though a film of a low-molecular-weight material is generally formed by vacuum deposition, the coating or printing method which is usually carried out for polymer materials may be applied to materials which are highly soluble and have a wet film-forming ability.

As a method of selective vapor deposition of pixels in different colors when using a low-molecular-weight material, a mask deposition method is generally used.

However, the mask deposition method has the problem concerning alignment accuracy between the mask and the substrate when larger size of substrate is used. The problem is due to the influences of difference in the thermal expansion between mask and the glass, application error of the mask to the frame, or deflection of the substrate and mask due to gravitation.

In light of this, laser transfer methods including a laser thermal transfer method and laser sublimation transfer method are attempted to improve alignment accuracy.

The laser thermal transfer method includes a LITI (Laser Induced Thermal Imaging) method (Non-patent reference 5) performed in 3M and Samsung. The laser sublimation transfer method includes a RIST (Radiation Induced Sublimation Transfer) method (Non-patent reference 6) method performed in Eastman Kodak and a LIPS (Laser Induced Pattern wise Sublimation) method (Non-patent reference 7) method performed in Sony.

In the LITI method, a donor film formed by depositing or applying a transfer material made of a low-molecular weight or polymer electroluminescent material is brought into close contact with the display substrate and irradiated with a laser according to a predetermined pixel in each color to perform thermal transfer. A 302 ppi highly precise display of 2.65 inches and a display of 17 inches have been produced experimentally. However, these displays pose the problem that a film having high film strength formed by a polymer electroluminescent material has deterioration in film cutting properties and generates burrs easily when peeling the donor film, and therefore, a low-molecular weight material which is soluble and has good wet film formation characteristics is also added.

In the RIST method, a film of a low-molecular-weight organic electroluminescent material is formed on a donor film by the vapor deposition method. After the formed film surface of the donor film and the display substrate are made to face each other at a small distance in vacuo, a laser is applied to a pixel having a target color from the backside of the donor film to deposit the pixel onto the display substrate by sublimation or vaporization.

In the LIPS method, a highly precise organic electroluminescent display of 27 inches is manufactured experimentally by using a transfer substrate made of glass having high registration characteristics in place of the donor film. However, it entails a high cost to form a film on a donor film or substrate by vapor deposition. A material which has a low molecular weight and can be formed by application is desired to reduce costs.

In the case of a low-molecular weight material or polymer material which is soluble in a solvent and can be formed in a wet system, highly precise selective vapor deposition of pixels in different colors can be accomplished by, for example, the inkjet method (Non-patent references 8 to 11), continuous nozzle printing method (Non-patent references 12 and 13), or relief printing method (Non-patent reference 14).

The inkjet method is a method enabling selective vapor deposition in an inexpensive apparatus even if the substrate is increased in size, and a polymer electroluminescent material is generally used in this method.

As a polymer blue light-emitting material, for example, copolymer consisted of fluorenone or phenoxazine and polyphenylene type copolymers, which each have an energy difference between ionization potential and electronic affinity (hereinafter abbreviated as Eg) larger than about 3 eV or more are used as the base. Green or red light-emitting polymer materials are synthesized by copolymerizing a blue light-emitting material as the base with a monomer which can emit green or red light and has a small Eg. A low-molecular weight type phosphorescent material having high luminous efficiency is added or introduced into the side chain of these light-emitting compounds.

Polymer materials tend to generate excimer emission light having a long wavelength by heating during the process of manufacturing a device or the operation of the device and it is particularly necessary to take care in molecular design to limit reduction in the color purity of EL light emission. Further, polymer materials cannot be refined by sublimation and are therefore highly purified with difficulty. Because the molecular weight is changed by the influence of water or impurities in the monomer, the polymer material has the problem concerning, for example, difficulty in the stability quality depending on the lot.

As a low-molecular weight blue light-emitting material, Ito (Toppan Printing Co., Ltd.) (Patent reference 2) and Jianmin Shi and Ching W. Tang etc., (Kodak) (Non-patent reference 15) developed unbipolar 9,10-di(2-naphthyl)-anthracene derivatives containing anthracene as a skeleton. These derivatives were used as blue light-emitting layer host materials for displays of, for example, MP3 players, personal multiplayers, and digital cameras.

9,10-di(2-naphthyl)-2-tertiarybutylanthracene (hereinafter abbreviated as "TBDNA") which is a typical material of these derivatives has a glass transition temperature (hereinafter abbreviated as "Tg") of about 128° C. when measured by differential scanning calorimeter (hereinafter abbreviated as DSC). Further, this material is crystallized at 222° C. or more and melts at 285° C. This leads to the case where the inside of the device is heated to Tg or more, causing mixing or crystallization of the organic layer, which develops short circuits when light with high luminance is emitted at a high current density. Therefore, a higher Tg and improvement in amorphous characteristics are desired.

Further, TBDNA can be formed in a wet system by the spin coating method using toluene. However, TBDNA has a molecular weight as low as 486 and therefore, the formed film is gradually sublimated even in vacuum drying at a temperature as relatively low as about 130° C., giving rise to a problem concerning insufficient heat resistance.

When the film is doped with 2,5,8,11-tetra-t-butylperylene for improving luminance, the EL light emission peak is shifted to the longer wavelength side, that is, from 460 nm to 465 nm, posing the problem in television use for which high color purity is required.

With regard to the drive system of an EL display, when a small and less precise display having a low display capacity is used, a passive matrix drive system is used as the driving system and the structure is changed to a bottom emission type in which light is extracted from the transparent substrate side to cope with this situation. However, a large current flows in the passive matrix drive system when each pixel dot emits light in the case of a display having a large display capacity such as a highly precise color television. For this, usual organic electroluminescent materials having Tg of about 100 to 150° C. are inferior in heat resistance, posing the problem that they fail to perform long time operation.

In light of this, the operation performed by an active matrix driving circuit using a thin film transistor driving circuit formed on a glass substrate or a CMOS driving circuit formed on a silicon wafer has come to be used to drive each pixel dot at as low a current density as possible.

Moreover, a top emission system is adopted in which an organic electroluminescent device is formed on an insulation film formed on a driving circuit and a light transmitting counter electrode is formed on the side opposite to the substrate to extract light, thereby enabling increase in ratio of aperture, and further enabling low-current density drive. Further, the top emission system enables strong extraction of light having a specific wavelength of an EL light emission spectrum by utilizing a micro-interference (microcavity) effect produced between the transparent positive electrode side reflection film and semitransparent negative electrode with an organic EL medium layer being sandwiched therebetween. Moreover, color filters may be laminated to thereby more improve color purity (Patent reference 3). However, the top emission system has a problem as to high manufacture costs.

The color purity can also be improved by developing a light-emitting host material and light-emitting dopant material which each emit light having a shorter wavelength through molecular design. Ito et al. synthesized, for example, 9,10-di(biphenyl-2-yl)-2-t-butylanthracene (hereinafter abbreviated as "TBBPA") having an emission peak of about 420 nm and 450 nm (Patent reference 4). A CIE 1931 xy chromaticity coordinate of an electroluminescent device using TBDNA as a light-emitting layer was (0.172, 0.183). A device using TBBPA was so improved that the xy chromaticity becomes (0.157, 0.128). However, the glass transition temperature of TBBPA is as low as about 74° C., posing the problem concerning the necessity of improvement in the heat resistance of TBBPA.

Further, in the molecular design of a diamine type low-molecular weight hole transport material, a material having high amorphous characteristics and high solubility in an organic solvent can be obtained by introducing non-symmetry into a molecule (Non-patent reference 16). Similarly, a non-symmetrical structure is introduced into an anthracene type blue light-emitting material and there is also an attempt to develop a coating type electroluminescent device using a low-molecular weight material. However, many materials have a solubility of 2 wt % or less in toluene and the solubility of a material is in the order of about 5 wt % even if the material has higher solubility in toluene (Patent references 5 to 7). Further, the coating type electroluminescent device has a shorter life than the vapor deposition type.

Because of this, it is desired to develop a new lower-molecular weight light-emitting material having high color purity, high heat resistance, high solubility, high wet film forming characteristics, and high durability.

PRIOR ART REFERENCE

Patent Reference

Patent reference 1: Jpn. Pat. Appln. KOKAI Publication No. 2002-324401

Patent reference 2: Japanese Patent No. 3588978

Patent reference 3: Jpn. Pat. Appln. KOKAI Publication No. 2007-080906

Patent reference 4: Japanese Patent No. 3769934

Patent reference 5: Jpn. Pat. Appln. KOKAI Publication No. 2008-124156

Patent reference 6: Jpn. Pat. Appln. KOKAI Publication No. 2008-270557

Patent reference 7: Jpn. Pat. Appln. KOKAI Publication No. 2009-33146

Non-Patent reference

Non-patent reference 1: Nishimura, Hamada, Shibata, and Fuyuki, The Institute of Electronics, Information and Communication Engineers Transactions C, 1108 (2002).

Non-patent reference 2: S. Enomoto, Y. Mizuno, N. Saito, Y. Kizaki, I. Amemiya and S. Uchikoga, IDW' 06 Preprints, OLEDp-19, 1331 (2006).

Non-patent reference 3: Devin MacKenzie, Janie Breeden, Jianping Chen, Phil Hinkle, Eric Jones, Anoop Menon, Yuko Nakazawa, Joon-Ho Shin, Vung Vo, Matt Wilkinson, Yuka Yoshioka, and John Zhang, SID 09 DIGEST, 20 (2009).

Non-patent reference 4: Hiroshi Kimura, Koji Kawaguchi, Tetsuya Saito, Masaru Nagai, Tadashi Asakawa, Chong Li and Hiroshi Hashida, SID 08 DIGEST, 299 (2008).

Non-patent reference 5: H. YIN, SID 05 DIGEST, 38.2, p 1344.

Non-patent reference 6: M. Boroson, SID 05 DIGEST, 16.5L, p 972.

Non-patent reference 7: T. Hirano, SID 07 DIGEST, 53.2, p 1592.

Non-patent reference 8: T. FUNAMOTO, Y. Matsueda, 0. Yokoyama, A. Tsuda, H. Takeshita S. Miyashita, SID 02 DIGEST, 39.1 (2003).

Non-patent reference 9: T. Shimoda, SID 03 DIGEST, 39.1 (2003).

Non-patent reference 10: David Albertalli, SID 05 DIGEST, 30.3 (2005).

Non-patent reference 11: Tadashi Gohda, Yuhki Kobayashi, Kiyoshi Okano, Satoshi Inoue, Ken Okamoto, Satoshi Hashimoto, Emi Yamamoto, Haruyuki Morita, Seiichi, Mitsui and Mitsuhiri Koden, SID 06 DIGEST, 58.3 (2006).

Non-patent reference 12: M. Masuichi, M. Kawagoe, Y. Takamura, H. Adachi, Y. Fujimoto, and M. Ueno, SID05, DIGEST, 30.1 (2005).

Non-patent reference 13: W. F. Feehery, SID07 DIGEST, 69.1 (2007).

Non-patent reference 14: E. Kitazume, K. Takeshita, K. Murata, Y. Qian, Y. Abe, M. Yokoo, K. Oota, T. Taguchi, SID06DIGEST, 41.2 (2006).

Non-patent reference 15: Jianmin Shia and Ching W. Tang, Appl. Phy. Lett., 80(17), 3201 (2002).

Non-patent reference 16: Y. Ito, M & BE, vol 11, page 32 (2000).

BRIEF SUMMARY OF THE INVENTION

According to the first aspect of embodiments, there is provided a compound represented by a formula (1) below:

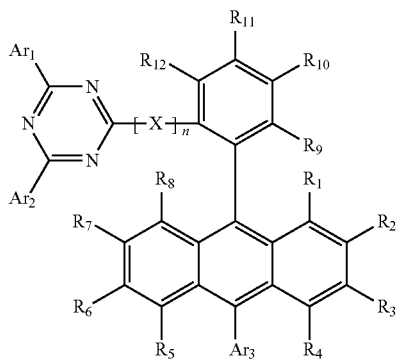

Formula (1)

wherein

X represents a residue derived from an aryl ring or a heteroaryl ring which may have one or more substituents, or a single bond, $Ar_1$ and $Ar_2$ respectively represent an unsubstituted or substituted phenyl group or heteroaryl group, $Ar_3$ represents a group having 60 or less carbon atoms, the group represents a structure in which six or less aryl or heteroaryl groups which may have one or more substituents are conjugatedly linked, or the same group as a substituent at the ninth or tenth position on the anthracene ring, the substituents on X and $Ar_1$ to $Ar_3$, and $R_1$ to $R_{12}$ are independently selected from a group consisting of hydrogen, deuterium, fluorine, a cyano group, a trifluoromethyl group, a trimethylsilyl group, an alkyl group, an alkoxy group and a polyoxyalkylene group having 15 or less carbon atoms, a substituted or unsubstituted aryl group and heteroaryl group having 15 or less carbon atoms, and a crosslinkable substituent having 15 or less carbon atoms, provided that $R_1$ to $R_{12}$ may have a structure in which adjacent substituents may be bonded to each other to thereby form a ring, and n represents an integer of 0 or 1.

According to the second aspect of embodiments, there is provided a compound represented by a formula (2) below:

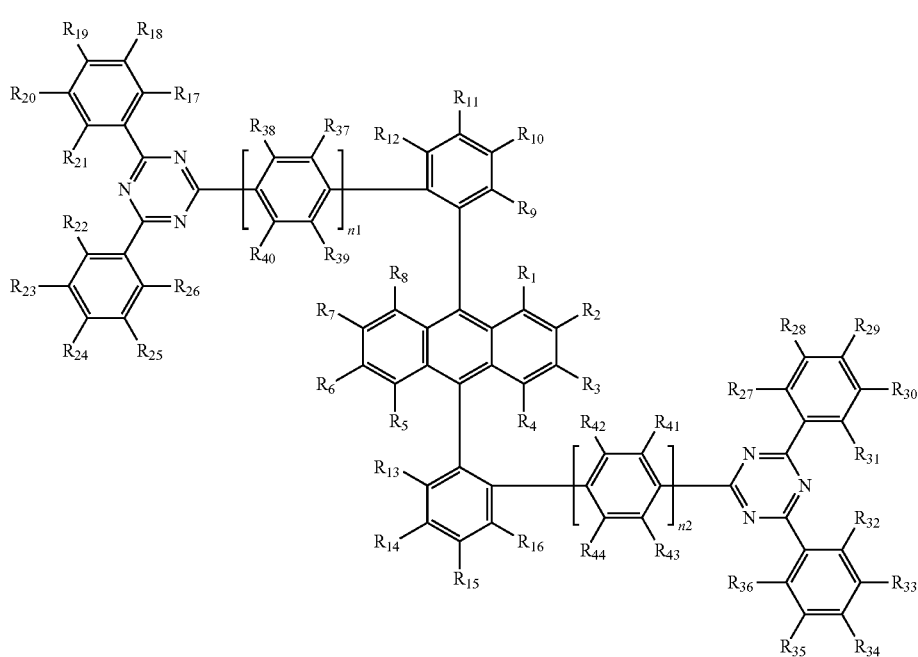

Formula (2)

wherein
each of $R_1$ to $R_{44}$ is independently selected from a group consisting of hydrogen, deuterium, fluorine, a cyano group, a trifluoromethyl group, a trimethylsilyl group, an alkyl group, an alkoxy group and a polyoxyalkylene group having 15 or less carbon atoms, a substituted or unsubstituted aryl group and heteroaryl group having 15 or less carbon atoms, and a crosslinkable substituent having 15 or less carbon atoms, and
each of n1 and n2 independently represents an integer of 0 or 1.

According to the third aspect of embodiments, there is provided a compound represented by a formula (8) below:

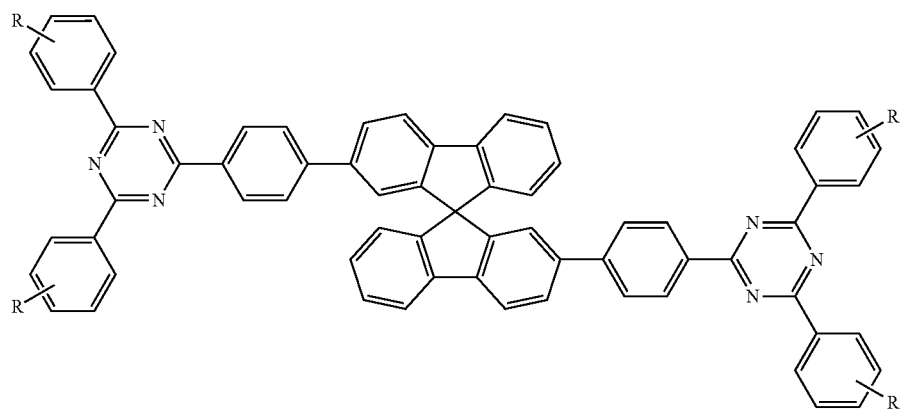

formula (8)

wherein R represents an alkyl group having 1 to 4 carbon atoms.

According to the forth aspect of embodiments, there is provided an ink composition comprising at least one of the above compounds in a medium which is a liquid at room temperature.

According to the fifth aspect of embodiments, there is provided a solid or liquid composition, comprising:
a compound represented by a formula (9), and
at least one of the above compounds:

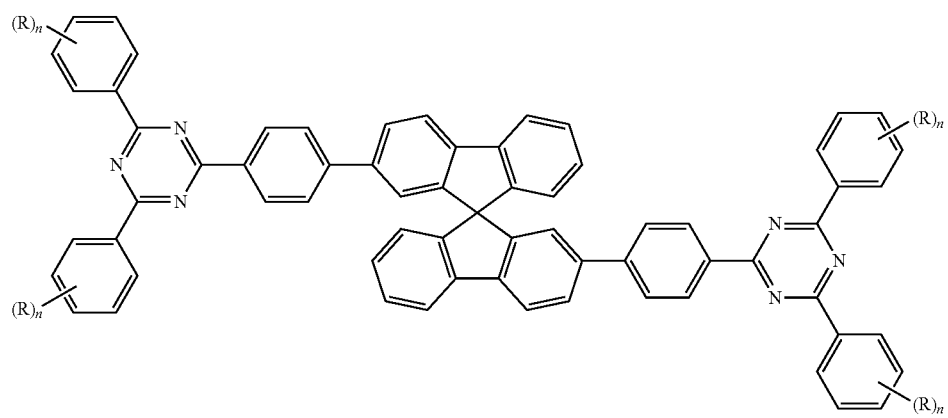

Formula (9)

wherein R represents an alkyl group and n represents an integer from 0 to 3 which indicates the number of substituents.

According to the sixth aspect of embodiments, there is provided a light-emitting device comprising a light-emitting layer containing a light-emitting material as at least one layer between electrodes facing each other or between a positive electrode and a negative electrode, wherein the at least one layer between electrodes facing each other or between a positive electrode and a negative electrode contains the above compound.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a cross-sectional view of an organic electroluminescent device according to an embodiment of the present invention;

FIG. 2A is a $^1$H-NMR chart of a compound 1 according to an example of the present invention;

FIG. 5B is an magnified view of an NMR chart of FIG. 5A;

FIG. 7A is a $^1$H-NMR chart of a compound 31 according to an example of the present invention;

FIG. 10 is a fluorescent spectrum chart of a compound 32 according to an example of the present invention and a fluorescent spectrum chart when a compound 32 is doped with a compound 2;

FIG. 11 is a cross-sectional view of a donor base material according to an embodiment of the present invention;

FIG. 12 is a fluorescent spectrum chart measured for a film containing a compound according to an example of the present invention; and FIG. 13 is an explanatory view for explaining a transfer method using a donor base material according to an embodiment of the present invention.

DETAILED DESCRIPTION OF THE INVENTION

Figure 2B:
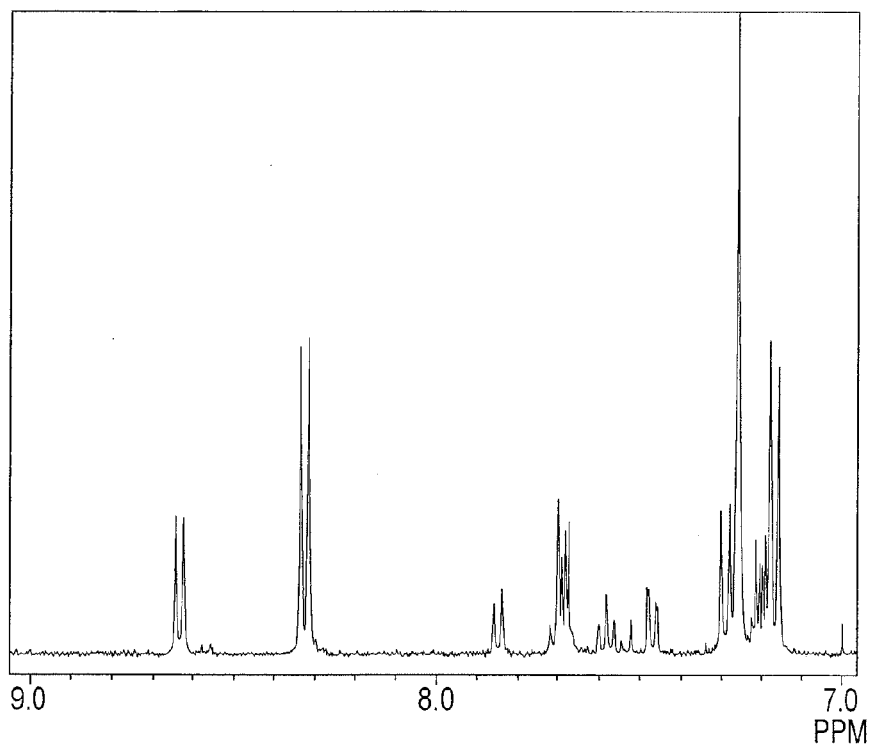
FIG. 2B is an enlarged view of the NMR chart of FIG. 2A.

The present invention will be explained in more detail.

According to the present invention, the following compounds are provided which are shown by a structure represented by the formula (1):

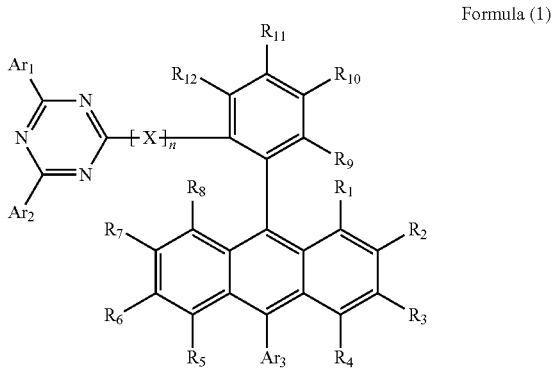

Formula (1)

wherein

X represents a residue derived from an aryl ring or a heteroaryl ring which may have one or more substituents or a single bond;

$Ar_1$ and $Ar_2$ respectively represent an unsubstituted or substituted phenyl group or heteroaryl group;

$Ar_3$ represents a group having 60 or less carbon atoms, the group represents a structure in which six or less aryl or heteroaryl groups which may have one or more substituents are conjugatedly linked, or the same group as a substituent at the ninth or tenth position on the anthracene ring;

the substituents on X and $Ar_1$ to $Ar_3$, and $R_1$ to $R_{12}$ are respectively selected from the group consisting of hydrogen, deuterium, fluorine, a cyano group, a trifluoromethyl group, a trimethylsilyl group, an alkyl group, an alkoxy group and a polyoxyalkylene group having 15 or less carbon atoms, a substituted or unsubstituted aryl group and heteroaryl group having 15 or less carbon atoms, and a crosslinkable substituent having 15 or less carbon atoms;

provided that $R_1$ to $R_{12}$ may have a structure in which adjacent substituents are combined to each other to form a ring; and n denotes an integer of 0 or 1.

Here, the residue which is represented by X and derived from an aryl ring or heteroaryl ring which may have a substituent means a divalent residue derived from a benzene ring, pyridine ring, or the like which may have a substituent.

$Ar_1$ and $Ar_2$ each have a structure provided with a phenyl group or heteroaryl group such as a pyridyl group or carbazolyl group, as its skeleton and with an optional substituent on its skeleton.

Examples of the alkyl group having 15 or less carbon atoms include a methyl group, isopropyl group, sec-butyl group, t-butyl group, pentyl group and octyl group. Examples of the alkoxy group having 15 or less carbon atoms include a methoxy group, isopropyloxy group, methoxyethyloxy group, 2-ethylhexyloxy group, and 3,7-dimethyloctyloxy group. Examples of the polyoxyalkylene group having 15 or less carbon atoms include a 2-(2-methoxyethoxy)ethoxy group superior in solubility in a polar solvent, which is suitable to use in an electrochemiluminescence (ECL) type organic electroluminescent device. Examples of the substituted or unsubstituted aryl group having 15 or less carbon atoms include a phenyl group, tolyl group, xylyl group, mesityl group, biphenyl group, and naphthyl group. Examples of the substituted or unsubstituted heteroaryl group having 15 or less carbon atoms include a pyridyl group, bipyridyl group, pyrimidinyl group, 2-t-butylpyrimidine-5-yl group, phenanthryl group, 2,4-diaryl-1,3,5-triazine-6-yl group, carbazole-9-yl group, 6-methylbenzothiazole-2-yl group, and N-phenylbenzoimidazole-2-yl group. Examples of the crosslinkable group having 15 or less carbon atoms include, though are not particularly limited to, groups having an alkenyl group such as a vinyl group, trifluorovinyl group, acryl group, methacryl group, or pentenyl group, maleimide group, epoxy ring, or oxetane ring at their terminals, groups having alkoxysilane or alkoxytitanium, and groups having a thiol group, hydroxyl group, or amino group.

Further, $R_1$ to $R_{12}$ may have a structure in which adjacent substituents are combined to each other to form an aliphatic ring or aromatic ring such as a cyclohexane ring, benzene ring, or phenanthrene ring.

The synthetic reaction formula (1) shows an example of a synthetic route of the compound represented by the formula (1) according to the present invention. First, a synthetic route using a 9,10-dibromoanthracene derivative as a starting material will be explained.

Here, the substituent A in the synthetic reaction formula is selected from iodine, bromine, chlorine, and triflate. The substituent B represents a group having boron in a Suzuki-Miyaura coupling reaction and is selected from boric acid, a borate of boric acid and bis(pinacolate)diboron or the like, and boron trifluoride such as potassium trifluoroboron.

Synthetic reaction formula (1)

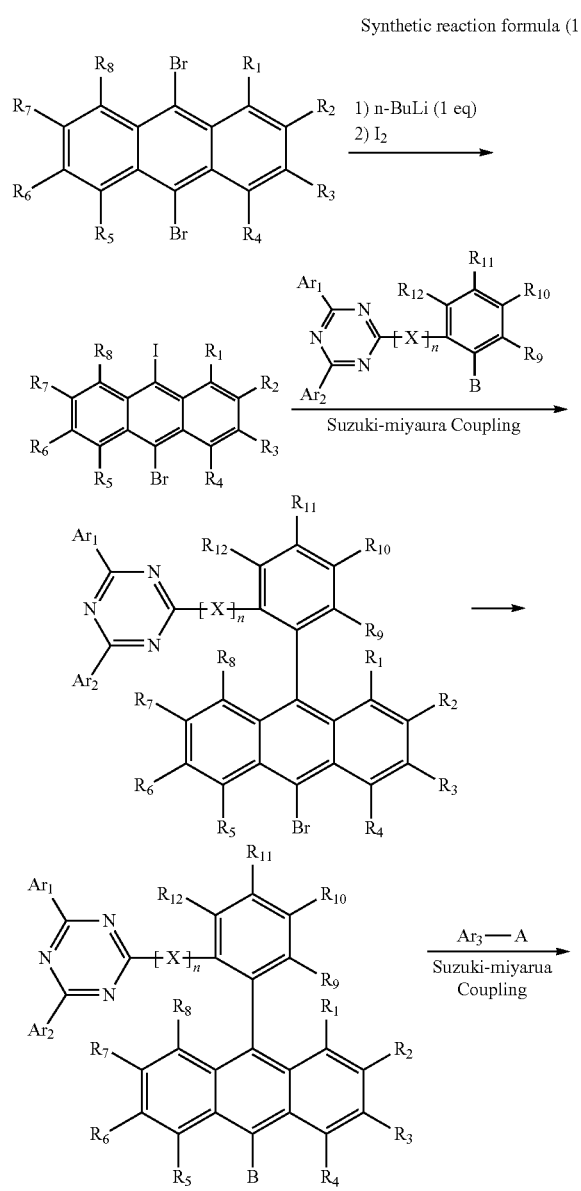

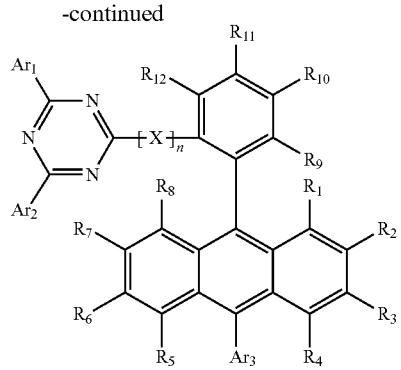

In the synthetic reaction formula (1), X, $Ar_1$ to $Ar_3$, $R_1$ to $R_{12}$, and n are the same as those defined in the above formula (1).

The synthetic reaction formula (1) is an example of the synthetic route in the case that the substituents at the ninth and tenth positions of anthracene are different from each other (i.e. asymmetrical substitution). The route is effective because a substituent having a smaller molecular weight can be selected as one group in the case of intending to obtain a material reduced in molecular weight to attain sublimation and vapor deposition easily. However, the route has the problem that the number of synthetic steps is increased, leading to increased cost. Even if the same substituent exists at the ninth and tenth positions, an amorphous material having a solubility sufficient and glass transition temperature high enough for the wet process can be obtained. Therefore, it is not necessary to synthesize an asymmetrical compound in which the substituents at the ninth and tenth positions differ from each other.

As an example of the compound represented by the above formula (1), compounds represented by the following formula (2) are given:

Formula (2)

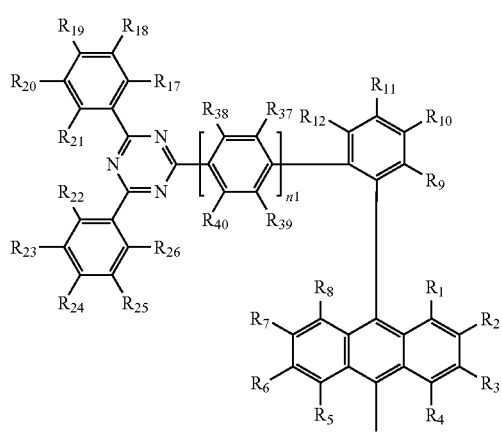

-continued

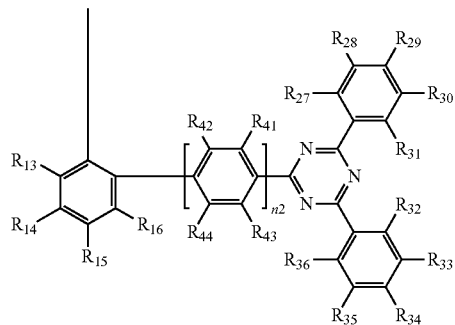

wherein each of $R_1$ to $R_{44}$ is independently selected from the group consisting of hydrogen, deuterium, fluorine, a cyano group, a trifluoromethyl group, a trimethylsilyl group, an alkyl group, an alkoxy group and a polyoxyalkylene group having 15 or less carbon atoms, a substituted or unsubstituted aryl group and heteroaryl group having 15 or less carbon atoms, and a crosslinkable substituent having 15 or less carbon atoms; and each of n1 and n2 independently represents an integer of 0 or 1.

As an example of the compound represented by the above formula (2), compounds represented by the following formula (3) are given:

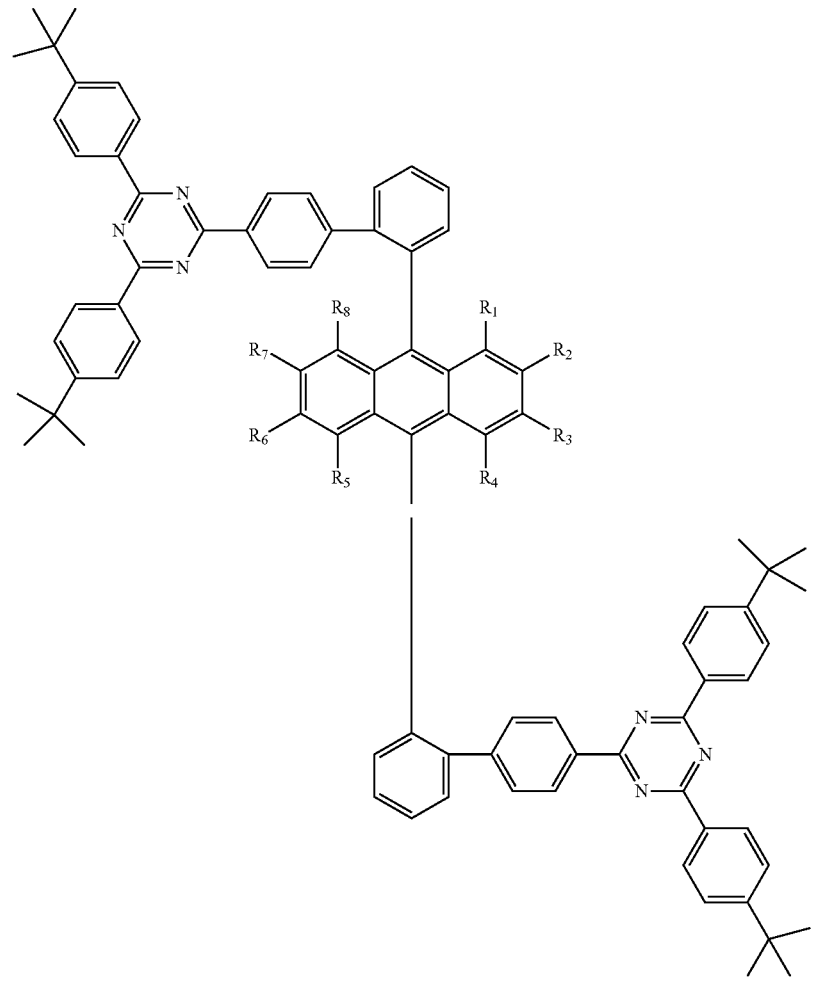

Formula (3)

wherein each of $R_1$ to $R_8$ is independently selected from the group consisting of hydrogen, deuterium, fluorine, a cyano group, a trifluoromethyl group, a trimethylsilyl group, an alkyl group, an alkoxy group, and a polyoxyalkylene group having 15 or less carbon atoms, a substituted or unsubstituted aryl group and heteroaryl group having 15 or less carbon atoms, and a crosslinkable substituent having 15 or less carbon atoms.

The following synthetic reaction formulae (2) to (4) show examples of the method of synthesizing the compound represented by the formula (3) in which the substituents at ninth and tenth positions are same as each other.

The synthetic reaction formula (2) is an example of the synthetic method based on the Suzuki-Miyaura coupling reaction using a 9,10-dibromoanthracene derivative as a starting material. The synthetic reaction formulae (3) and (4) are examples of the synthetic method using an anthraquinone derivative as a starting material.

In the synthetic reaction formulae, $R_1$ to $R_8$ are as defined in above formula (3).

Here, the substituent A in the synthetic reaction formulae is selected from iodine, bromine, chlorine, and triflate. The substituent B represents a group having boron in a Suzuki-Miyaura coupling reaction and is selected from boric acid, a borate of boric acid and bis(pinacolate)diboron or the like, and boron trifluoride such as potassium trifluoroboron. In the synthetic reaction formula (2), coupling of a reverse combination is allowed in which A is boron and B is a halogen as it is.

An example of a synthetic route of a triaryltriazine derivative containing the substituents A and B is shown in the synthetic reaction formula (5). Analogous compounds using a raw material containing a heteroaryl ring such as a pyridine ring and also analogous compounds having different substituents can be synthesized by the similar reaction.

Synthetic reaction formula (2)

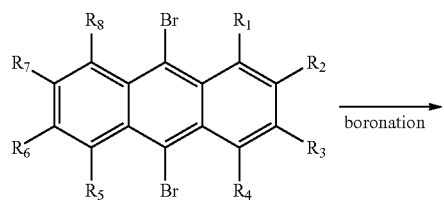

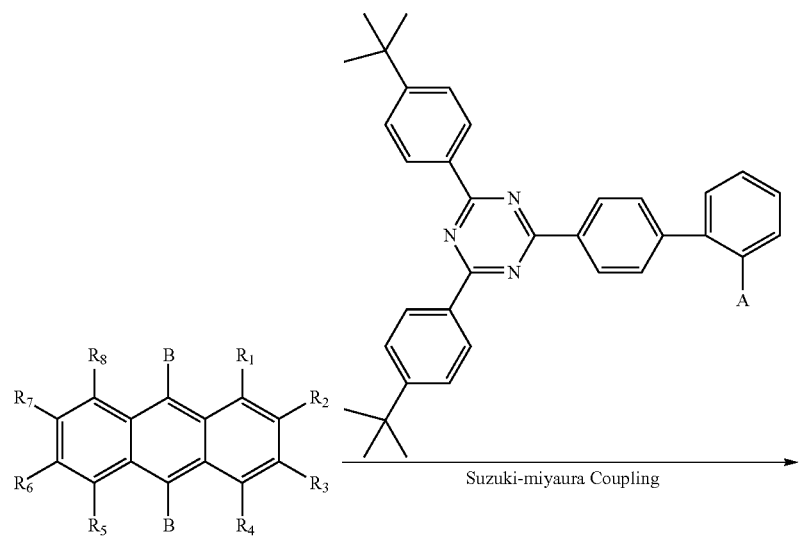

-continued
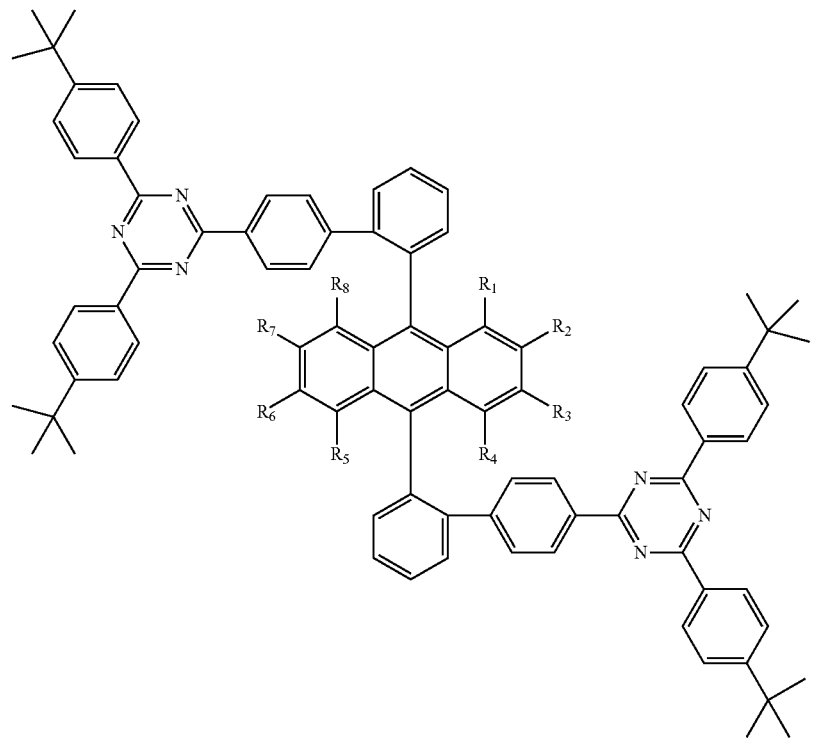
Synthetic reaction formula (3)
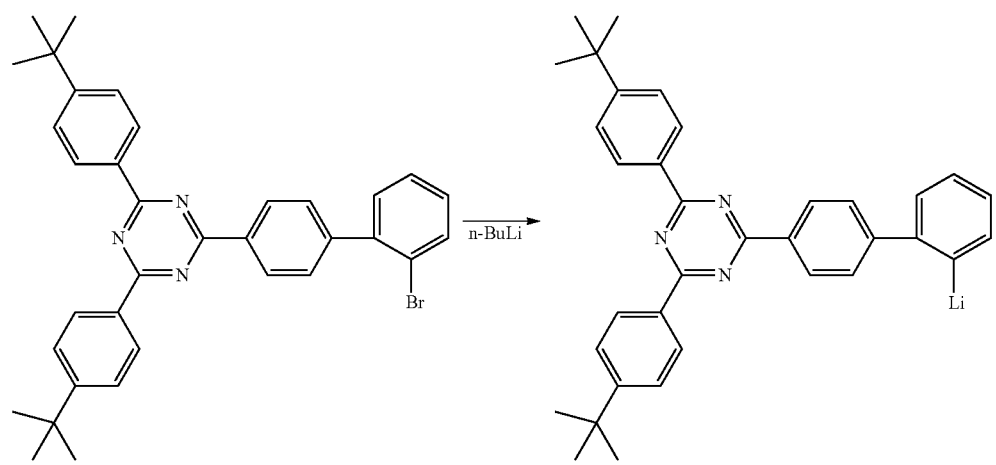

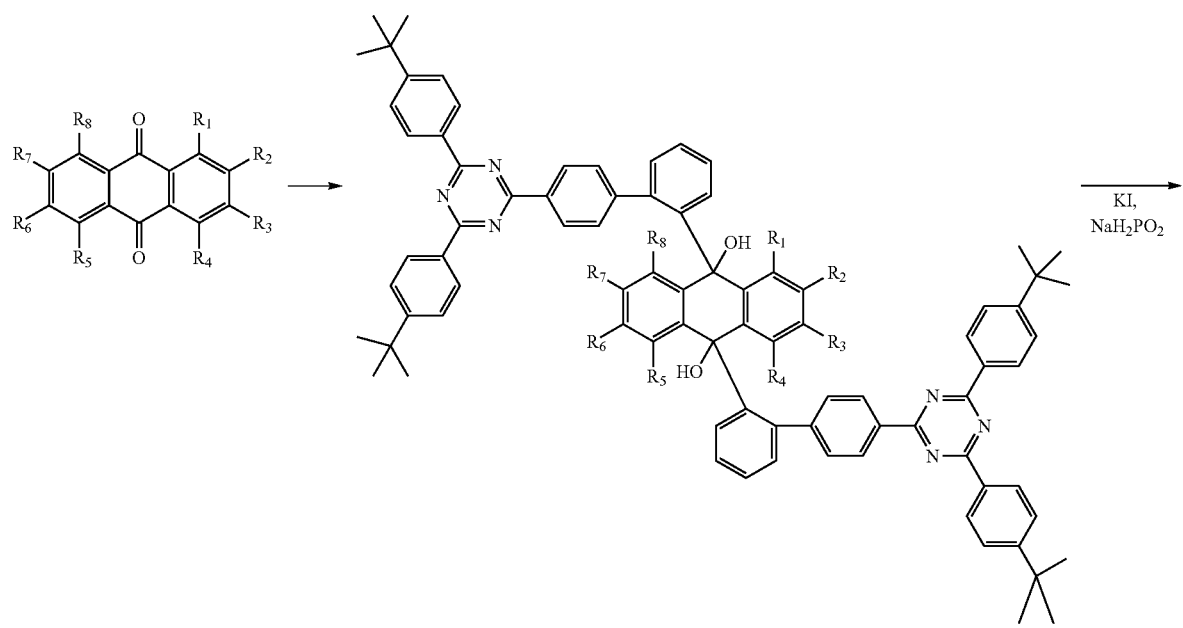
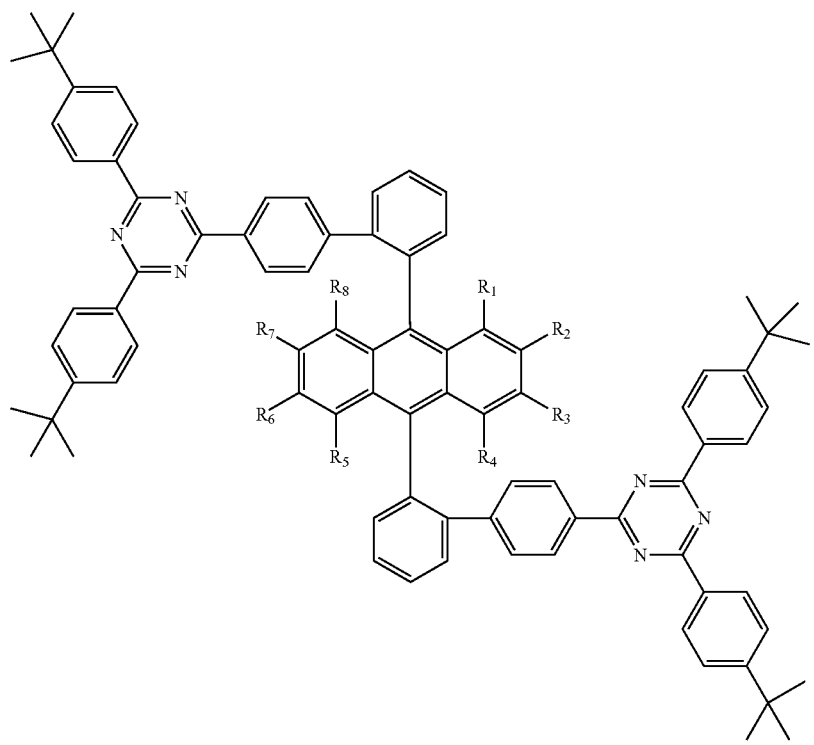

-continued
Synthetic reaction formula (4)
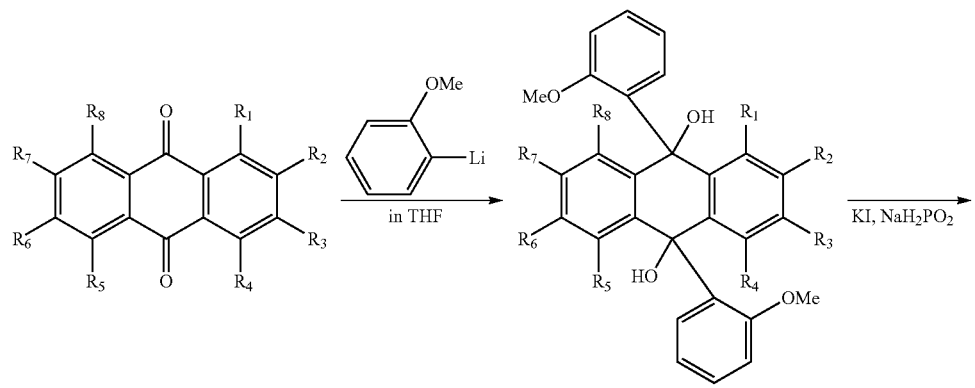
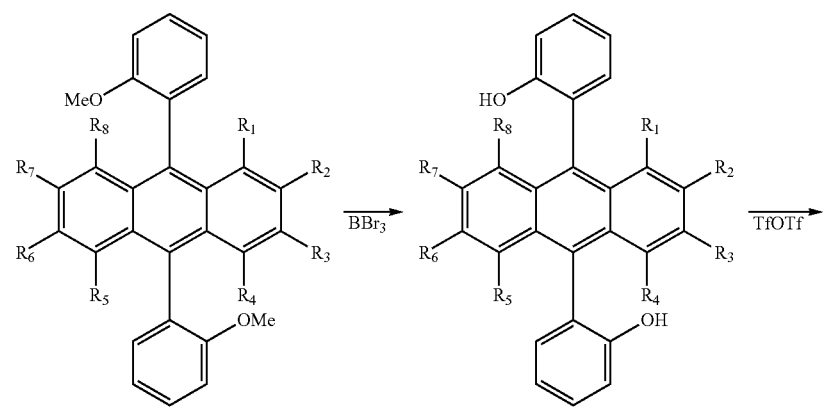
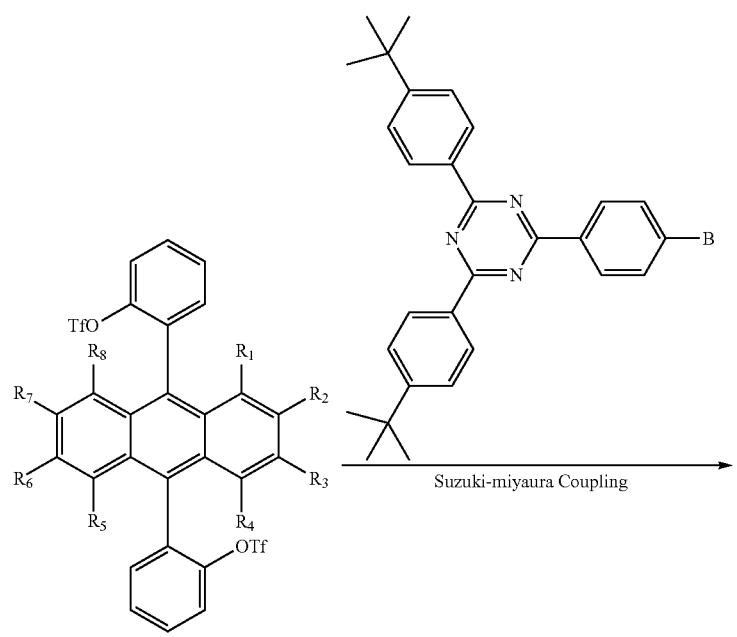

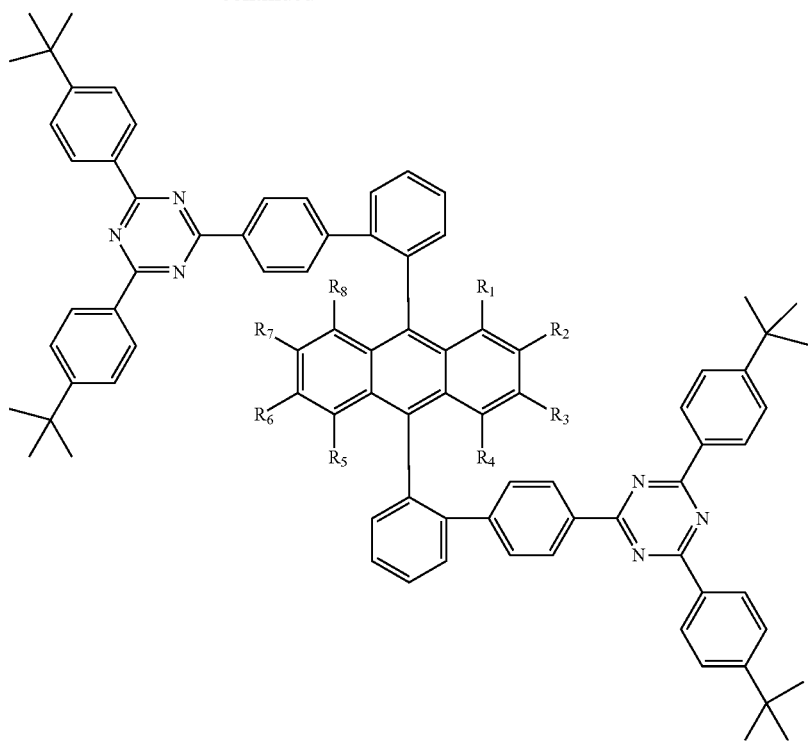
Synthetic reaction formula (5)
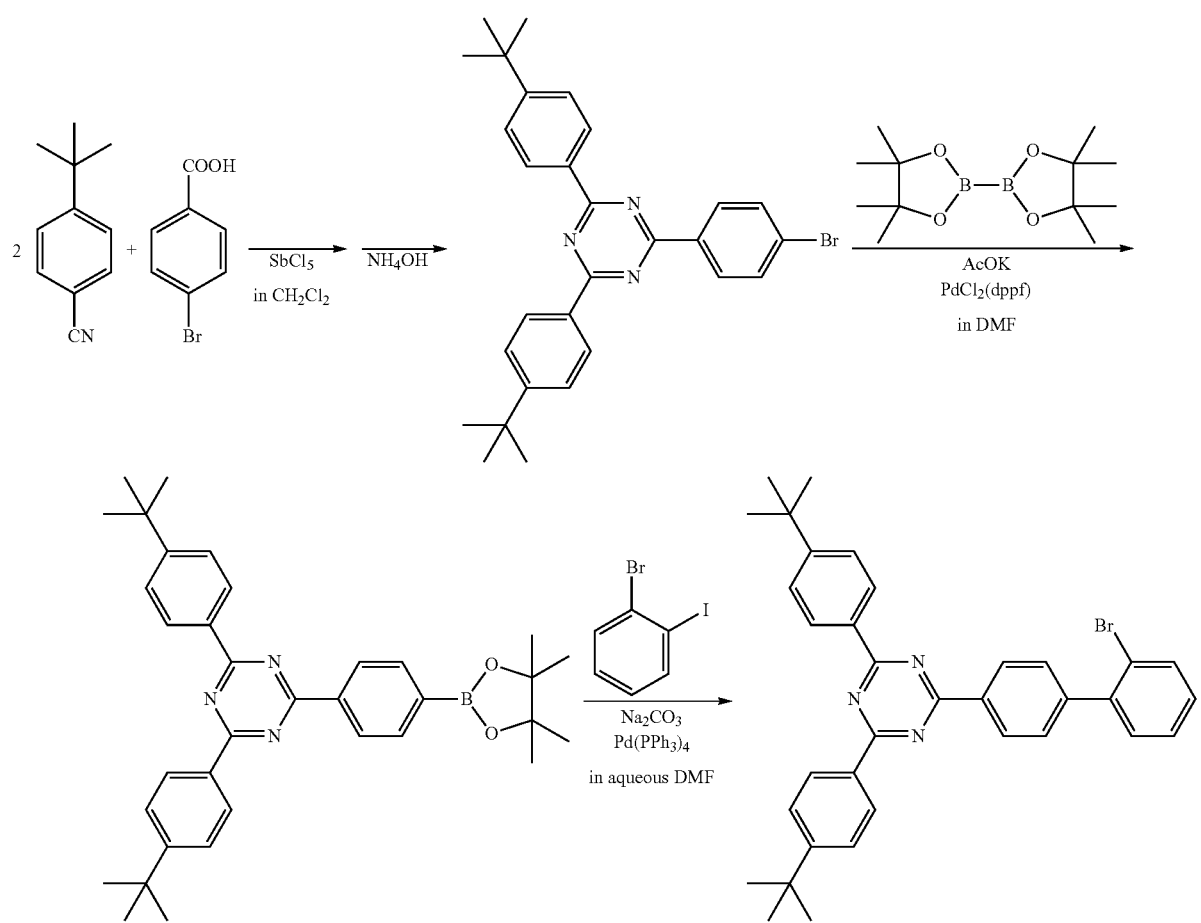

Specific examples of the compound of the present invention are shown by the following compounds 1 to 30 and the following formulae (4) to (7).
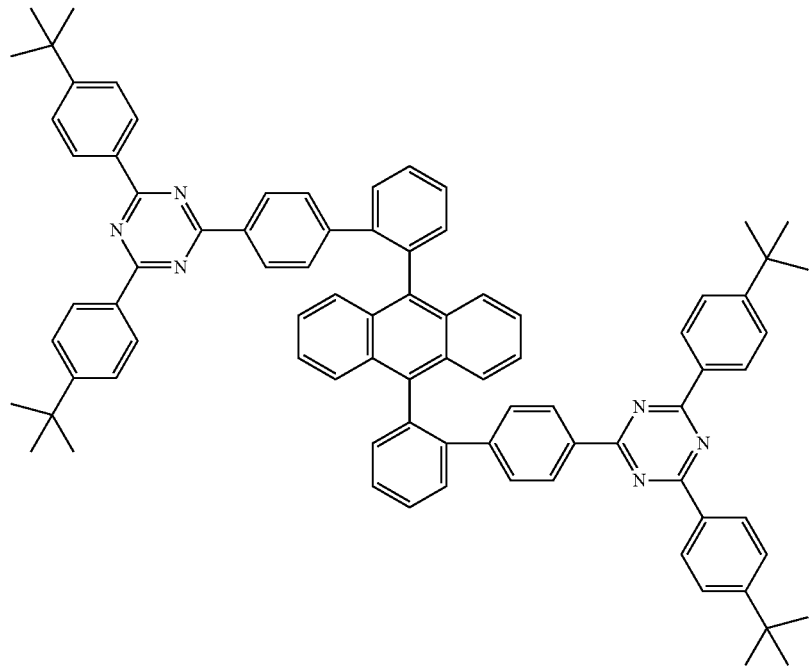
Compound 1
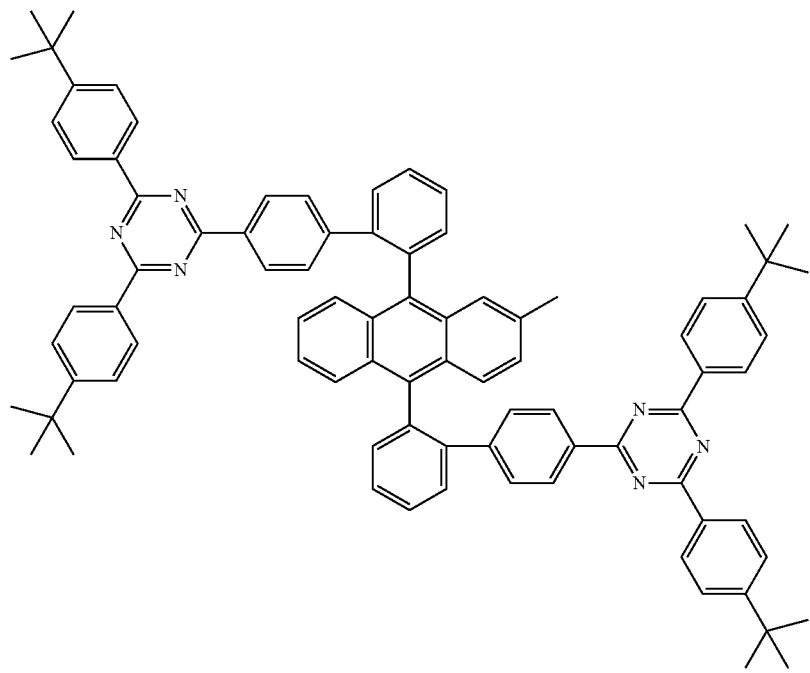
Compound 2

-continued
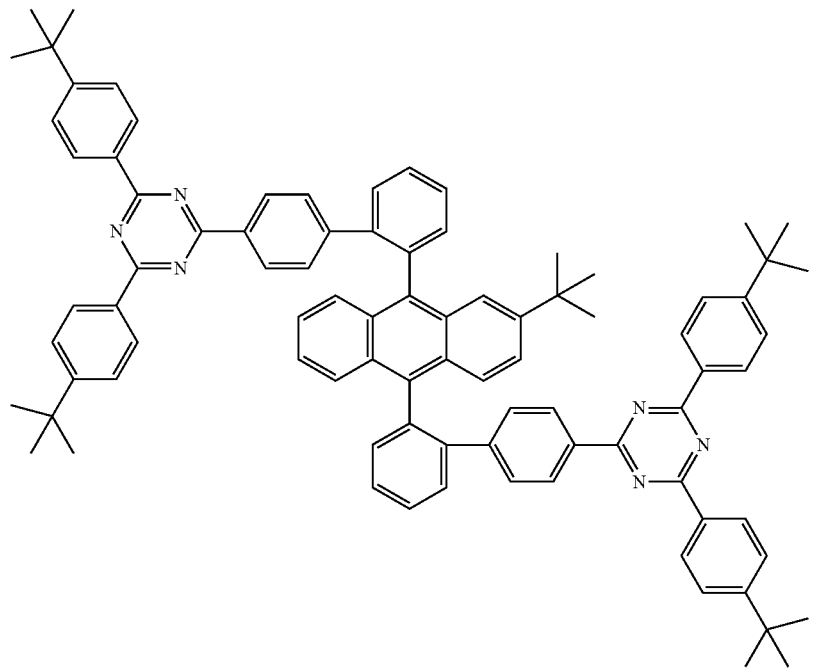
Compound 3
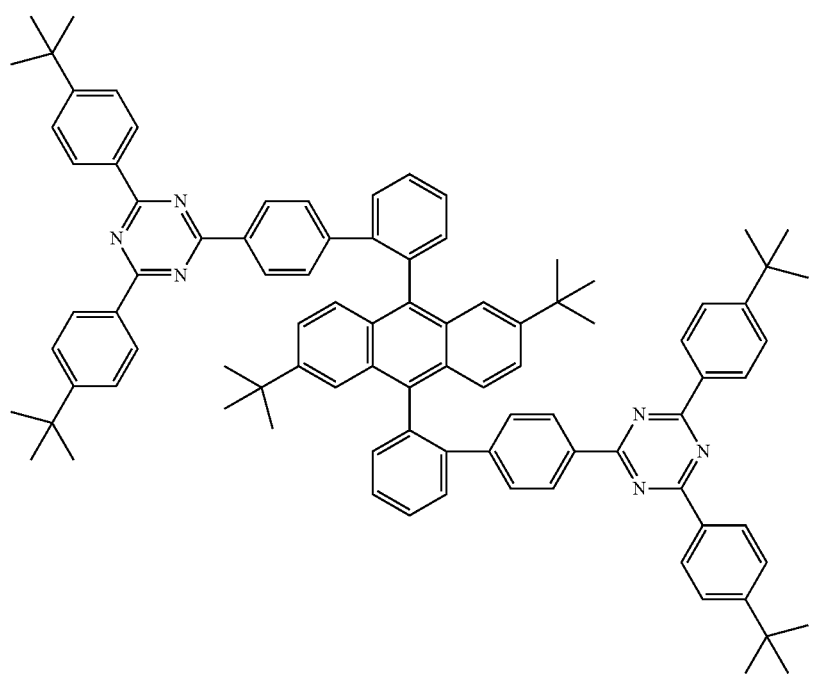
Compound 4

-continued
Compound 5
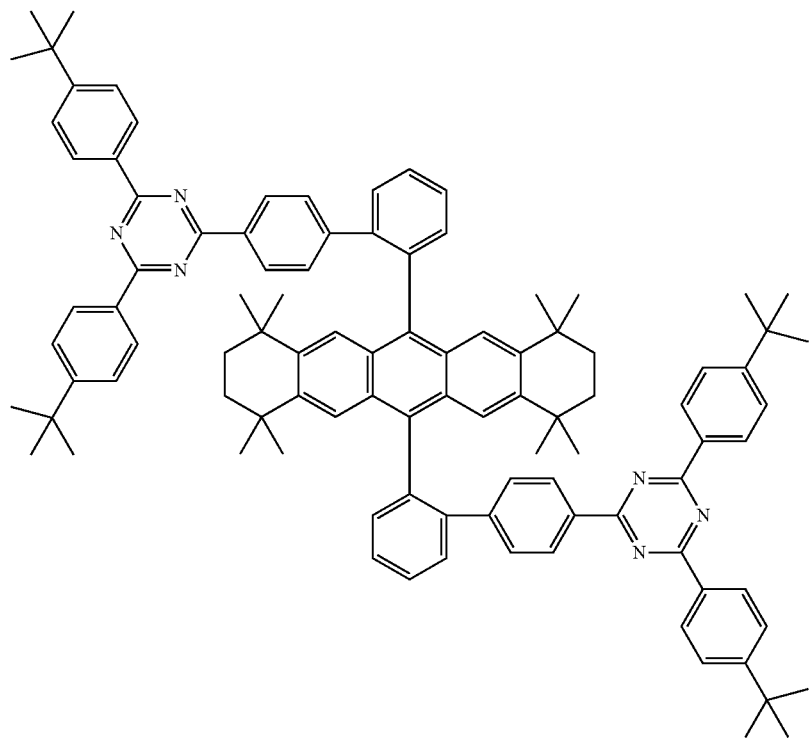
Compound 6
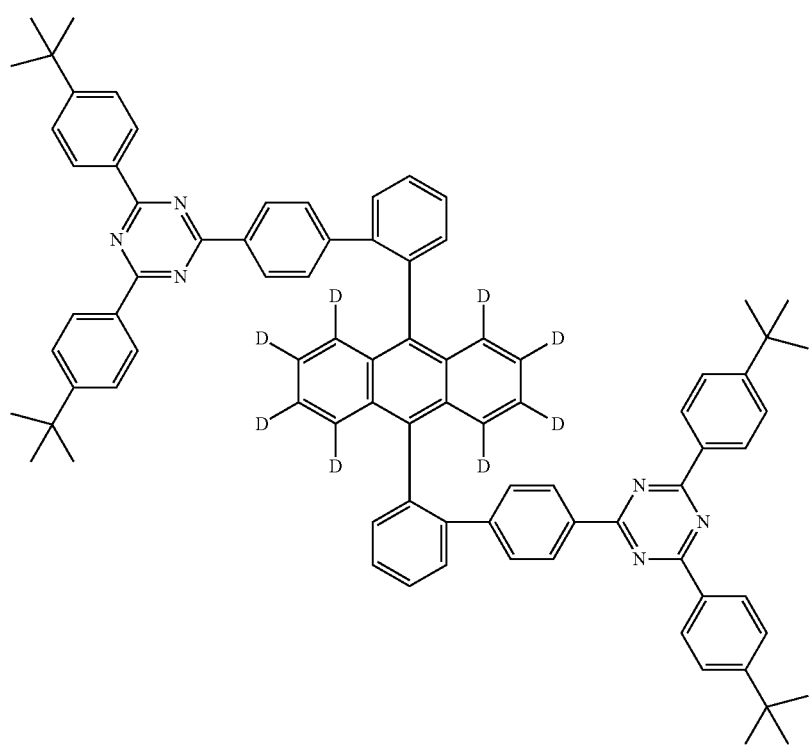

Compound 7
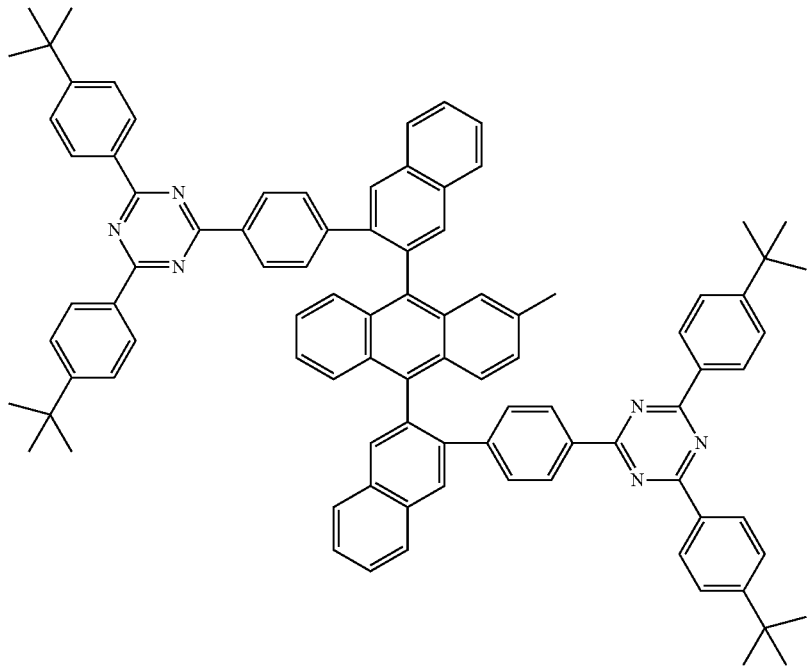
Compound 8
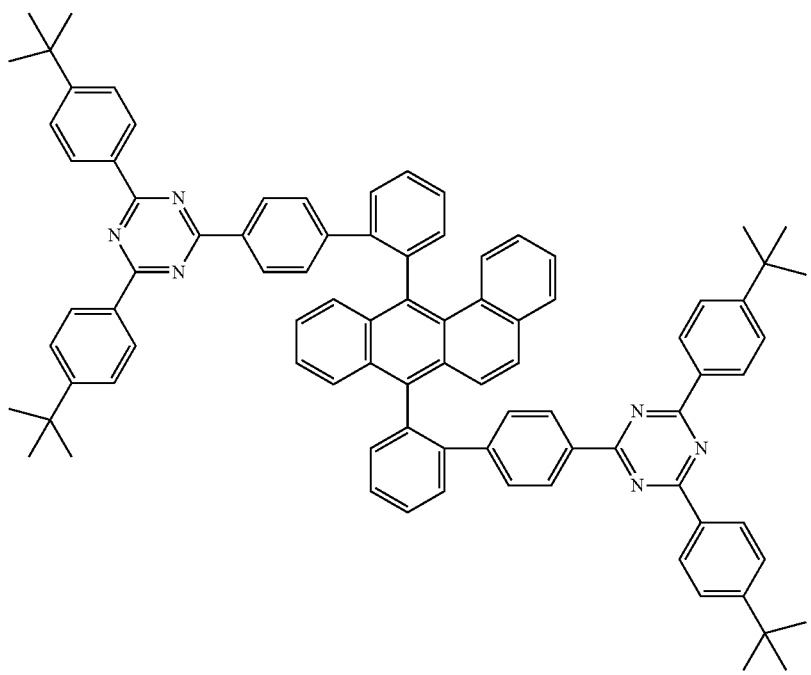

Compound 9
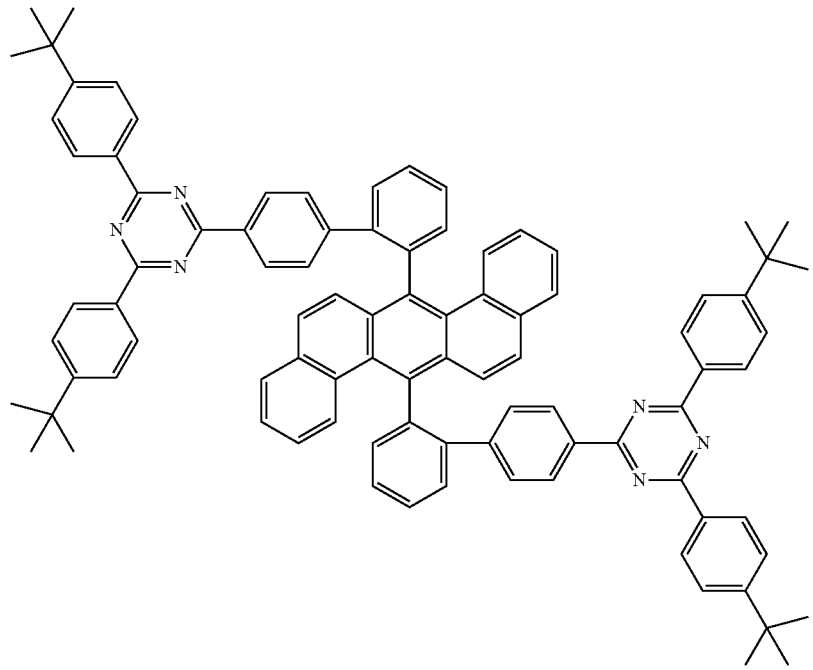
Compound 10
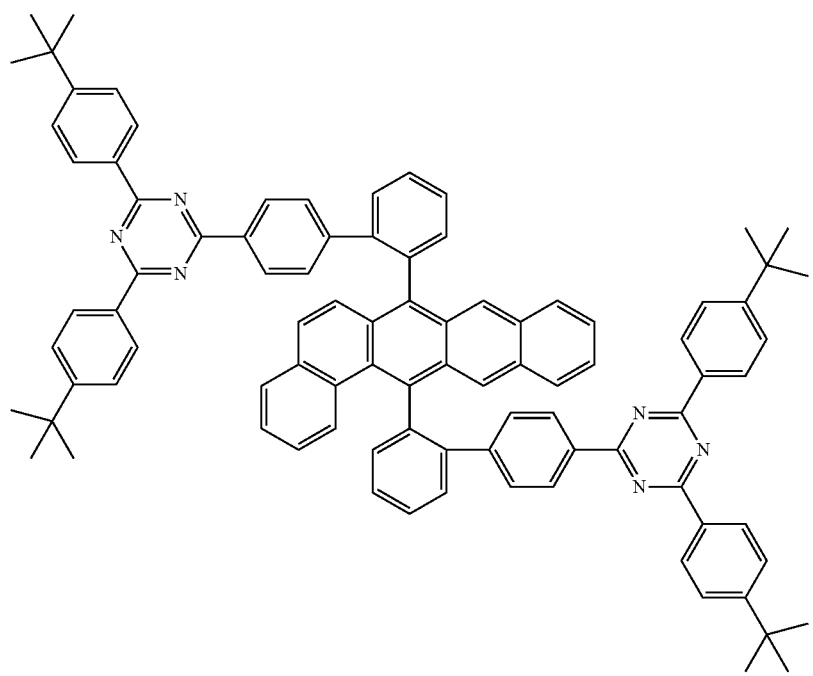

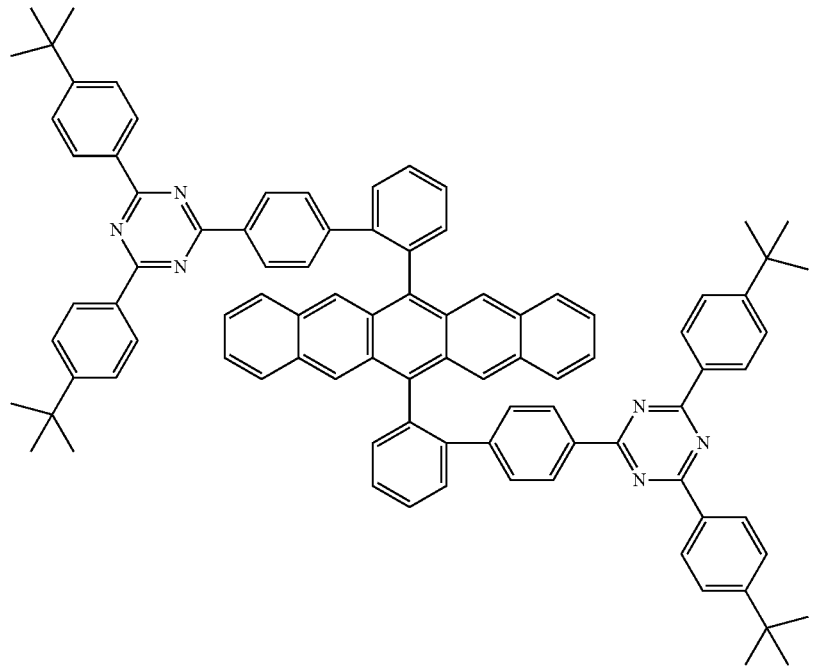
Compound 11
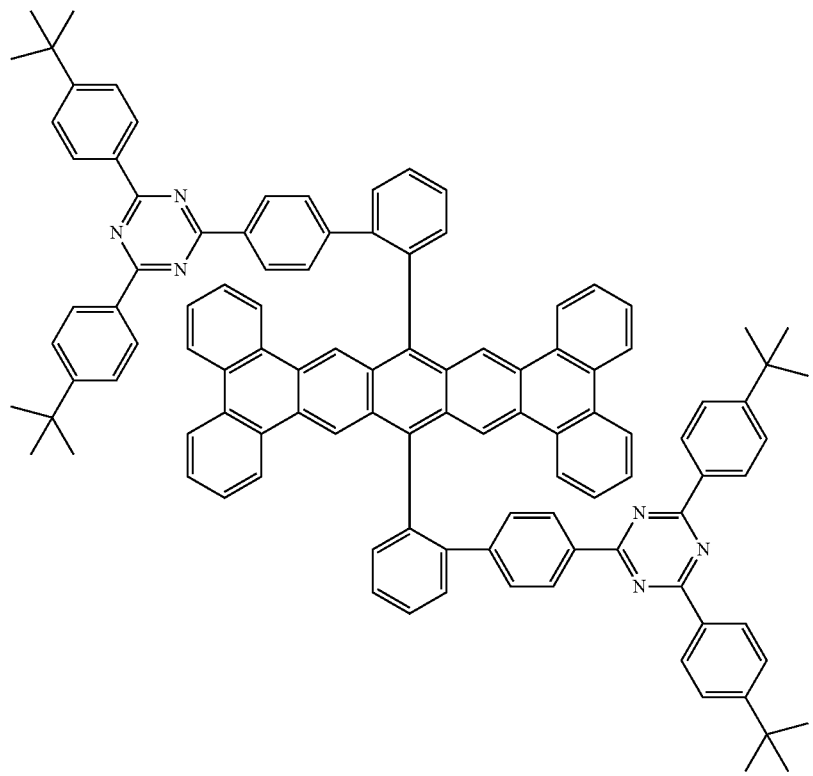
Compound 12

-continued
Compound 13
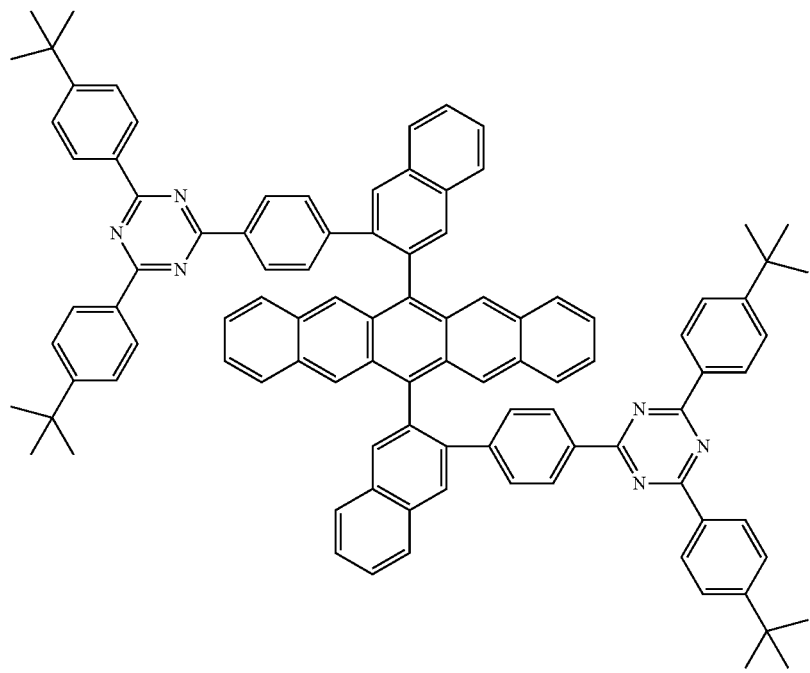
Compound 14
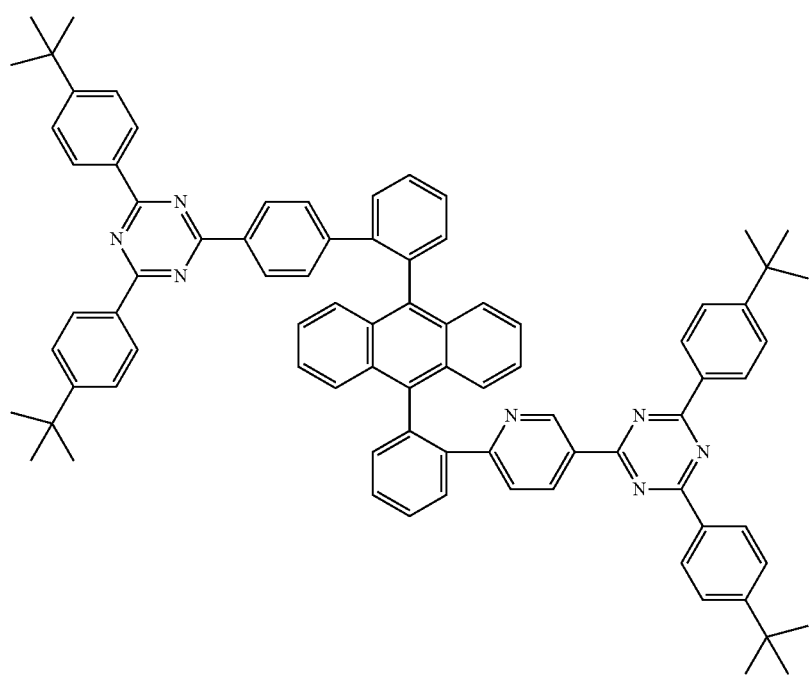

Compound 15
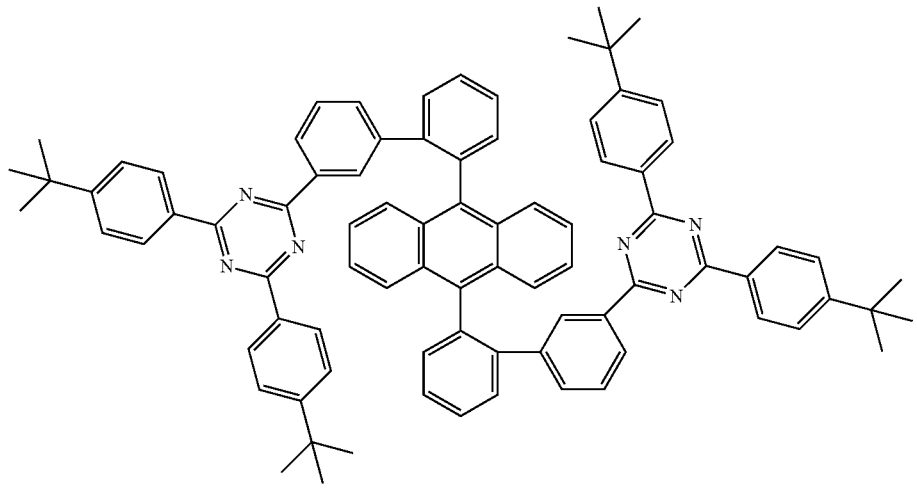
Compound 16
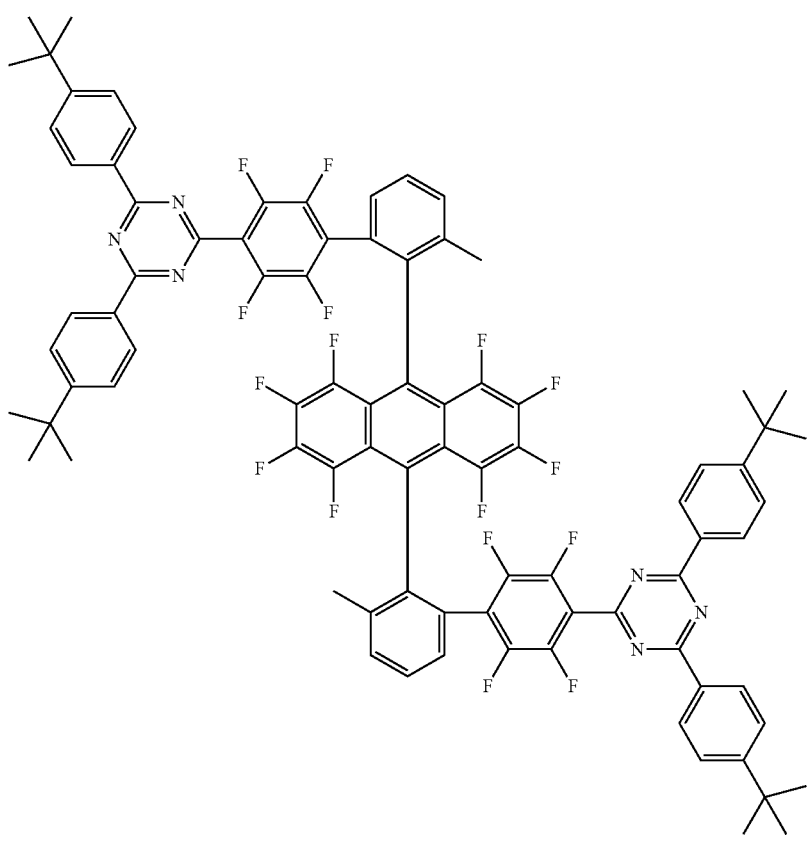

-continued
Compound 17
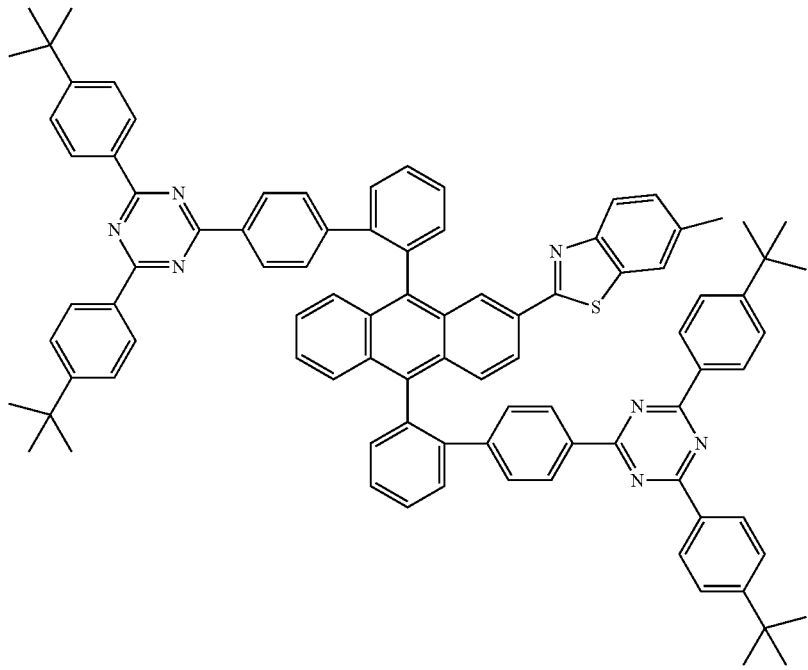
Compound 18
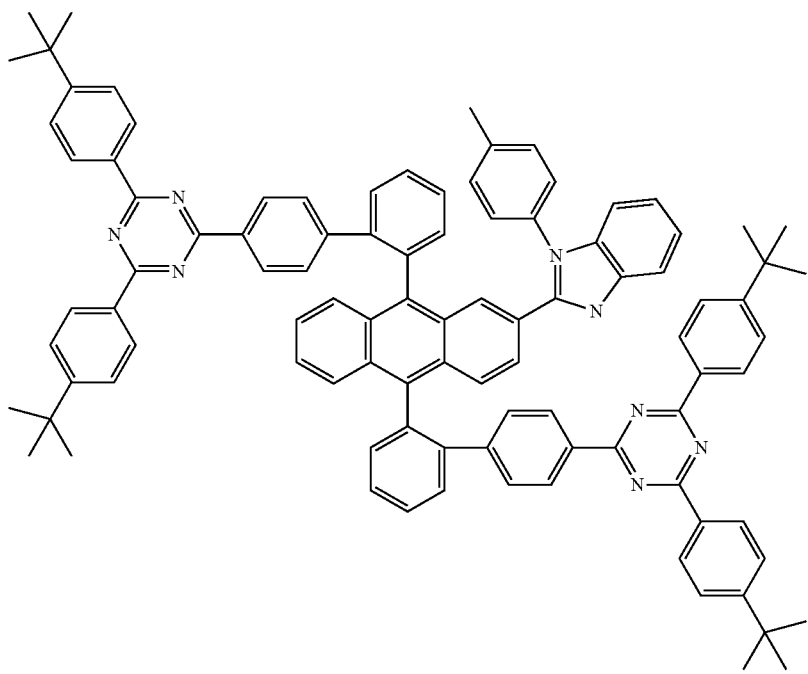

-continued
Compound 19
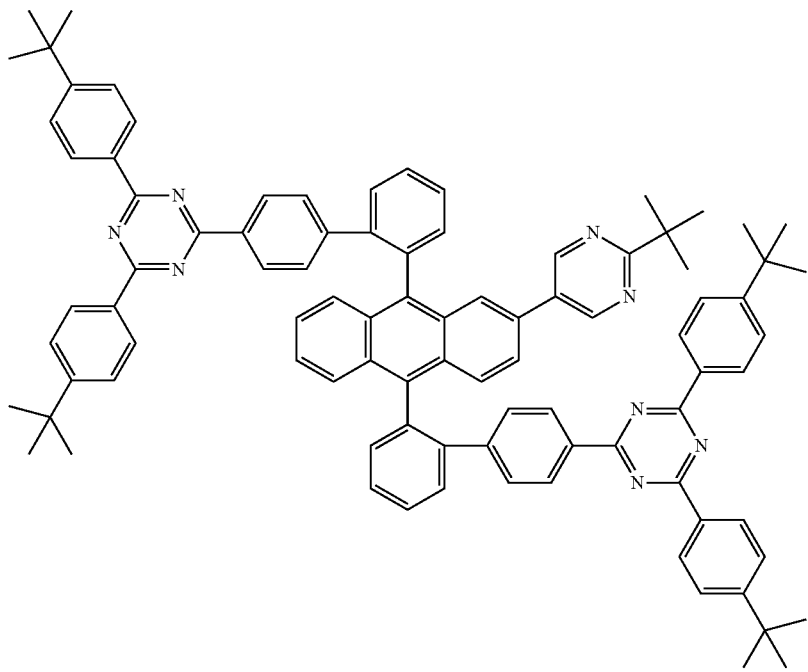
Compound 20
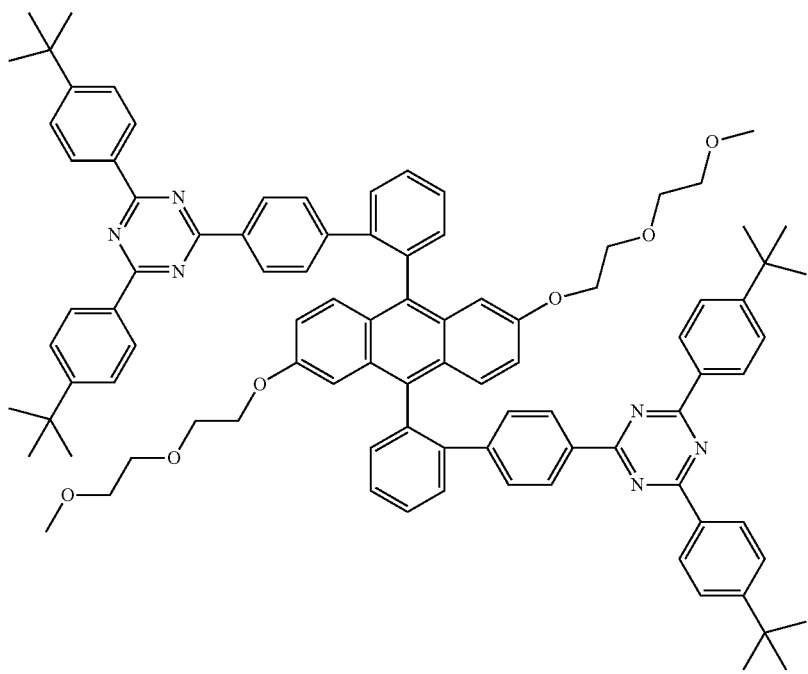

Compound 21
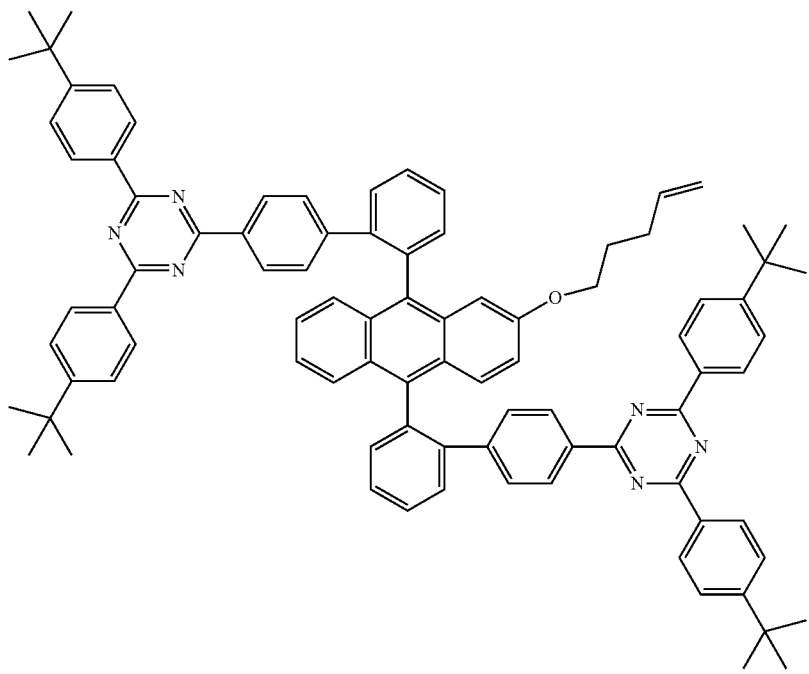
Compound 22
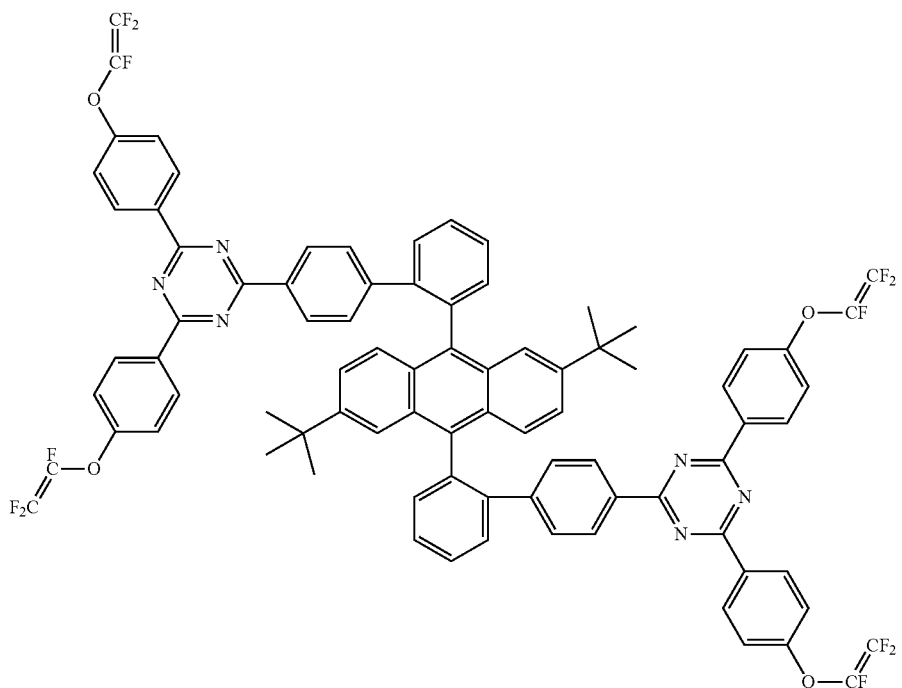

-continued
Compound 23
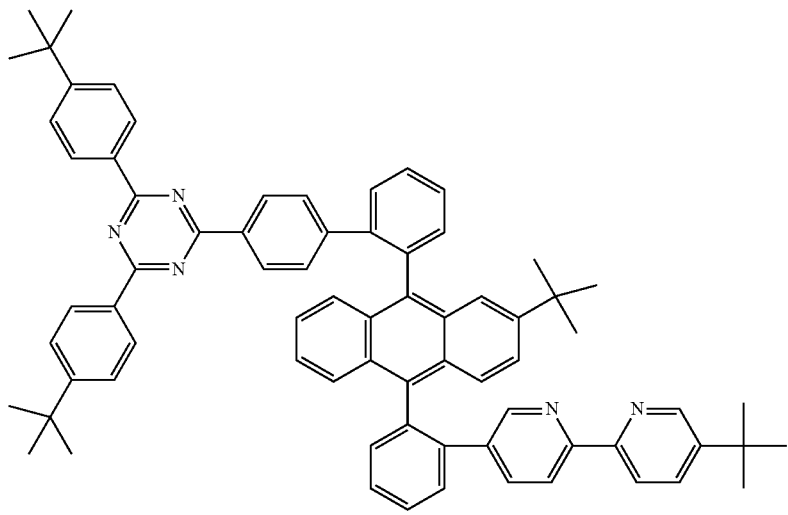
Compound 24
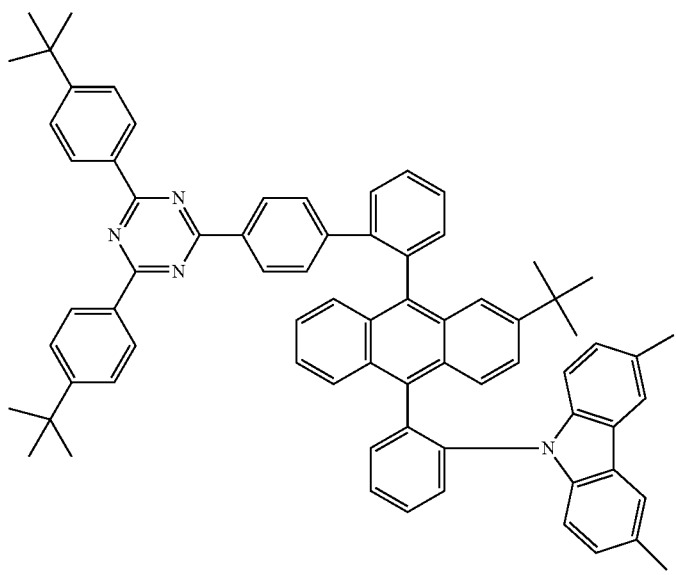
Compound 25
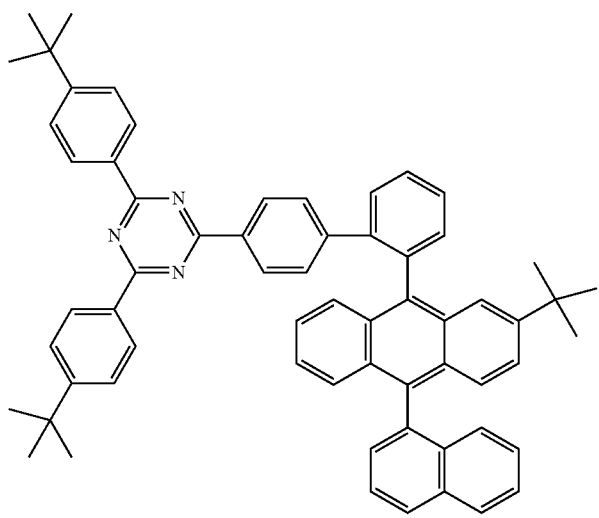

Compound 26
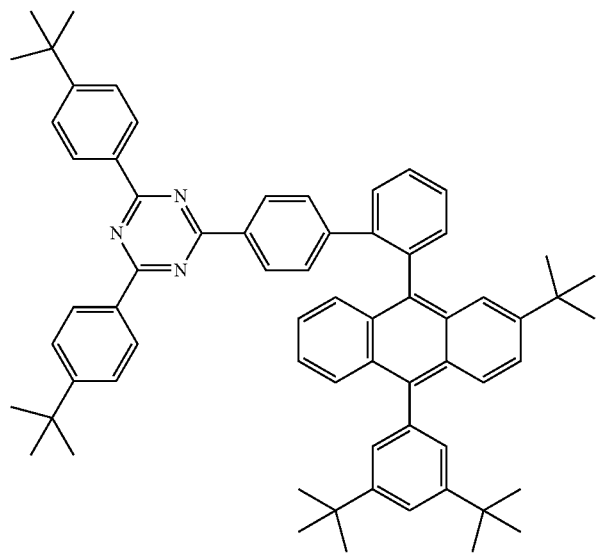
Compound 27
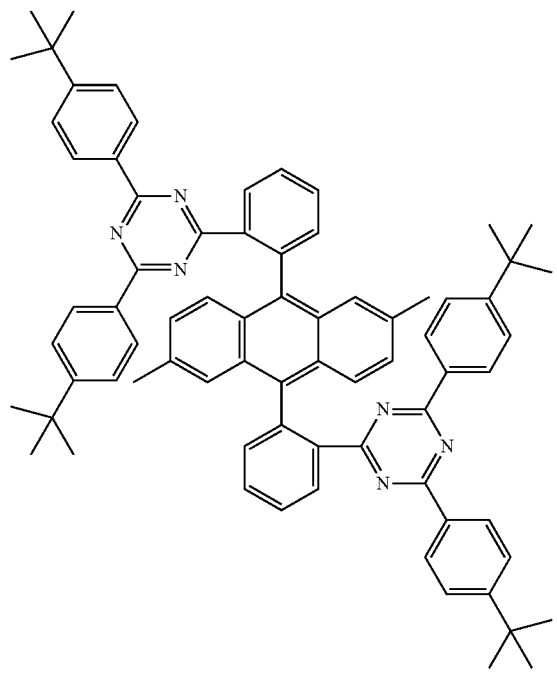

-continued
Compound 28
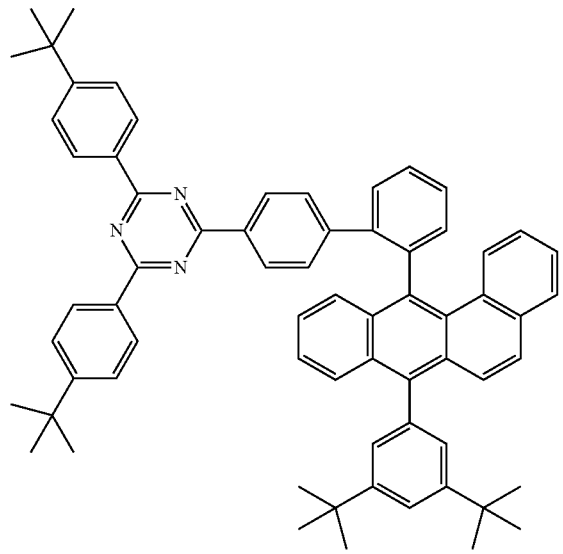
Compound 29
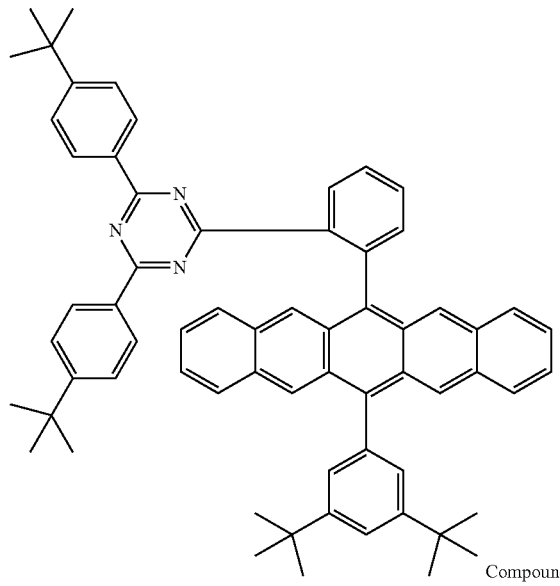
Compound 30
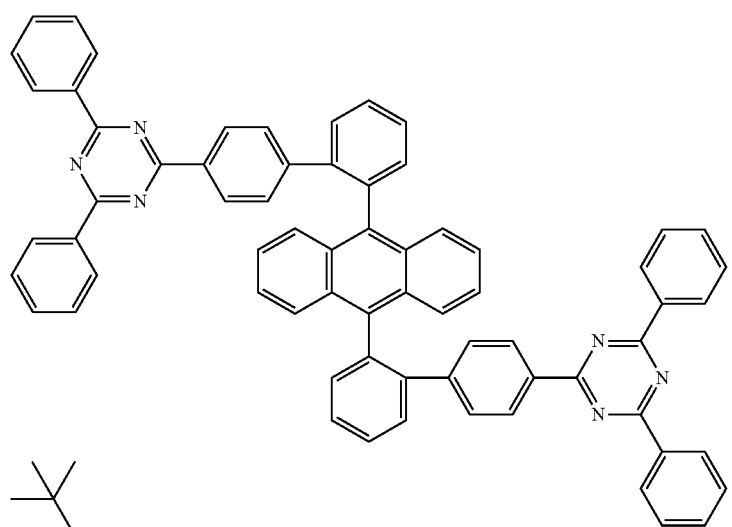
Formula (4)
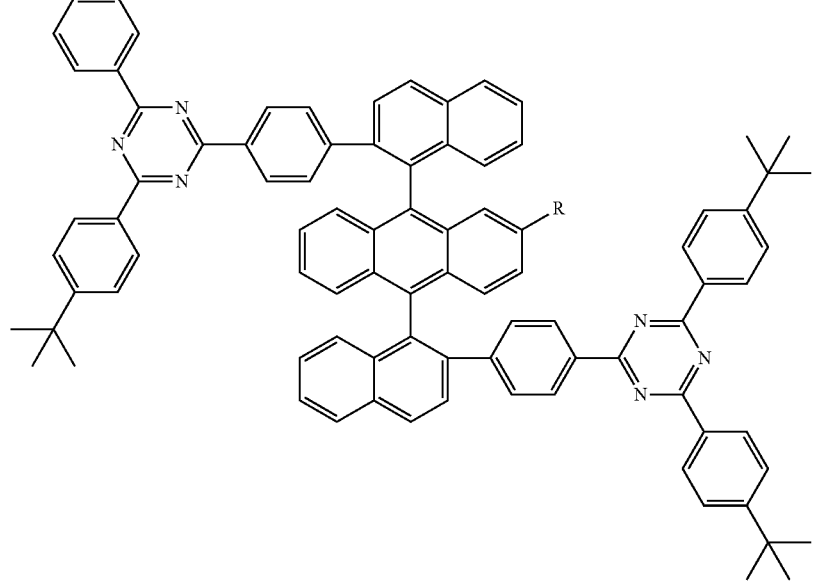

wherein R represents hydrogen, a methyl group, or a t-Bu group.
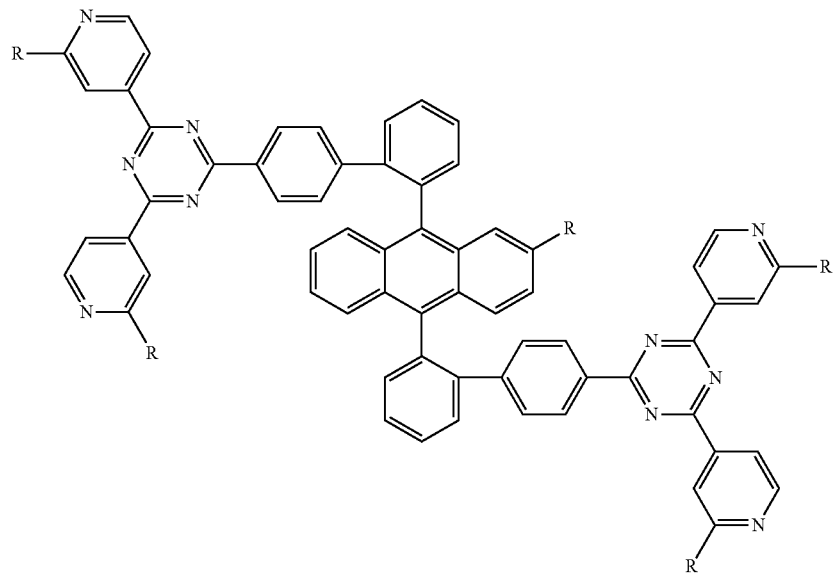
Formula (5)
wherein each of R is independently selected from hydrogen, a methyl group, or a t-Bu group.
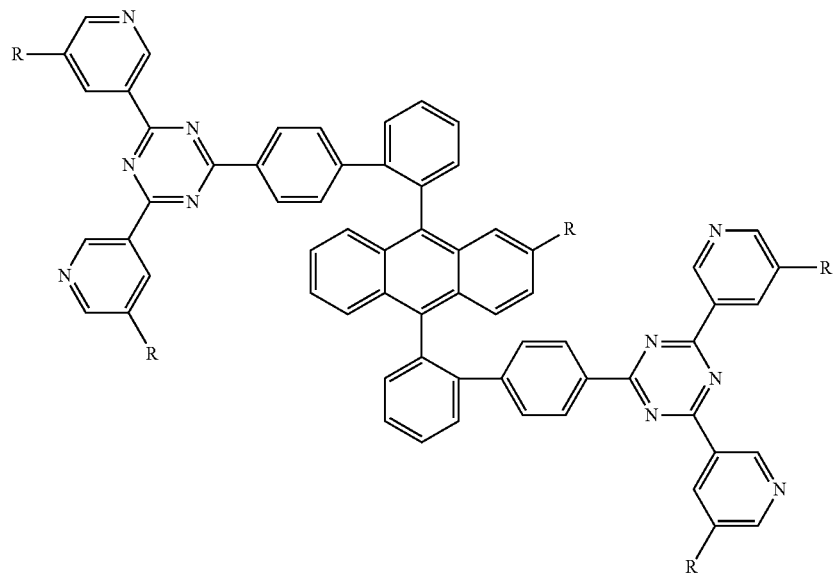
Formula (6)

wherein each of R is independently selected from hydrogen, a methyl group, or a t-Bu group.

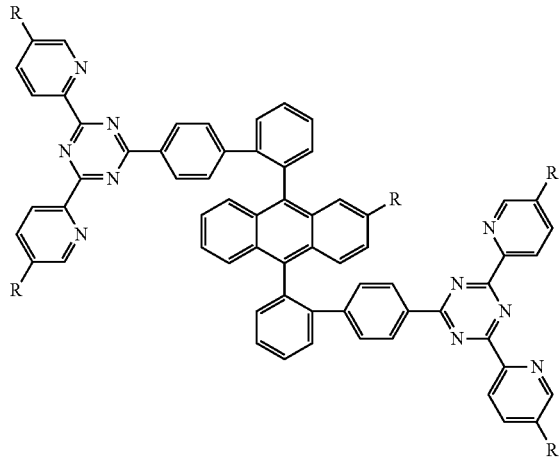

Formula (7)

wherein each of R is independently selected from hydrogen, a methyl group, or a t-Bu group.

According to an embodiment of the present invention, an ink composition is provided which comprises at least one of the above compounds of the present invention in a medium which is a liquid at ambient temperature. As the solvent used to dissolve the compound of the present invention, aromatic organic solvents having a boiling point from 80° C. to 250° C. such as benzene, dichlorobenzene, toluene, xylene, anisole, and tetralin and halogen type solvents such as dichloroethane are used either singly or in combinations of two or more.

A polymer compound having a high degree of polymerization may be further added to adjust to an ink viscosity suitable for the coating and printing process.

Examples of the polymer compound having a high degree of polymerization include a polystyrene, polycarbonate, polymethylmethacrylate, polyvinylnaphthalene, poly(9-vinylcarbazole), cyclic olefin copolymers such as ethylene-norbornane copolymer and ethylene-tetracyclododecene copolymer, poly(tetrahydrofuran), and polymers having a molecular weight of 100,000 to 2,000,000 and used for interlayer materials or light-emitting materials for polymer organic electroluminescent devices.

When the compound of the present invention is used as a light-emitting dopant, it is used in an amount of 0.5 to less than 50 wt % on a solid basis. When the amount is as low as less than 0.5 wt %, light emission is weak or energy is insufficiently transferred from a host material and there is therefore the case where the compound of the present invention insufficiently functions as a light-emitting dopant. When the amount exceeds 50 wt % on the other hand, there is the case where the intensity of fluorescence is reduced by concentration quenching. Therefore, the compound of the present invention is more preferably used in an amount of about 5 to 10 wt %.

Conversely, when the compound of the present invention is doped with 0.5 wt % or more of a light-emitting material having a molecular structure different from that of the compound of the present invention and used as a host material, it is used in an amount of 50 to 99.5 wt % on a solid basis. The ink composition of the present invention may contain a carrier transport material besides the above materials.

With regard to the ratio of the solid content to the solvent when the compound of the present invention is used, an appropriate ratio is selected from the range of about 0.1 to 30 wt % depending on the method for forming a film and solubility of the material.

When the compound of the present invention is contained as a light-emitting dopant in the above ink composition, the Eg of the host material is preferably larger than that of the dopant material to cause efficient energy transfer to the light-emitting dopant from the excited state of the host material to thereby obtain strong light emission from the light-emitting dopant material.

When the compound of the present invention is used as the light-emitting dopant, preferable examples of a low-molecular host material include 2,2'-bis(4-(2,4-bis(4-tert-butylphenyl)-1,3,5-triazine-6-yl)phenyl)-9,9'-spirobifluorene (hereinafter abbreviated as "BTrSBF"). However, polymer material may be also used as the host material, or the compound of the present invention is used as the host material and the compound of the present invention or other compound having a lower Eg may be used as the light-emitting dopant.

According to another embodiment of the present invention, there is provided a transfer donor base material for laser thermal transfer, laser sublimation transfer or the like which is fabricated by stacking a transfer layer containing the compound of the present invention on a substrate or sheet on which a layer is formed which absorbs light energy to generate heat.

Glass, a film or the like is used as the above substrate or sheet. A film containing the compound of the present invention in the transfer donor base material may be formed by application or vapor deposition of an ink composition containing the compound of the present invention.

When the thermal transfer donor base material is manufactured, a sheet base material the peelability of which is regulated by surface treatment is primarily used and polystyrene or polymer material having carrier transferability is added to the transfer layer to keep the shape of the film and to improve the adhesion to the display substrate when heated.

If a pattern of the light-absorbing layer formed on the donor sheet is irradiated with a laser or light beam of a light-emitting diode from the donor sheet base material side which is stuck to the display substrate, light energy is converted into heat, which is then conducted to the transfer layer through the light-reflecting layer laminated on the photo-absorption layer, whereby the transfer layer is softened and stuck to the display substrate. Then, the donor sheet is peeled off, thereby making it possible to form the pattern of the transfer layer corresponding to the photo-irradiation pattern.

As the compound of the present invention and the composition of the heat generating layer between the layer containing the compound of the present invention and the substrate, an appropriate material may be selected from materials which absorb light corresponding to the wavelength of a heating light source to generate heat, and a carbon type material, or metal oxide such as chromium type oxide or molybdenum type oxide may be used.

According to another embodiment of the present invention, a light-emitting device is provided which comprises a solid or liquid light-emitting layer containing a light-emitting material in at least one layer between electrodes facing each other or among layers formed between the positive electrode and negative electrode, and comprises at least one layer containing the compound of the present invention which is formed between the electrodes facing each other or between the positive electrode and negative electrode.

As an example such a light-emitting device, the case of fabricating an organic electroluminescent device provided with a solid light-emitting layer will be explained with reference to FIG. 1.

As a basic structure example of the organic electroluminescent device, the case of a structure provided with a positive electrode 2, a hole injection transport layer 3, an electron block hole transport layer 4, a light-emitting layer 5, a hole block electron transport layer 6, an electron injection transport layer 7, and a negative electrode 8 formed on a substrate 1 in this order will be explained.

Here, the hole injection transport layer 3 may structurally be constituted of two layers; a hole injection layer (not shown) arranged in contact with the positive electrode 2 and a hole transport layer (not shown), or constituted of one layer by combining the hole injection transport layer 3 and the electron block hole transport layer 4. Further, the hole block electron transport layer 6 may be combined with the electron injection transport layer 7 as one layer or the hole injection transport layer 3 may be constituted of only one of these transport layers.

A structure is allowed in which when holes are dominant in the carrier balance between injected holes and electrons, the electron block hole transport layer 4 is not used whereas when electrons are dominant in the carrier balance between injected holes and electrons, the hole block electron transport layer 6 is not used. It is preferable to adopt a structure in which hole carriers and electron carriers are balanced as equally as possible and hole and electron carriers are not accumulated at a local interface to suppress change in the chromaticity of EL light emission and to improve luminous efficiency and luminance life.

Because an organic electroluminescent device is easily deteriorated by water and oxygen, a passivation layer 9 which is made of an inorganic film and has high steam or oxygen barrier characteristics is formed on the device and further, a seal plate 11 to which a drying agent sheet 10 is applied according to the need is bonded by an adhesive material 12 having high oxygen and steam barrier characteristics in an inert gas atmosphere to provide a seal.

When the organic electroluminescent device is operated to emit light, the positive electrode 2 is connected to the anode of a power source 14 and a negative electrode terminal part 13 is connected to the cathode of the power source 14 respectively through a wire 15 to apply a DC voltage, allowing the organic electroluminescent device to emit light. When an AC voltage is applied, the organic electroluminescent device emits light while a positive voltage is applied to the positive electrode 2 and a negative voltage is applied to the negative electrode terminal part 13.

Hereinafter, the following explanations are furnished as to the case of first forming the positive electrode on the substrate.

As the substrate 1, a transparent glass plate superior in insulation ability and gas barrier characteristics is usually used. There is the case where a plastic film or a flexible substrate fabricated by insulation-coating a metal foil such as a stainless foil is used. There is also the case where a silicon substrate formed with a fine drive circuit or a sapphire substrate having excellent heat-radiation characteristics is used.

When a non-transparent substrate is used, light can be extracted by forming a counter electrode of an electrode on the substrate from a light-transmitting material.

As the positive electrode 2, a transparent conductive film of ITO (indium-tin complex oxide), IZO (indium-zinc complex oxide), or the like, highly electroconductive semitransparent metal thin film made of gold or platinum, or polythiophene type or polyaniline type polymer film having high electroconductivity is used.

General transparent electroconductive films such as ITO to be used for the positive electrode each have an Ip of about 5 eV and many blue light-emitting materials having a large Eg each have an Ip of about 6 eV. Therefore, when holes are injected directly into the light-emitting layer from the transparent electroconductive film, Eg is about 1 eV. Because of this, the positive electrode is surface-treated or a hole injection transport layer is stacked to reduce the Eg, to improve the efficiency of injecting holes into the light-emitting layer from the positive electrode, and to improve the smoothness of the surface of the positive electrode.

As to the surface treatment of the positive electrode, the Ip of the surface of the electrode can be increased by, for example, plasma treatment using argon gas or oxygen gas, ultraviolet radiation ozone treatment, or surface treatment using a fluorine-type silane coupling agent.

The hole injection transport layer 3 is formed by stacking one or more layers having a thickness of about 0.5 to 100 nm on the positive electrode. As the hole injection material, organic or inorganic semiconductor materials each having an Ip or Ea of about 5 to 6 eV are used singly or in combinations of two or more.

When layers subsequent to the hole injection transport layer are formed by the wet film-forming method after the formation of the hole injection transport layer, it is necessary that the hole injection transport layer be not dissolved by an organic solvent used in the formation of the layers subsequent to the hole injection transport layer. Because of this, films which are not dissolved in a solvent such as toluene or xylene, for example, a film of a complex of aqueous poly(3,4-ethylenedioxythiophene) and polystyrenesulfonic acid (abbreviated as "PEDOT:PSS"), and a coating film made from an aqueous dispersion solution of a polyaniline type electroconductive polymer material are widely used to also serve to smooth the surface of the electrode.

Other than the above, for example, a vapor deposition film of an organic pigment type such as copper phthalocyanine sparingly soluble in a toluene type organic solvent, or a vapor deposition film of a material having an Ea value between the Ips of the positive electrode and light-emitting layer such as hexadecafluorocopperphthalocyanine (having an Ea of about 5.4 eV) may be utilized.

Further, a film formed by the vacuum film forming method such as vacuum deposition, ion plating, or sputtering using an n-type inorganic semiconductor such as titanium oxide, molybdenum oxide, vanadium oxide, tungsten oxide, and nickel oxide or a film formed by the sol gel method may be utilized.

When layers formed after the formation of the hole injection transport layer are stacked by vapor deposition, a film soluble in an organic solvent may be formed by coating to form the hole injection transport layer.

For example, a vapor deposition film or coating film of an aromatic tertiary amine compound such as a star burst type, for example, 4,4',4"-tris[2-naphthyl(phenylamino)]triphenyl-amine, which has high hole transportability and high film forming ability may be also used. Moreover, these aromatic tertiary amine compounds may be doped with an acceptor such as 2,3,5,6-tetrafluoro-7,7,8,8-tetracyanoquinodimethane (abbreviated as "F4-TCNQ", Ea 5.24 eV), or 2-(6-dicyanomethylene-1,3,4,5,7,8-hexafluoro-6H-naphthalene-ylidene)malononitrile, or a Lewis acid such as tetraphenylantimony bromide and $FeCl_3$, to use a film more reduced in resistance.

When layers formed after the formation of the hole injection transport layer are stacked by vapor deposition, the compound of the present invention may be utilized because the layer is not dissolved in a solvent also in the case of using the compound of the present invention in the hole injection transport layer. For example, a material which can be deposited and has a molecular weight of 1300 or less among the compounds of the present invention and an electroconductive oxide material having an Ip of about 5.8 eV such as titanium oxide, molybdenum oxide, and tungsten oxide codeposit to form a hole injection transport layer.

When layers subsequent to the hole injection transport layer are formed by the wet film-forming method after the formation of the hole injection transport layer, there is the case where the compound of the present invention may be used in the hole injection transport layer in the case where a solvent is used in which the compound of the present invention is sparingly soluble or in the case where the compound of the present invention as shown by the compound 30 which has no substituent such as an alkyl group on the ring is used to codeposit with an electroconductive oxide material.

The electron block hole transport layer 4 is formed in a thickness of about 5 to 30 nm between the hole injection transport layer 3 and the light-emitting layer 5 and has the function of promoting the transport of holes to the light-emitting layer 5 from the positive electrode 2 and also has the function of preventing electrons injected into the light-emitting layer 5 from leaking into the positive electrode. As the electron block hole transport layer 4, a vapor deposition film of a low molecule including an aromatic tertiary amine having high hole transport ability or a film made of a crosslinkable polymer hole transport material which can be made to be insoluble in a solvent is preferably used.

The Ip of the electron block hole transport layer is preferably a value between the Ip of the hole injection transport layer and the Ip of the light-emitting layer and the difference in Ip between the hole injection transport layer and the light-emitting layer is preferably less than about 0.3 eV to prevent holes from accumulating at the interface of the electron block hole transport layer and the light-emitting layer. Further, as to the Ea of the electron block hole transport layer, a material having an Ea value lower by 0.3 eV than the Ea of the light-emitting layer is preferably used to confine electrons within the light-emitting layer. However, even if the electron block hole transport layer has the same Ea as the light-emitting layer, it may be used as the electron block hole transport layer when a material having hole mobility higher than electron mobility is used in the electron block hole transport layer. Further, a material having electron mobility made to be lower than hole mobility by adding a dopant which serves as an electron trap may also be used.

Further, when a phosphorescent material is used for the light-emitting layer, a material which has a minimum excited triplet level larger than that of the phosphorescent material and hence has a large Eg is used to prevent light quenching caused by the electron block hole transport layer in contact with the light-emitting layer.

When layers including the light-emitting layer stacked subsequent to the electron block hole transport layer are stacked by vapor deposition, a solvent-soluble material may be used as the electron block hole transport layer. In this case, the compound of the present invention from which the electroconductive oxide used in the compound of the present invention which is used for the hole injection transport layer is eliminated may be formed as a film by coating or vapor deposition.

The light-emitting layer 5 is formed as a film containing a fluorescent or phosphorescent light-emitting material in a thickness of about 5 to 100 nm on the hole transport layer. The light-emitting layer 5 is formed either of a single material or of a host material doped with a light-emitting dopant material. When the light-emitting layer 5 is formed by doping, this is more preferable because the excimer light emission and concentration quenching of the light-emitting dopant are suppressed, which improves the luminous intensity.

In the light-emitting layer, the compound of the present invention may be used, and further, known materials having various EL light-emitting colors such as red, blue, green and white may be used either singly or by doping a host material therewith. For example, low-molecular weight or polymer fluorescent light emitting materials such as anthracene derivatives, benzeneanthracene derivatives, dibenzoanthracene derivatives, styryl derivatives, carbazole derivatives, fluorene oligomers, polyfluorene type copolymers and polyphenoxazine copolymers, and phosphorescent light-emitting complexes containing heavy atoms such as iridium, platinum, osmium, and rhenium may be used.

Among the compound examples of the present invention, the anthracene derivative compounds represented by compounds 1 to 7, 14 to 16, 20 to 27, and 30 and anthracene derivative compounds represented by the formulae (4) to (7) are preferable as blue light-emitting materials and may also be used as host materials for blue, green or red light-emitting layer.

Further, the benzoanthracene derivative compounds represented by the compounds 8 and 28 are preferable as green light-emitting materials and may also be used as host materials for green or red light-emitting layer.

Further, the dibenzoanthracene derivative compounds represented by the compounds 9 to 12 and 29 of the present invention are preferable as orange to red light-emitting materials and may also be used as host materials for red to far-infrared light-emitting layer.

The host material in the light-emitting layer preferably has an Eg larger than the light-emitting dopant material and the spectral overlap of the emission spectrum of the host material and the absorption spectrum of the light-emitting dopant is preferably larger.

Further, with regard to the host material, a host material having the same or higher Ip and the same or lower Ea than the light-emitting dopant is used, thereby making it possible to improve the hole/electron trapping probability of the light-emitting dopant molecule. The host material for a blue light-emitting layer is preferably a material which does not absorb blue-light EL emission having high color purity and a wavelength of about 400 to 450 nm and is required to have an Eg of about 3 eV or more.

With regard to specific examples of the blue color host material, 2,2'-bis(4-(2,4-bis(4-tert-butylphenyl)-1,3,5-triazine-6-yl)phenyl)-9,9'-spirofluorene (hereinafter abbreviated as "BTrSBF") represented by the compound 31 or the like may be used.

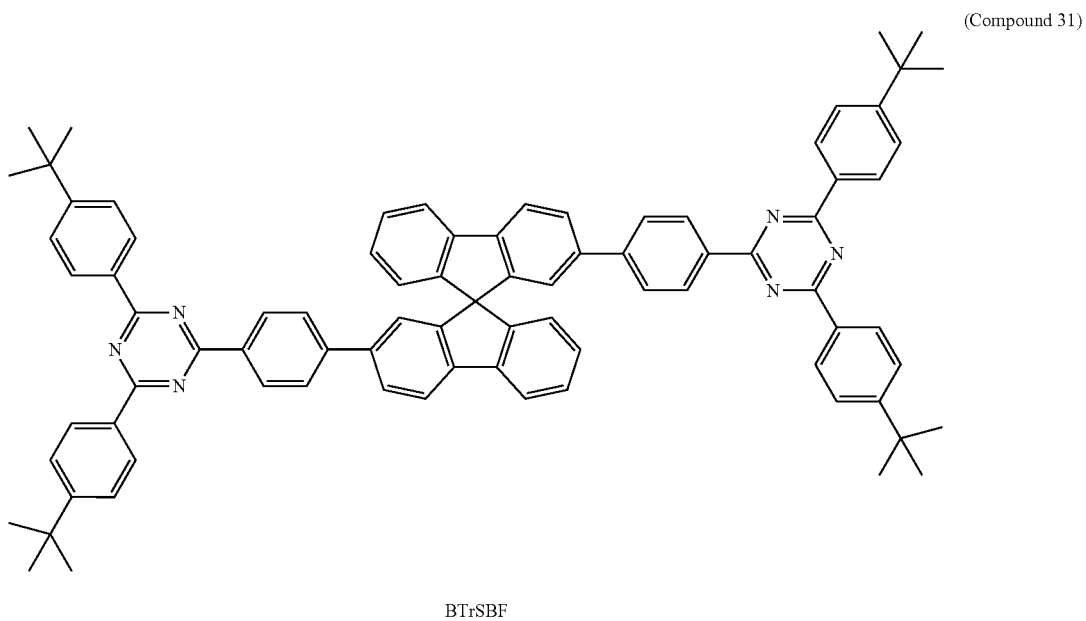 [SMILES: CC(C)(C)c1ccc(-c2nc(-c3ccc(-c4ccc5c(c4)C4(c6ccccc6-5)c5ccccc5-c5ccc(-c6ccc(-c7nc(-c8ccc(C(C)(C)C)cc8)nc(-c8ccc(C(C)(C)C)cc8)n7)cc6)cc54)cc3)nc(-c3ccc(C(C)(C)C)cc3)n2)cc1]

(Compound 31)

BTrSBF

Further, materials used for the electron block hole transport layer or hole block electron transport layer which will be explained later may be used as the host material for the light-emitting layer.

The hole transport material and electron transport material may be formulated in the light-emitting layer to adjust the balance between electron transportability and hole transportability.

Then, on the light-emitting layer 5, one or both of the hole block electron transport layer 6 and electron injection transport layer 7 are respectively formed in a thickness of about 5 to 50 nm on the negative electrode side in contact with the light-emitting layer.

The hole block electron transport layer 6 can prevent holes from leaking into the negative electrode and excitons from diffusing into the negative electrode to thereby improve luminous efficiency when the light-emitting layer 5 has a hole transporting ability higher than an electron transporting ability so that the light-emitting region is shifted to the vicinity of the negative electrode.

The material of the hole block electron transport layer is preferably a material which has an Ip larger by 0.3 eV or more and an Ea smaller by about 0.1 eV than the light-emitting material, and has a sufficiently large Eg so that it does not absorb EL emission from the light-emitting layer. In the case of a blue color emitting device, a material having an Eg of 3 eV or more is preferable.

The electron injection transport layer 7 may be stacked on the hole block electron transport layer 6 or the light-emitting layer 5.

The electron injection transport layer 7 is formed in a thickness of about 0.5 to 50 nm to lower the energy barrier and electric resistance to electron injection into the hole block electron transport layer 6 or the light-emitting layer 5 from the negative electrode 8. The electron injection transport layer is more reduced in resistance by doping, so that an organic electroluminescent device can be driven at a lower voltage. An alkali metal, alkali earth metal, or rare earth metal such as Cs, Na, Li, and Ba each having lower ionization energy, or compounds containing these metals are doped or mixed in the electron injection transport layer by, for example, co-evaporation to give electrons to a host compound thereby anionizing the host compound, whereby carrier density can be increased to lower the resistance.

As to specific examples of the materials for the hole block electron transport layer 6 and electron injection transport layer 7, 1,10-phenanthroline derivatives such as bathocuproine or bathophenanthroline, benzimidazole derivatives such as 1,3,5-tris(N-phenylbenzimidazole-2-yl)benzene (abbreviated as "TPBI"), metal complexes such as a bis(10-benzoquinolinolate)beryllium complex, 8-hydroxyquinoline Al complex, and bis(2-methyl-8-quinolinolate)-4-phenylphenolatealuminum, and nitrogen-containing heteroaryl groups having high electron transport ability such as 4,4'-biscarbazolbiphenyl and tris[3-(3-pyridyl)mesityl]borane may be used.

Other than the above compounds, aromatic silane compounds and aromatic phosphine compounds such as phenyl-di(1-pyrenyl)phosphine oxide, biphenyl-4,4'-diylbis(diphenylphosphine oxide), 2,2'-bis[di(p-tolyl)phosphinoyl]-1,1'-binaphthalene may also be used.

When the compound of the present invention is used for the hole block electron transport layer and electron injection transport layer, a proper compound may be selected from compounds represented by the compounds 14, 17, 18, 19, and 23, compounds, such as the compounds represented by the formulae (5) to (7), which have a nitrogen-containing heteroaryl group as a substituent, or compounds, such as the compound 16, which are increased in Ip and Ea by substitution with fluorine, according to the energy level of the light-emitting layer, and used to form a film by vacuum deposition or coating.

As the negative electrode 8, a vapor deposition film of a metal such as Al and Ag which usually have a low resistance and a high optical reflectance is used. When a light transmittable negative electrode is formed, a transparent electrode material and the like are stacked on a metal negative electrode about 10 nm or less in thickness.

A layer made from an alkali metal or alkali earth metal such as Li, Ba, or Cs having a low work function of 3 eV or less and rare earth metal such as Yb or a compound of each of these metals is preferably formed in a thickness of several nanomicrons (nm) or less at the interface between the negative electrode and the organic layer. Concerning this, if water is present, this poses the problem that a local battery is formed, causing corrosion easily. Therefore, non-light emitting spots are easily generated and this is the reason why the system is firmly sealed.

There is also the case where an ionic liquid or a salt is added to the negative electrode or the organic layer at the interface of the negative electrode to form an electric double layer at the interface of the negative electrode to thereby reduce the electron injection barrier.

With regard to mass-production technologies concerning a method of forming each organic layer of the EL light-emitting device, the vacuum deposition method using a low-molecular organic material superior in thickness controllability and uniformity of the thin film is usually used. However, when one coating layer constituted of a polymer or coating type low molecule having high step coverage and high smoothing effect is formed, this produces such an effect that the device scarcely develops short circuits and it is therefore advantageous to adopt a combined process of the coating method and vacuum deposition method in applications such as large-size light emission displays and illumination.

The following explanations are furnished as to the case of manufacturing an electrochemiluminescence type organic electroluminescent device provided with a liquid light-emitting layer containing the compound of the present invention which is highly soluble in an organic solvent.

The compound of the present invention is dissolved in a concentration of 5 to 10 wt % in an organic solvent such as orthodichlorobenzene or toluene, and about 0.1 wt % of a support electrolyte such as $LiCF_3SO_3$ is added or 1,2-diphenoxyethane as a positive ion conductive assist dopant is added to the above solution to prepare a light-emitting layer solution.

Using a substrate which has a permeability of light at least on one side, the light-emitting layer solution is interposed between electrode plates facing each other to fabricate a device having a gap of several microns or less, or the light-emitting layer solution is interposed between a substrate formed with a comb-shaped electrode and a cover glass facing the substrate to fabricate an organic electroluminescent device.

These organic electroluminescent devices can be each made to electrolytically emit light by applying a DC or AC continuous or pulse-like current to the light-emitting layer.

EXAMPLES

Examples of the present invention will be explained.

Example 1

Synthesis of 9,10-bis{4-[2,4-bis(4-tert-butylphenyl)-1,3,5-triazine-6-yl]biphenyl-2'-yl}anthracene (Compound 1)

Synthetic Example of an Intermediate 1

Synthesis of 2,4-bis(4-tert-butylphenyl)-6-(4-bromophenyl)-1,3,5-triazine (intermediate A)

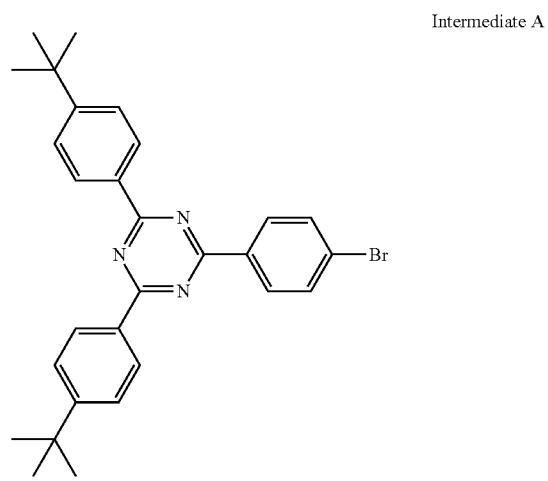 [SMILES: CC(C)(C)c1ccc(-c2nc(-c3ccc(Br)cc3)nc(-c3ccc(C(C)(C)C)cc3)n2)cc1]

Intermediate A

In an argon atmosphere, 5.0 g (0.023 mol) of 4-tert-butylbenzonitrile and 7.6 g (0.048 mol) of 4-bromobenzoic acid were dissolved in 300 ml of methylene chloride. The solution was cooled to 0° C. 6.8 g (0.023 mol) of antimony pentachloride was added dropwise to the solution. The temperature of the solution was returned to ambient temperature and the solution was stirred for 1 hr, followed by refluxing with stirring for 13 hr to react.

After the reaction had finished, the solvent was distilled to obtain a yellow solid residue. This solid residue was milled and aqueous 28% ammonia cooled to 0° C. was added to the milled solid residue. Then, the temperature of the mixture was returned to ambient temperature and the mixture was stirred for 2 hr. The precipitated white solid was collected by filtration and was washed with water and then with methanol. After drying, the solid residue was purified by silica gel column chromatography using hexane-methylene chloride (1:1) as an eluent to obtain 6.98 g of 2,4-bis(4-tert-butylphenyl)-6-(4-bromophenyl)-1,3,5-triazine (yield: 61.2%).

$^1$H NMR (400 MHz, d-$CDCl_3$): δ 1.41 (s, 18H), 7.60 (d, J=8.5 Hz, 4H), 7.70 (d, J=8.7 Hz, 2H), 8.64 (J=8.7 Hz, 2H), 8.66 (d, J=8.5 Hz, 4H).

Synthetic Example of an Intermediate 2

Synthesis of 2,4-bis(4-tert-butylphenyl)-6-[4,4,5,5-tetramethyl-1,3,2-dioxaborane-2-yl]-phenyl]-1,3,5-triazine (intermediate B)

Intermediate B

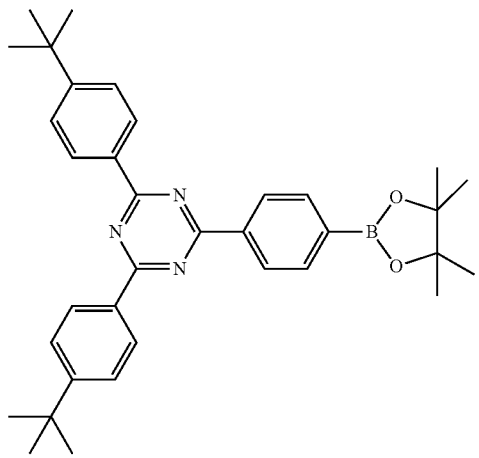

In an argon atmosphere, a mixture of 3.0 g (5.99 mmol) of 2,4-bis(4-tert-butylphenyl)-6-(4-bromophenyl)-1,3,5-triazine (intermediate A), 1.83 g (7.21 mmol) of bis(pinacolate)diborane, 1.77 g (18.04 mmol) of potassium acetate, and 68 ml of DMF was deoxidized at ambient temperature. Then, 0.48 g (0.60 mmol) of PdCl$_2$ (dppf) was added to the mixture, which was then stirred at 80 to 90° C. for 64 hr to react.

After the reaction was finished, DMF was distilled from the reaction mixture. The residue was extracted with methylene chloride, washed with water, and then, a solvent was distilled. The obtained residue was purified by silica gel column chromatography using hexane-methylene chloride (1:2) as an eluent to obtain 2.97 g of 2,4-bis(4-tert-butylphenyl)-6-[4-(4,4,5,5-tetranethyl-1,3,2-dioxaborane-2-yl)-phenyl]-1,3,5-triazine (yield: 90.8%).

$^1$H NMR (400 MHz, d-CDCl$_3$): δ 1.40 (s, 12H), 1.41 (s, 18H), 7.60 (d, J=8.5 Hz, 4H), 8.00 (d, J=8.0 Hz, 2H), 8.69 (d, J=8.5 Hz, 4H), 8.74 (d, J=8.0 Hz, 2H).

Synthetic Example of an Intermediate 3

Synthesis of 2,4-bis(4-tert-butylphenyl)-6-(2'-bromophenyl-4-yl)-1,3,5-triazine (intermediate C)

Intermediate C

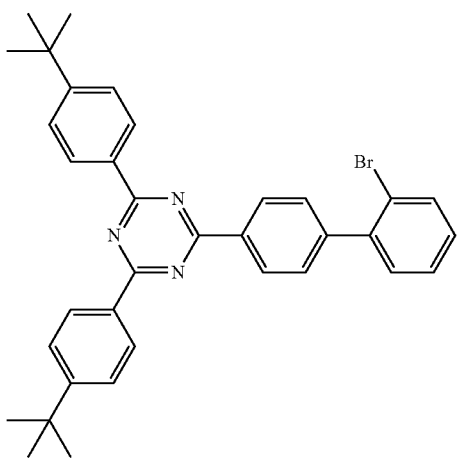

In an argon atmosphere, a mixture of 2.0 g (3.66 mmol) of 2,4-bis(4-tert-butylphenyl)-6-[4-(4,4,5,5-tetranethyl-1,3,2-dioxaborane-2-yl)-phenyl]-1,3,5-triazine (intermediate B), 3.0 g (2.89 mmol) of o-iodobromobenzene, 1.13 g (10.65 mmol) of sodium carbonate, 5 mL of water, and 50 mL of DMF was deoxidized at ambient temperature. Then, 0.41 g (0.36 mmol) of tetrakistriphenylphosphinepalladium (0) was added to the mixture, which was then stirred at 85° C. for 48 hr. After the reaction was finished, the reaction mixture was poured into water and was then extracted with methylene chloride. The extract was washed with water, dried using sodium sulfate anhydride, and then, a solvent was distilled. The residue was purified by silica gel column chromatography using hexane/methylene chloride (8:1) as an eluent to obtain 2.06 g of 2,4-bis(4-tert-butylphenyl)-6-(2'-bromobiphenyl-4-yl)-1,3,5-triazine (yield: 97.6%).

$^1$H NMR (400 MHz, d-CDCl$_3$): δ 1.41 (s, 18H), 7.34 (br, 1H), 7.42 (d, J=4.1 Hz, 2H), 7.57-7.66 (m, 6H), 7.72 (d, J=8.7 Hz, 1H), 8.71 (dd, J=8.7 Hz, 1.8 Hz, 4H), 8.85 (dd, J=8.2 Hz, 1.8 Hz, 2H).

Synthetic Example of an Intermediate 4

Synthesis of 9,10-bis(4,4,5,5-tetramethyl-1,3,2-dioxaborane-2-yl)anthracene (intermediate D)

Intermediate D

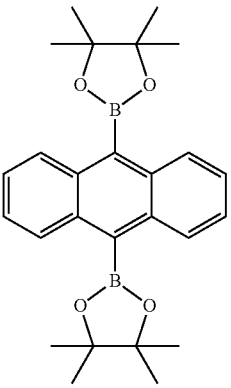

In an argon atmosphere, 6.0 g (17.86 mmol) of 9,10-dibromoanthracene was dissolved in 200 mL of tetrahydrofuran, which was then cooled to −70° C. Then, a solution of 1.6 M n-butyllithium in 23.4 mL (37.5 mmol) of hexane was added dropwise to the solution. Moreover, the resulting solution was stirred at the same temperature for 1 hr and then, 9.1 mL (44.65 mmol) of 2-isopropoxy-4,4',5-tetramethyl-1,3,2-dioxyboralon was added to the solution, which was then stirred overnight while the temperature of the solution was gradually returned to ambient temperature to react.

After the reaction had finished, the reaction mixture was poured into water, and the solution was extracted with methylene chloride. The extract was washed with saturated brine and then dried using sodium sulfate anhydride. Further, a solvent was distilled and the residue was purified by silica gel column chromatography using hexane/methylene chloride (1:1) as an eluent to obtain 1.85 g of 9,10-bis(4,4,5,5-tetramethyl-1,3,2-dioxaborane-2-yl)anthracene (yield: 24.1%).

$^1$H NMR (400 MHz, d-CDCl$_3$): δ 1.58 (s, 24H), 7.45 (dd, J=6.6 Hz, 3.2 Hz, 4H), 8.33 (dd, J=6.6 Hz, 3.2 Hz, 4H).

Synthetic Example 1

Synthesis of 9,10-bis{4-[2,4-bis(4-tert-butylphenyl)-1,3,5-triazine-6-yl]biphenyl-2'-yl}anthracene (Compound 1)

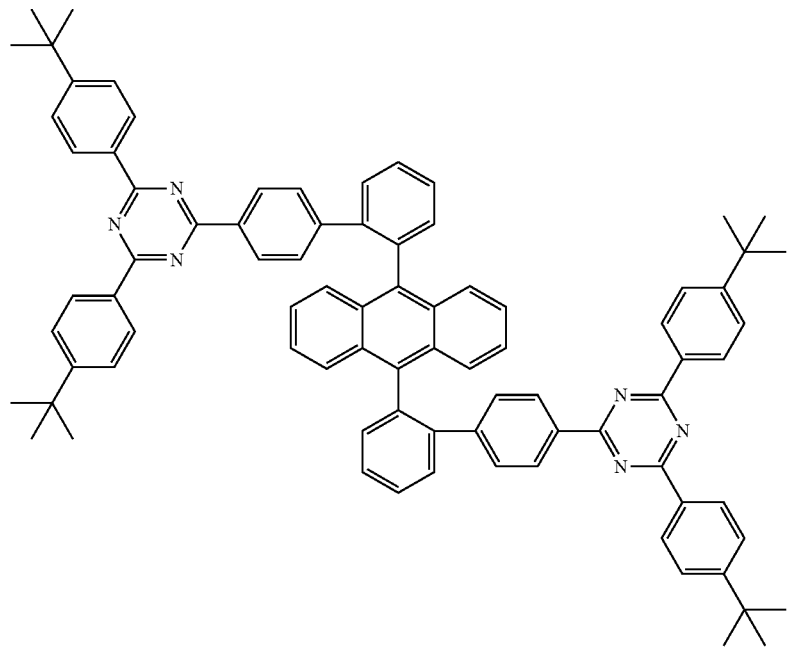

Compound 1

In an argon atmosphere, a mixture of 1.8 g (3.12 mmol) of 2,4-bis(4-tert-butylphenyl)-6-[2'-bromophenyl-4-yl]-1,3,5-triazine (intermediate C), 0.62 g (1.44 mmol) of 9,10-bis(4,4,5,5-tetramethyl-1,3,2-dioxaborane-2-yl)anthracene (intermediate D), 1.0 g (9.43 mmol) of sodium carbonate, 4.0 mL of water, and 40.0 mL of DMF was deoxidized at ambient temperature. 0.44 g (0.38 mmol) of tetrakistriphenylphosphinepalladium (0) was added to the mixture, which was then stirred at 85° C. for 24 hr to react.

After the reaction had finished, the reaction mixture was poured into water, which was then extracted with methylene chloride. Then, the extract was washed with water and dried by sodium sulfate anhydride. A solvent was distilled and a major component having a larger Rf value (Rf=0.36) in thin layer column chromatography (hereinafter abbreviated as "TLC") using hexane:methylene chloride (3:1) as an eluent was purified by silica gel column chromatography using hexane-methylene chloride (6:1) as an eluent and then, washed with warm acetone to obtain 0.33 g of 9,10-bis{4-[2,4-bis(4-tert-butylphenyl)-1,3,5-triazine-6-yl]biphenyl-2'-yl}anthracene.

The yield was 19.8% and the purity of HPLC was 99.6%.

HPLC analysis conditions were as follows: column: Mighthysil RP-18 GP 150-4.5 (5 μm) (reverse phase system), eluent: THF/$CH_3CN$=20/80, 1.0 ml/min, UV: 254 nm.

A main peak of 1169.86 obtained in ESI-Ms mass analysis coincided with the calculated value ($C_{84}H_{76}N_6$: 1169.54) of the target product.

A $^1H$ NMR chart (400 MHz, d-$CDCl_3$) of the isomer component (Rf=0.36) of the compound shown by the compound 1 of the present invention is shown in FIG. 2A. Further, FIG. 2B is an enlarged view of FIG. 2A.

δ 1.17 (s, 36H), 7.17 (d, J=8.5 Hz, 8H), 7.20 (dd, J=6.8 Hz, 3.2 Hz, 4H), 7.29 (d, J=8.5 Hz, 4H), 7.47 (dd, J=7.6 Hz, 1.4 Hz, 2H), 7.58 (dt, J=7.6 Hz, 1.4 Hz, 2H), 7.65-7.72 (m, 6H), 7.85 (dd, J=7.8 Hz, 0.9 Hz, 2H), 8.33 (d, J=8.5 Hz, 8H), 8.63 (d, J=8.5 Hz, 4H).

The characteristics of the compound 1 are shown below.

<Thermal Analysis>

The glass transition temperature (Tg), crystallization temperature (Tc), and melting point (Tm) of the compound 1 were measured by EXSTAR6000 Series DSC6200 manufactured by Seiko Instruments Inc., at a temperature rise rate of 20° C./min. In the first heatup, neither heat absorption nor heat generation was observed at the temperature range from ambient temperature to 300° C., and Tg at a temperature close to 300° C. to 330° C., in succession, Tc at a temperature close to 333° C. to 360° C., or an exothermic peak (peak temperature 351° C.) that was considered to be due to a transition from a Syn-configuration to an Anti-configuration produced by the rotation of two substituents at the ninth and tenth positions were shown. Tm was 493° C. to 513° C. (peak 504° C.).

<Solubility>

The compound 1 was dissolved with a concentration of 1.3 mg in 1 ml of toluene at ambient temperature and used as a light-emitting dopant for a blue light-emitting layer ink, which could be applied to form a film.

<Energy Level of the Compound 1>

A solution prepared by dissolving 1.3 mg of the compound 1 in 1 ml of toluene was applied to an ITO transparent electroconductive glass by spin coating to measure the ionization potential by a surface analyzer AC-1 manufactured by Riken Keiki Co., Ltd., to find that the ionization potential was 5.9 eV. The electron affinity obtained by subtracting the absorption-edge energy from the ionization potential was 2.9 eV.

<Fluorescent Spectrum>

Figure 3:
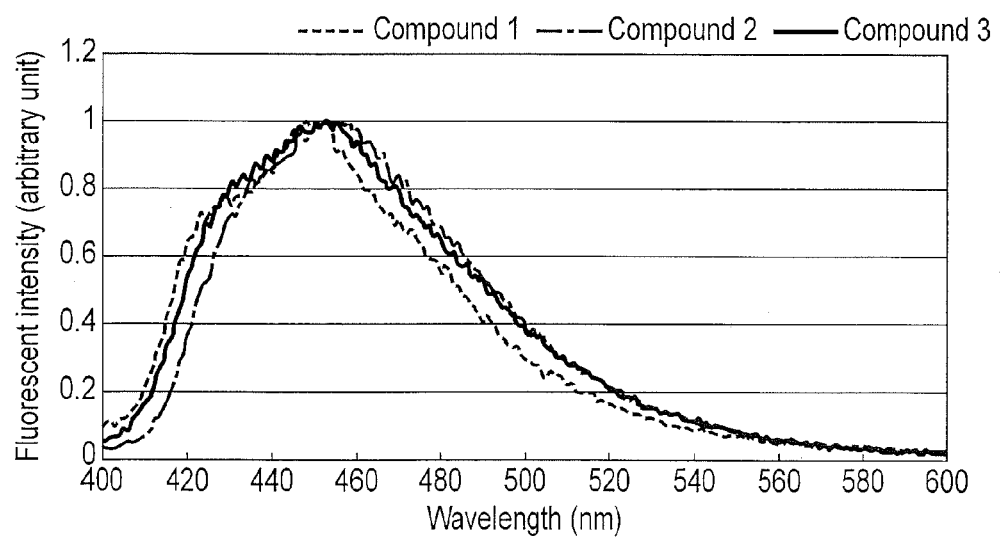
FIG. 3 shows fluorescent spectrums of compounds 1 to 3 according to examples of the present invention.

FIG. 3 shows the fluorescent spectrum of each spin coat film of the compounds 1 to 3 on a transparent electroconductive glass with an ITO film when it is measured by a fluorophotometer (trade name: RF-5300PC, manufactured by Shimadzu Corporation). The compound 1 exhibited a blue color having an excitation wavelength of 330 nm and a fluorescent peak wavelength of 448 nm.

Example 2

Synthesis of 2-methyl-9,10-bis{4-[2,4-bis(4-tert-butylphenyl)-1,3,5-triazine-6-yl]biphenyl-2'-yl}anthracene (Compound 2)

Synthetic Example of an Intermediate 5

Synthesis of 9,10-bis(2-methoxyphenyl)-2-methyl-9,10-dihydroanthracene-9,10-diol (intermediate E)

Intermediate E

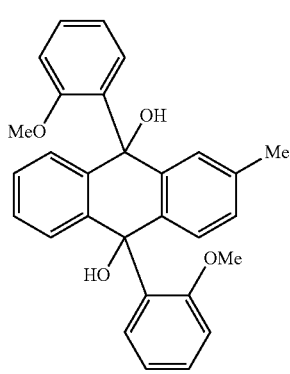

In an argon atmosphere, 25.0 g (0.134 mol) of 2-bromoanisole was dissolved in 200 ml of ether and the solution was cooled to 0° C. Then, 91.9 mL (0.147 mol) of a 1.6 M n-butyllithium/hexane solution was added dropwise to the solution. The mixture was aged at 0° C. for 2 hr, and a suspension constituted of 14.85 g (0.067 mol) and 500 mL of ether and 120 mL of THF were added one by one. Then, the mixture was reacted at ambient temperature overnight with stirring.

After the reaction was finished, the reaction mixture was poured into water and extracted with methylene chloride. The organic layer was isolated, washed with an aqueous saturated ammonium chloride solution, and dried with sodium sulfate anhydride. A solvent was distilled and the obtained brown solid was washed with hexane and then with ether, followed by drying under reduced pressure to obtain 20.9 g of 9,10-bis(2-methoxyphenyl)-2-methyl-9,10-dihydroanthracene-9,10-diol (yield: 71.3%).

A molecular weight of 405 (de-OH during measurement of M+−34 to Ms) was obtained in DI-mass analysis, which coincided with the calculated value 438.51 of $C_{29}H_{26}O_4$.

Synthetic Example of an Intermediate 6

Synthesis of 9,10-bis(2-methoxyphenyl)-2-methylanthracene (intermediate F)

Intermediate F

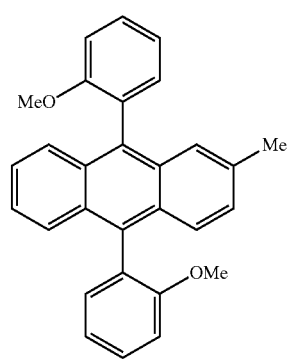

A mixture of 15.0 g (0.034 mol) of 9,10-bis(2-methoxyphenyl)-2-methyl-9,10-dihydroanthracene-9,10-diol (intermediate E), 400 mL of acetic acid, 14.2 g (0.086 mol) of potassium iodide, and 4.55 g (0.043 mol) of sodium phosphinate monohydrate $NaPH_2O_2$ was refluxed with stirring for 9 hr until the raw material disappeared.

After the reaction had finished, the reaction mixture was poured into water and the precipitated yellow deposit was extracted with methylene chloride. The organic layer was isolated, washed with an aqueous sodium carbonate solution and then with water, and dried with sodium sulfate anhydride. A solvent was distilled and the obtained residue was purified by silica gel chromatography using hexane-methylene chloride (3/1 to 1/1) as an eluent to obtain two atropisomers (syn-configuration and anti-configuration) attributable to the rotation of angle of an orthomethoxyphenyl group of 9,10-bis(2-methoxyphenyl)-2-methylanthracene. However, when the isolated carbon is decomposed by an ether in the subsequent step, the substituent is easily rotated to obtain a mixture of atropisomers. Therefore, the isolated compounds are used together for the following reaction.

Isomer-1 (spot of Rf 0.51 when developed using hexane: methylene chloride=1:1 in TLC)

Amount of the product: 5.39 g (yield: 38.9%)

In DI-Mass analysis, a main peak of 405 (M+) was obtained, which coincided with the calculated value 404.50 of $C_{29}H_{24}O_2$.

$^1$H NMR (400 MHz, d-CDCl$_3$): δ 2.38 (s, 3H), 3.65 (s, 3H), 3.66 (s, 3H), 7.12 to 7.21 (m, 4H), 7.25 to 7.29 (m, 3H→overlaps with solvent CHCl$_3$), 7.33-7.36 (m, 3H), 7.52-7.61 (m, 5H).

Isomer-2 (spot of Rf 0.31 in TLC)

Amount of the product: 4.46 g (yield: 32.2%)

In DI-Mass analysis, a main peak of 405 (M+) was obtained, which coincided with the calculated value 404.50 of $C_{29}H_{24}O_2$.

$^1$H NMR (400 MHz, d-CDCl$_3$): δ 2.38 (s, 3H), 3.65 (s, 3H), 3.66 (s, 3H), 7.12 to 7.20 (m, 4H), 7.25 to 7.30 (m, 5H→overlaps with solvent CHCl$_3$), 7.36 (br, 1H), 7.51-7.61 (m, 5H).

Synthetic Example of an Intermediate 7

Synthesis of 9,10-bis(2-hydroxyphenyl)-2-methylanthracene (intermediate G)

Intermediate G

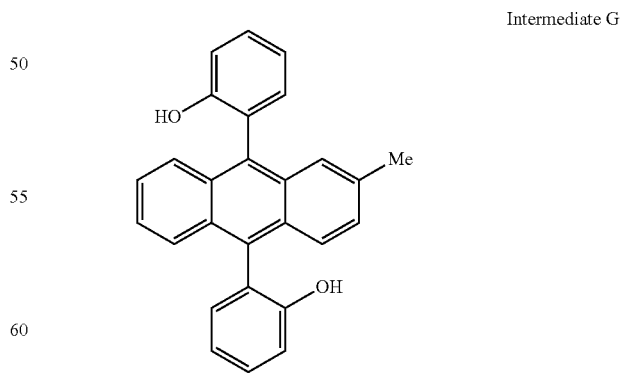

In an argon atmosphere, a solution of 2.21 g (5.46 mmol) of 9,10-bis(2-methoxyphenyl)-2-methylanthracene in 40 mL of methylene chloride was ice-cooled, and then, a solution of 1.20 mL (12.49 mmol) of boron tribromide BBr$_3$ in 6.0 mL of methylene chloride was added dropwise to the above solution. The mixture was stirred overnight to react while the temperature was gradually returned to ambient temperature.

After it was confirmed by TLC that the raw material had disappeared, the reaction mixture was poured into ice-water, which was neutralized by sodium carbonate. The reaction mixture was then extracted with methylene chloride. The organic layer was isolated, washed with water and then with saturated brine, and dried with sodium sulfate anhydride. A solvent was distilled to obtain 2.0 g (5.31 mmol) of a crude product of 9,10-bis(2-hydroxyphenyl)-2-methylanthracene (yield: 97%).

In DI-Mass analysis, a main peak of 377 (M+) was obtained, which coincided with the calculated value 376.45 of $C_{27}H_{20}O_2$.

$^1$H NMR (400 MHz, d-CDCl$_3$): δ 2.43 (s, 3H), 4.63 (br, 2H), 7.17-7.22 (m, 4H), 7.29 (d, J=1.8 Hz, 1H), 7.30-7.33 (m, 2H), 7.39-7.42 (m, 2H), 7.47 (br, 1H), 7.47-7.54 (m, 2H), 7.66 (d, J=8.7 Hz, 1H), 7.69-7.74 (m, 2H).

Synthetic Example of an Intermediate 8

Synthesis of 2,2-(2-methylanthracene-9,10-diyl)bis (2,1-phenylene)bis(trifluoromethanesulfonate) (intermediate H)

Intermediate H

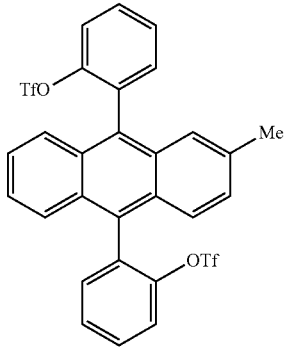

A solution consisting of 2.0 g (5.31 mmol) of 9,10-bis(2-hydroxyphenyl)-2-methylanthracene (intermediate G), 50 mL of pyridine, and 250 mL of methylene chloride was ice-cooled, and then, 2.6 mL (15.96 mmol) of trifluoromethanesulfonic acid anhydride was added to the above solution. The mixture was stirred overnight to react while the temperature was gradually returned to ambient temperature.

After it was confirmed by TLC that the raw material had disappeared, the reaction mixture was poured into an aqueous ammonium chloride solution. The reaction mixture was then extracted with methylene chloride. The organic layer was washed with saturated brine, and dried with sodium sulfate anhydride. A solvent was distilled and the obtained residue was purified by silica gel column chromatography using hexane-methylene chloride (2/1) as an eluent to obtain 2.75 g of 2,2-(2-methylanthracene-9,10-diyl)bis(2,1-phenylene)bis (trifluoromethanesulfonate) (yield: 80.6%).

In DI-Mass analysis, a main peak of 640 (M+) was obtained, which coincided with the calculated value 640.57 of $C_{29}H_{18}F_6O_6S_2$.

$^1$H NMR (400 MHz, d-CDCl$_3$): δ 2.42 (s, 3H), 7.22-7.26 (m, 1H), 7.29 (br, 1H), 7.34-7.40 (m, 2H), 7.46-7.72 (m, 11H).

Synthetic Example 2

Synthesis of 2-methyl-9,10-bis{4-[2,4-bis(4-tert-butylphenyl)-1,3,5-triazine-6-yl]biphenyl-2'-yl}-anthracene (Compound 2)

Compound 2

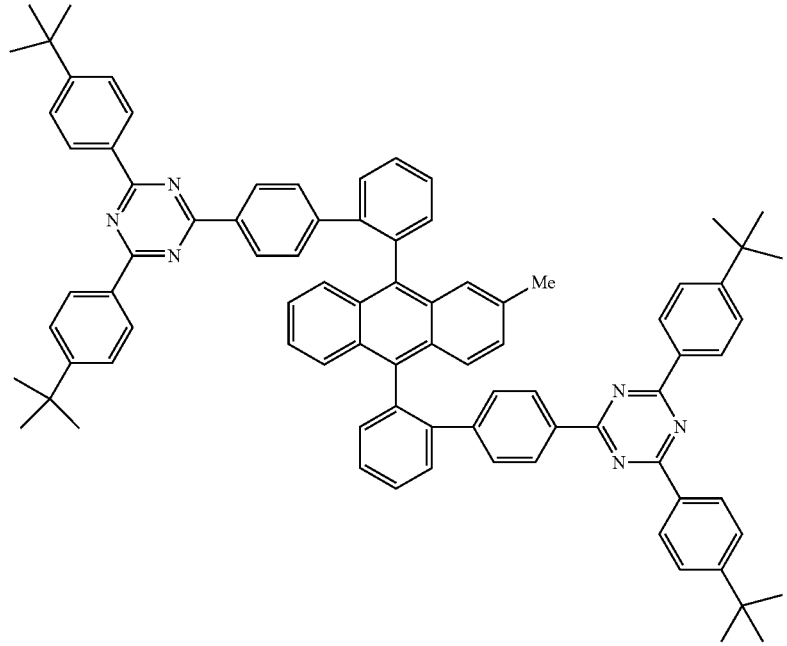

In an argon atmosphere, a mixture of 1.0 g (1.56 mmol) of 2,4-bis(4-tert-butylphenyl)-6-[4-(4,4,5,5-tetramethyl-1,3,2-dioxaborane-2-yl)-phenyl]-1,3,5-triazine, 1.96 g (3.59 mmol) of 2,2-(2-methylanthracene-9,10-diyl)bis(2,1-phenylene)bis(trifluoromethane sulfonate), 3.5 mL (7.18 mmol) of an aqueous 2 M sodium carbonate solution, and 60 mL of DMF was deoxidized at ambient temperature. Then, 0.36 g (0.31 mmol) of tetrakistriphenylphosphinepalladium (0) Pd (PPh$_3$)$_4$ was added to the mixture, which was then stirred at 85° C. to 90° C. for 48 hr to react.

After the reaction had finished, the reaction mixture was poured into water, which was then extracted with an ether. The organic layer was isolated, washed with water, and then a solvent was distilled. The obtained residue was purified by silica gel chromatography using hexane-methylene chloride (8/1 to 1/1) as an eluent to obtain two atropisomers (retention times were 18.2 min and 25.7 min in HPLC analysis) attributable to the rotation of angle of the substituents at ninth and tenth positions of 2-methyl-9,10-bis{4-[2,4-bis(4-tert-butylphenyl)-1,3,5-triazine-6-yl]biphenyl-2'-yl}-anthracene.

Isomer component 1 (retention time: 18.2 min in HPLC analysis, Rf=0.11 in TLC when developed using hexane:ether=100:1)

Purity of HPLC: 100.0%. Amount of the product: 0.23 g (yield: 12.4%).

Conditions of HPLC (column: Mightysil RP-18 GP 150-4.6 (particle diameter: 5 μm) UV: 254 nm, eluent: CH$_3$CN/THF (80/20)).

Peak molecular weights of 1206.97 (M$^+$+Na) and 1222.91 (M$^+$+K) obtained in ESI-Ms mass analysis coincided with the calculated value (C$_{85}$H$_{78}$N$_6$: 1183.57) of the target product.

Figure 4A:
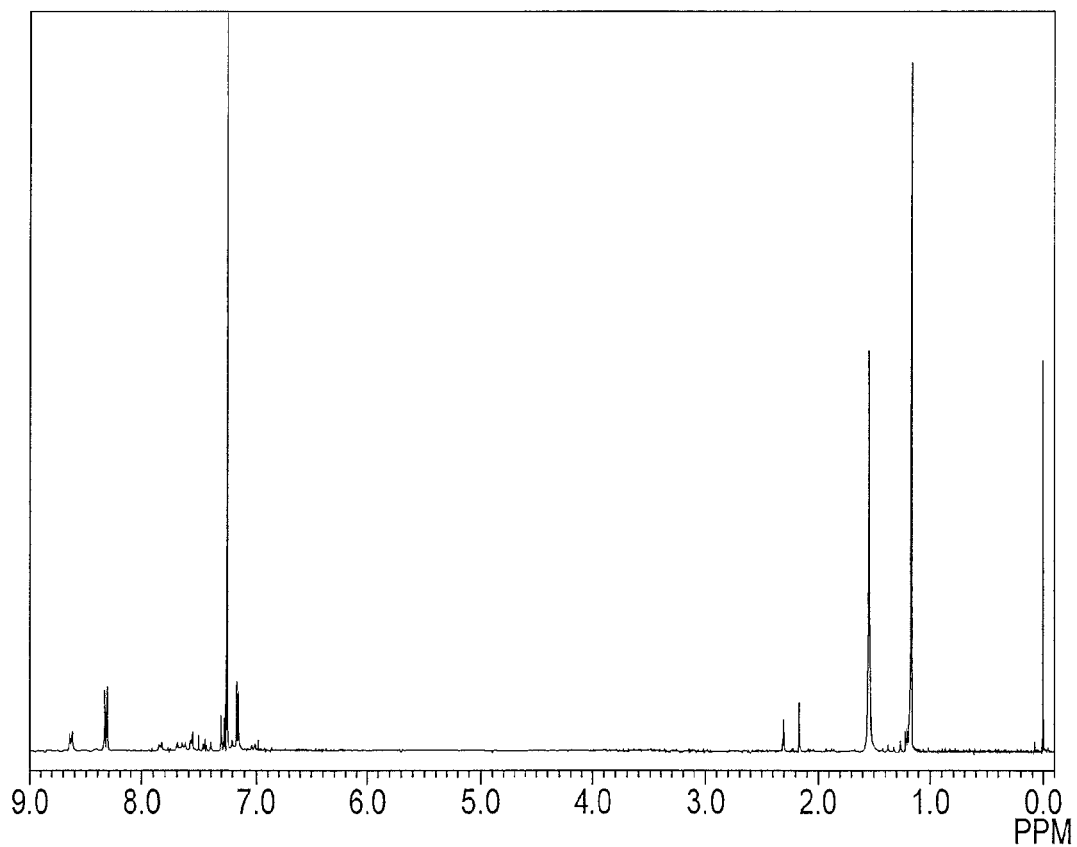
FIG. 4A is a $^1$H-NMR chart of an isomer component 1 of a compound 2 according to an example of the present invention.
Figure 4B:
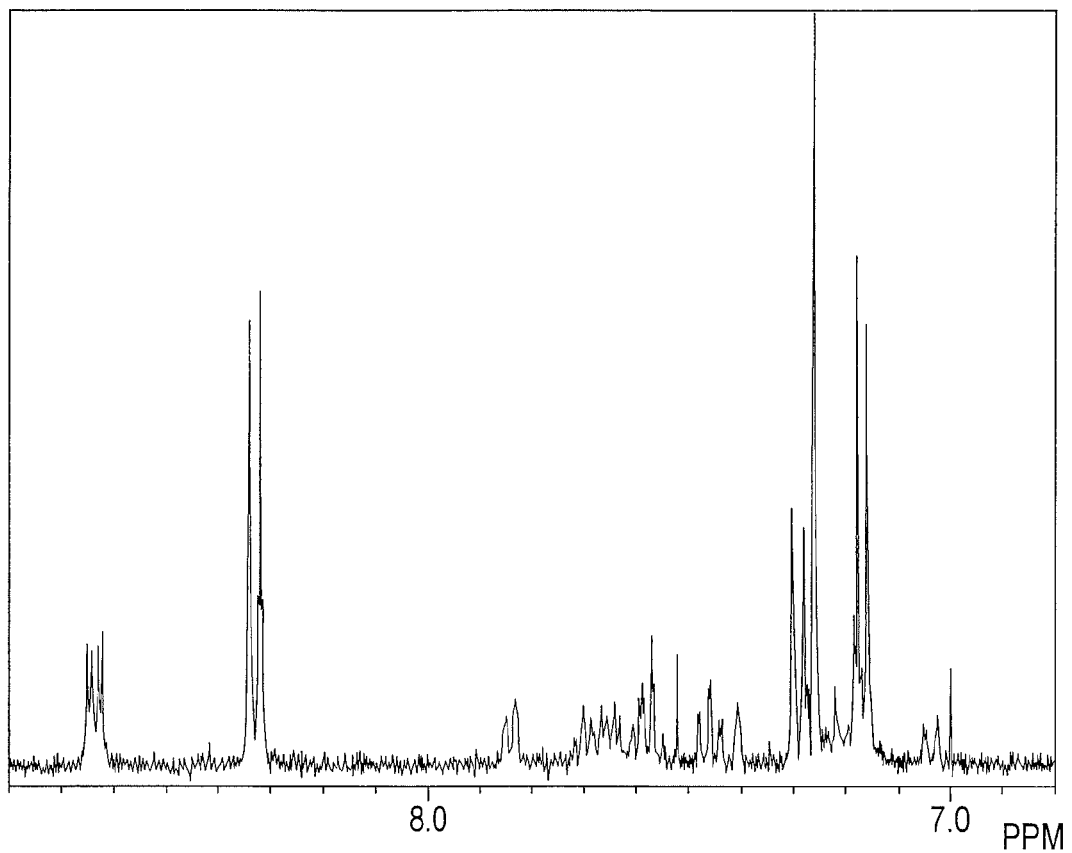
FIG. 4B is a magnified view of the NMR chart of FIG. 4A.

A $^1$H NMR chart (400 MHz, d-CDCl$_3$) of the isomer component 1 of the compound shown by the compound 2 of the present invention is shown in FIG. 4A (CHCl$_3$: 7.26 ppm, water: 1.55 ppm). Further, FIG. 4B is an enlarged view of FIG. 4A.

δ 1.17 (s, 36H), 2.17 (s, 1H), 2.30 (s, 2H), 7.02 (t, 1H), 7.16 (d, J=8.0 Hz, 8H), 7.2-7.8 (m, 9H), 7.83 (d, J=7.4 Hz, 2H), 8.32 (dd, J=6.4 Hz, J=1.8 Hz, 8H), 8.63 (dd, J=8.24 Hz, J=2.8 Hz, 3H).

Isomer component 2 (retention time: 25.7 min in HPLC analysis, considered to be start-point adsorption in TLC when developed using hexane:ether=100:1 because of low solubility)

Purity of HPLC: 92%. Amount of the product: 0.2 g (crude product).

Conditions of HPLC (column: Mightysil 18 GP 150-4.6 (particle diameter: 5 μm) UV: 254 nm, eluent: CH$_3$CN/THF (80/20)).

Peak molecular weights of 1206.84 (M$^+$+Na) and 1222.79 (M$^+$+K) obtained in mass analysis ESI-mass coincided with the calculated value (C$_{85}$H$_{78}$N$_6$: 1183.57) of the target product.

Figure 5A:
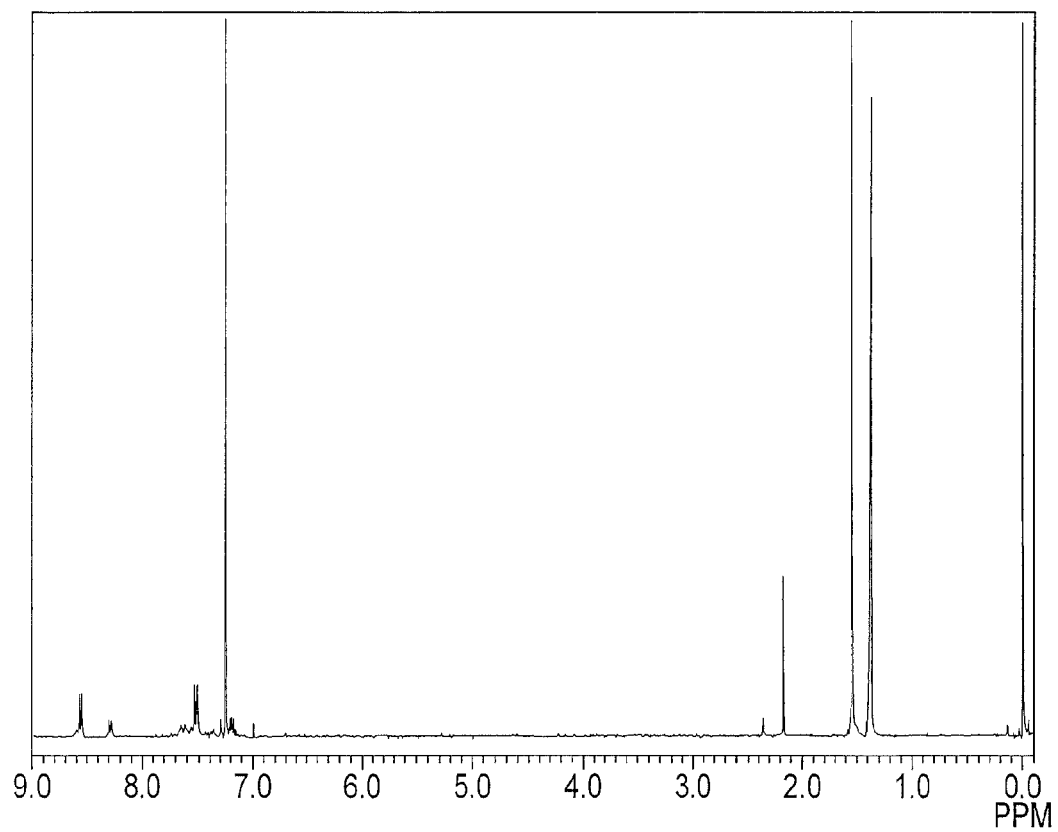
FIG. 5A is a $^1$H-NMR chart of an isomer component 2 of a compound 2 according to an example of the present invention.

A $^1$H NMR chart (400 MHz, d-CDCl$_3$) of the isomer component 2 of the compound shown by the compound 2 of the present invention is shown in FIG. 5A. Further, FIG. 5B is an enlarged view of FIG. 5A.

δ 1.38 (s, 36H), 2.17 (s, 2H), 2.37 (s, 1H), 6.99-7.7 (m, 28H), 8.30 (d, J=14.2 Hz, J=5.96 Hz, 3H), 8.59 (dd, J=19.72 Hz, J=8.72 Hz, 8H).

The characteristics of the compound 2 are shown below.

<Thermal Analysis>

The glass transition temperature (Tg), crystallization temperature (Tc), and melting point (Tm) of the isomer component 1 of the compound 2 were measured by an EXSTAR6000Series DSC6200 manufactured by Seiko Instruments Inc., at a temperature rise rate of 20° C./min.

In the first heatup, an exothermic peak (peak temperature 366° C.) that was considered to be due to Tc or a transition from a Syn-configuration to an Anti-configuration produced by the rotation of two substituents at the ninth and tenth positions were shown at a temperature range from 318° C. to 371° C. Tm was 477° C. to 488° C. (peak 483° C.)

After the temperature reached Tm, the sample was rapidly cooled, and in the second heatup, no exothermic peak or endothermic peak was observed except that Tg was observed at 214 to 227° C., thus the sample was thermally very stable.

<Solubility>

The isomer component 1 of compound 2 was dissolved in a concentration of 34 mg in 1 ml of toluene at ambient temperature and used for ink that formed each layer of an organic EL as a carrier transport layer, each color light-emitting host and light-emitting dopant, thereby enabling the formation of a coating film.

<Energy Level of the Compound 2>

A solution prepared by dissolving 10 mg of the isomer component 1 of the compound 2 in 1 ml of toluene was applied to an ITO transparent electroconductive glass by spin coating to measure the ionization potential by a surface analyzer AC-1 manufactured by Riken Keiki Co., Ltd., to find that the ionization potential was 5.9 eV. The electron affinity obtained by subtracting absorption-edge energy from the ionization potential was 2.9 eV.

<Fluorescent Spectrum>

FIG. 3 shows the fluorescent spectrum of a spin coat film of the compound 2 on a transparent electroconductive glass with an ITO film when it is measured by a fluorophotometer (trade name: RF-5300PC, manufactured by Shimadzu Corporation). The compound 2 exhibited a blue color having an excitation wavelength of 340 nm and a fluorescent peak wavelength of 454 nm.

Example 3

Synthesis of 2-tert-butyl-9,10-bis{4-[2,4-bis(4-tert-butylphenyl)-1,3,5-triazine-6-yl]biphenyl-2'-yl}anthracene (Compound 3)

Synthetic Example of an Intermediate 9

Synthesis of 2-tert-buty-9,10-bis{4-[2,4-bis(4-tert-butylphenyl)-1,3,5-triazine-6-yl]biphenyl-2'-yl}-9,9,10,10-tetrahydroanthracene-9,10-diol (intermediate I)

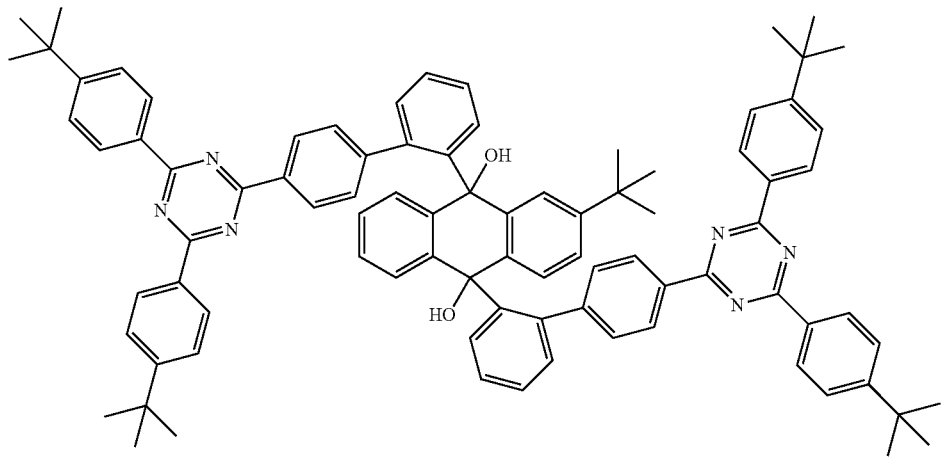

Intermediate I

In an argon atmosphere, 1.5 g (2.6 mmol) of 2,4-bis(4-tert-butylphenyl)-6-(2'-bromobiphenyl-4-yl)-1,3,5-triazine was dissolved in 25 ml of tetrahydrofuran and the solution was cooled to −70° C. or less. Then, 1.94 mL (3.1 mmol) of a 1.6 M n-butyllithium/hexane solution was added dropwise to the solution. The mixture was stirred at the same temperature for 1 hr, 0.32 g (1.2 mmol) of 2-tert-butyl-anthraquinone was added to the solution, and the mixture was gradually raised to ambient temperature, followed by stirring overnight to react.

After the reaction had finished, the reaction mixture was poured into an aqueous saturated ammonium chloride solution and extracted with methylene chloride. Further, the organic layer was isolated and dried with sodium sulfate anhydride. A solvent was distilled to obtain 1.53 g (many spots in TLC) of 2-tert-butyl-9,10-bis{4-[2,4-bis(4-tert-butylphenyl)-1,3,5-triazine-6-yl]biphenyl-2'-yl}-9,9,10,10-tetrahydroanthracene-9,10-diol as a crude product, which was used in the next step as it was.

Synthetic Example 3

Synthesis of 2-tert-butyl-9,10-bis{4-[2,4-bis(4-tert-butylphenyl)-1,3,5-triazine-6-yl]biphenyl-2'-yl}-anthracene (Compound 3)

Compound 3

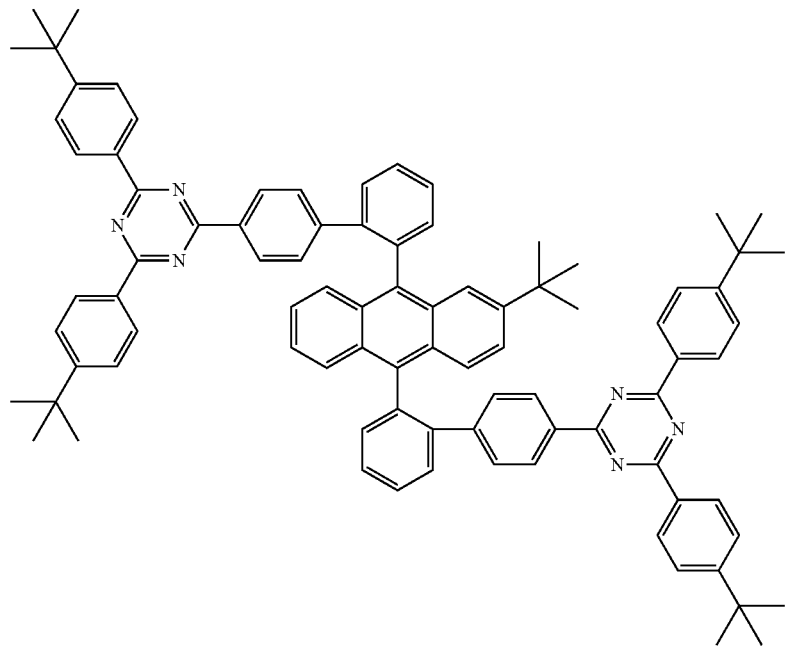

A crude product of 2-tert-butyl-9,10-bis{4-[2,4-bis(4-tert-butylphenyl)-1,3,5-triazine-6-yl]biphenyl-2'-yl}-9,9,10,10-tetrahydroanthracene-9,10-diol (intermediate 1) was dissolved in 50 mL of acetic acid, to which were then added 0.5 g (3.0 mmol) of potassium iodide and 0.16 g (1.51 mmol) of NaH$_2$PO$_2$, and the mixture was refluxed with stirring for 4 hr.

After the reaction had finished, the reaction mixture was poured into water, which was then extracted with methylene chloride. The organic layer was isolated, washed with water, dried using sodium sulfate and then a solvent was distilled. The obtained residue was purified by silica gel TLC using hexane-methylene chloride (2/1) as an eluent to obtain a major component (isomer of lower side components) having an Rf value of 0.34. This major component was purified by silica gel column chromatography using hexane-methylene chloride (4/1) as an eluent to obtain 0.23 g (15.5%: yield from 2-t-butylanthraquinone) of 2-tert-butyl-9,10-bis{4-[2,4-bis(4-tert-butylphenyl)-1,3,5-triazine-6-yl]biphenyl-2'-yl}-anthracene with an HPLC purity of 97.1%.

A peak molecular weight of 1225.80 obtained in ESI-Ms mass analysis coincided with the calculated value (C$_{88}$H$_{84}$N$_6$: 1225.65) of the target product.

Figure 6A:
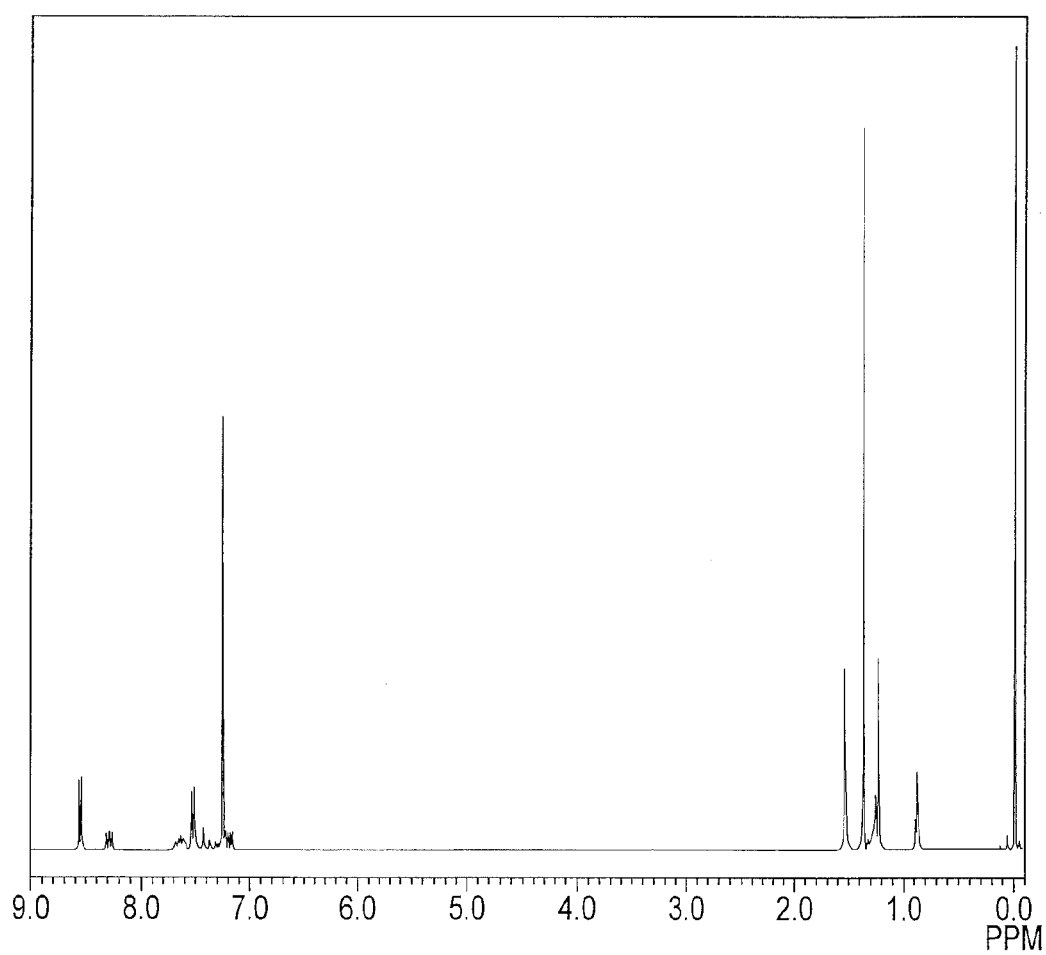
FIG. 6A is a $^1$H-NMR chart of a compound 3 according to an example of the present invention.
Figure 6B:
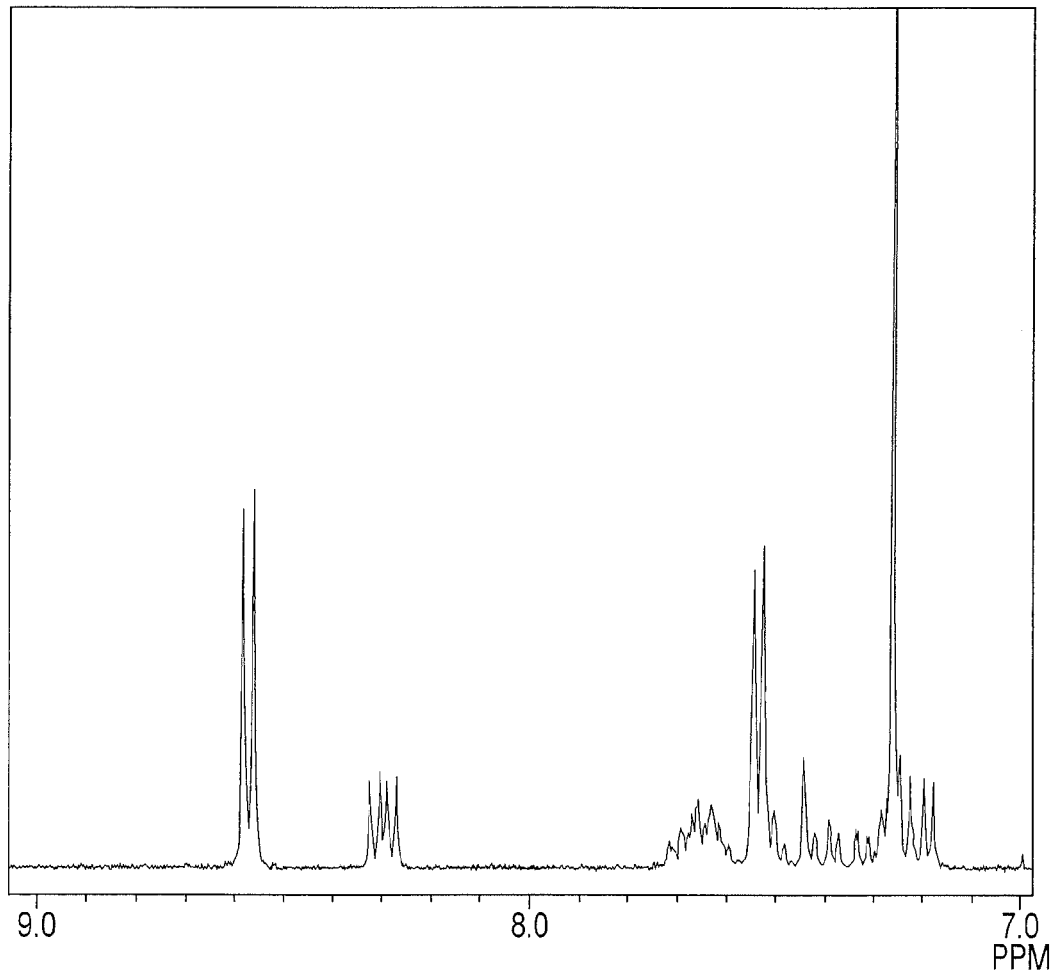
FIG. 6B is an enlarged view of the NMR chart of FIG. 6A.

A $^1$H NMR chart (400 MHz, d-CDCl$_3$) of the compound (Rf value: 0.34) shown by the compound 3 of the present invention is shown in FIG. 6A. Further, FIG. 6B is an enlarged view of FIG. 6A.

δ 1.17 (s, 9H), 1.37 (s, 36H), 7.19 (d, J=8.3 Hz, 2H), 7.24 (d, J=8.7 Hz, 2H), 7.26-7.00 (m, 1H), 7.32 (dd, J=9.1 Hz, 1.8 Hz, 1H), 7.38 (d, J=7.8 Hz, 1H), 7.42-7.46 (m, 2H), 7.46-7.52 (m, 1H), 7.54 (d, J=8.2 Hz, 11H), 7.59-7.71 (m, 6H), 8.28 (d, J=8.2 Hz, 2H), 8.31 (d, J=8.2 Hz, 2H), 8.57 (d, J=8.2 Hz, 8H).

The characteristics of the compound 3 are shown below.

<Thermal Analysis>

The glass transition temperature (Tg), crystallization temperature (Tc), and melting point (Tm) of the compound 3 were measured by an EXSTAR6000 Series DSC6200 manufactured by Seiko Instruments Inc. When the temperature of the compound 3 was raised at a temperature rise rate of 20° C./min and the compound was rapidly cooled from 337° C. to 0° C. and again raised at a temperature rise rate of 20° C./min, no exothermic peak or endothermic peak was observed at a temperature of 400° C. or more except that Tg was observed at 205 to 219° C., thus the sample was thermally very stable.

<Solubility>

The compound 3 was dissolved in a concentration of 150 mg in 1 ml of toluene at ambient temperature and used for ink that formed each layer of an organic EL as a carrier transport layer, each color light-emitting host, or blue light-emitting dopant, thereby enabling the formation of a coating film.

<Energy Level of the Compound 3>

A solution prepared by dissolving 10 mg of the compound 1 in 1 ml of toluene was applied to an ITO transparent electroconductive glass by spin coating to measure the ionization potential by a surface analyzer AC-1 manufactured by Riken Keiki Co., Ltd., to find that the ionization potential was 5.9 eV. The electron affinity obtained by subtracting the absorption-edge energy from the ionization potential was 3.0 eV.

<Fluorescent Spectrum>

FIG. 3 shows the fluorescent spectrum of a spin coat film of the compound 3 on an ITO transparent electroconductive glass when it is measured by a fluorophotometer (trade name: RF-5300PC, manufactured by Shimadzu Corporation). The compound 3 exhibited a blue color having a fluorescent peak wavelength of 453 nm and an excitation wavelength of 330 nm.

Example 4

Synthesis of 2,2'-bis(4-(2,4-bis(4-tert-butylphenyl)-1,3,5-triazine-6-yl)phenyl)-9,9'-spirobifluorene (BTrSBF: Compound 31)

Synthetic Example of an Intermediate 10

Synthesis of 2,2'-bis(4,4,5,5-tetramethyl-1,3,2-dioxaborolane-2-yl)-9,9'-spirobifluorene (intermediate J)

Intermediate J

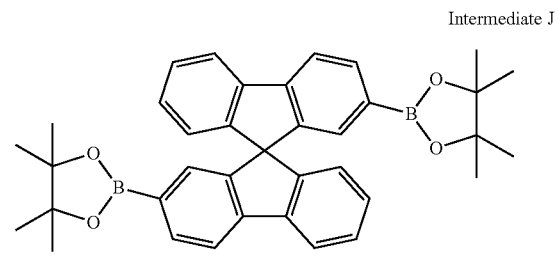

In an argon atmosphere, 0.45 g (0.55 mmol) of PdCl$_2$ (dppf) was added to a mixture of 2.0 g (4.22 mmol) of 2,2'-dibromo-9,9'-spirobifluorene, 2.36 g (9.28 mmol) of bis(pinacolate)diborane, 2.48 g (25.31 mmol) of potassium acetate, and 68 mL of DMF, and the mixture was stirred at 80 to 90° C. for 48 hr.

After the reaction was finished, DMF was distilled from the reaction mixture and the residue was then extracted with methylene chloride. The extract was then washed with water and dried with sodium sulfate anhydride. A solvent was distilled and the obtained residue was purified by silica gel column chromatography using hexane-methylene (1:2) as an eluent to obtain 2.07 g (3.64 mmol) of 2,2'-bis(4,4,5,5-tetramethyl-1,3,2-dioxaborolane-2-yl)-9,9'-spirobifluorene (intermediate J) at a yield of 86.3%.

$^1$H NMR (400 MHz, d-CDCl$_3$): δ 1.25 (s, 24H), 6.66 (d, J=7.8 Hz, 2H), 7.09 (td, J=7.4 Hz, 1.1 Hz, 2H), 7.17 (s, 2H), 7.35 (td, J=7.6 Hz, 0.9 Hz, 2H), 7.83-7.87 (m, 6H).

Synthetic Example of Compound 31

Synthesis of 2,2'-bis(4-(2,4-bis(4-tert-butylphenyl)-1,3,5-triazine-6-yl)phenyl)-9,9'-spirobifluorene (Compound 31)

In an argon atmosphere, a mixture of 1.0 g (1.76 mmol) of 2,2-bis(4,4,5,5-tetramethyl-1,3,2-dioxaborane-2-yl)-9,9'-spirobifluorene, 1.76 g (3.52 mmol) of 2,4-bis(4-tert-butylphenyl)-6-(4-bromophenyl)-1,3,5-triazine, 3.5 mL of 2M Na$_2$CO$_3$, and 50 mL of DMF was deoxidized at ambient temperature.

0.41 g (0.35 mmol) of Pd(PPh$_3$)$_4$ (tetrakistriphenylphosphinepalladium: 0 valence) was added to the mixture, which was then stirred at 85° C. for 48 hr.

After the reaction had finished, the reaction mixture was poured into water, which was then extracted with methylene chloride and dried by sodium sulfate anhydride. Then, a solvent was distilled and the obtained residue was washed with an acetone-methanol mixed solvent and then, purified by silica gel chromatography using hexane-methylene chloride (6:1) as an eluent to obtain 0.66 g (0.571 mmol) of 2,2'-bis (4-(2,4-bis(4-tert-butylphenyl)-1,3,5-triazine-6-yl)phenyl)-9,9'-spirobifluorene (Compound 31) (HPLC purity: 100.0%) at a yield of 32.5%.

Condition of HPLC: when an HPLC column Mightysil RP-18 GP manufactured by Kanto Chemical Co., Inc., (particle diameter: 5 μm, diameter: 4.6 mm, length: 150 mm) was used and an eluent constituted of acetonitrile/tetrahydrofuran (80/20) was made to flow at a flow rate of 1.5 ml/min to detect by 254 nm UV, a single peak with a retention time of 23.64 min was obtained (purity: 100.0%).

A main peak of 1155.72 ($M^+$) obtained in ESI-Ms mass analysis coincided with the calculated value ($C_{83}H_{74}N_6$: 1155.72) of the target product.

Figure 7B:
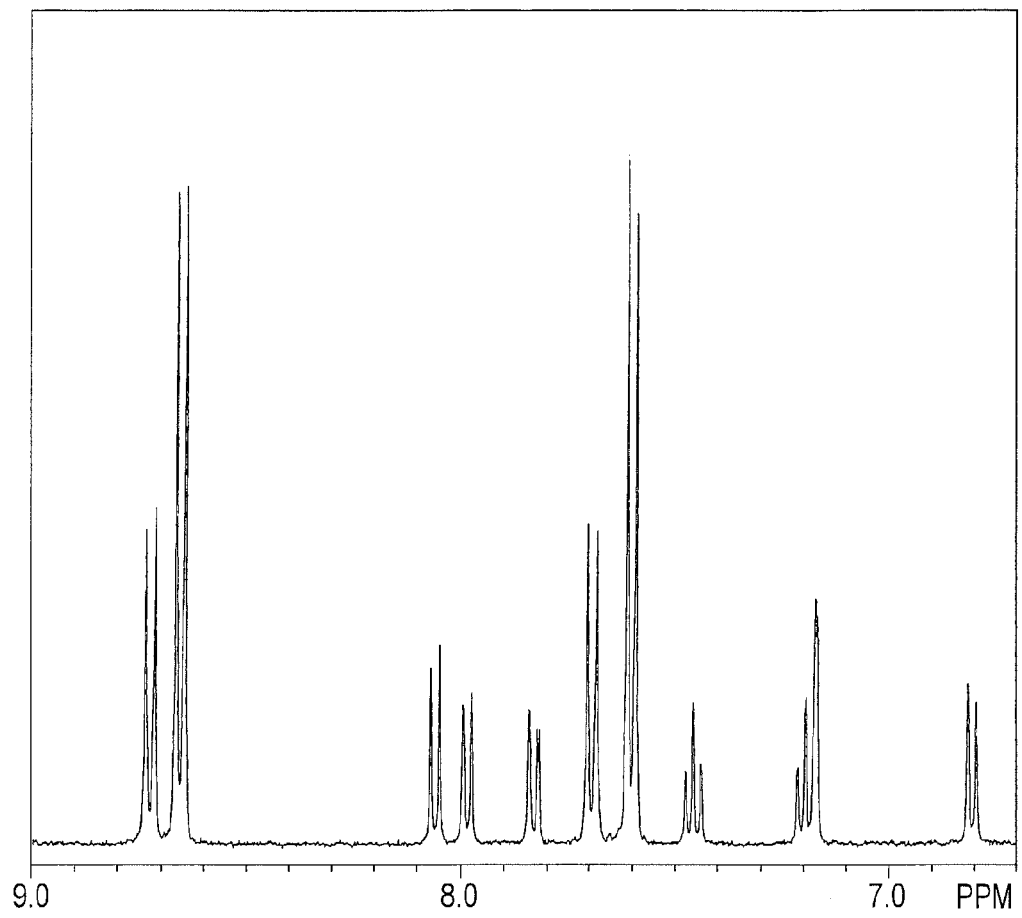
FIG. 7B is an enlarged view of the NMR chart of FIG. 7A.

A $^1$H NMR chart (400 MHz, d-$CD_2Cl_2$) of the compound shown by the compound 31 of the present invention is shown in FIG. 7A. Further, FIG. 7B is an enlarged view of FIG. 7A.

$^1$H NMR (400 MHz, d-$CDCl_3$): δ 1.39 (s, 36H), 6.80 (d, J=7.8 Hz, 2H), 7.17 (d, J=1.4 Hz, 2H), 7.19 (t, J=7.3 Hz, 2H), 7.45 (t, J=7.1 Hz, 2H), 7.60 (d, J=8.5 Hz, 8H), 7.69 (d, J=8.7 Hz, 4H), 7.83 (dd, J=8.0 Hz, 1.6 Hz, 2H), 7.98 (d, J=7.8 Hz, 2H), 8.05 (d, J=7.8 Hz, 2H), 8.66 (d, J=8.5 Hz, 8H), 8.72 (d, J=8.7 Hz, 4H).

The characteristics of the compound 31 are shown below.

<Thermal Analysis>

The glass transition temperature (Tg), crystallization temperature (Tc), and melting point (Tm) of the compound 31 were measured by an EXSTAR6000 Series DSC6200 manufactured by Seiko Instruments Inc. When the sample was heated at a rate of 20° C./min, then rapidly cooled to 0° C. from 350° C., and then, heated again at a rate of 20° C./min, the sample had a Tg of 238° C. to 257° C. Except for this Tg, no exothermic peak or endothermic peak was found, showing that the sample was a thermally stable glass-like material.

<Solubility and Film-Formability>

The compound 31 had highly amorphous characteristics and was dissolved in a concentration as high as 0.4 g in 1 ml of toluene at ambient temperature and was easily soluble in various aromatic solvents such as xylene, anisole, 4-methylanisole, and tetralin, and also soluble in highly viscous cycloalcohol solvents such as cycloheptanol and cyclooctanol. Further, the compound 31 can be dissolved in various mixture solvents to be matched with the viscosities of various printing systems.

The compound 31 may be dissolved in a desired concentration in a solvent suitable for various printing systems by coating such as the spin coating method, die coating method, capillary coating method, inkjet method, continuous nozzle printing method, relief-printing method, and gravure printing method to form an amorphous film. Therefore, the compound 31 may be used as host materials for carrier transport layers such as a hole block layer, electron transport layer and, for example, red, blue, or green light emitting layers in organic electroluminescent devices.

<Energy Level of the Compound 31>

A solution prepared by dissolving 10 mg of the compound 31 in 1 ml of toluene was applied to an ITO transparent electroconductive glass by spin coating to measure the ionization potential by a surface analyzer AC-1 manufactured by Riken Keiki Co., Ltd., to find that the ionization potential was 6.2 eV. The electron affinity obtained by subtracting absorption-edge energy from the ionization potential was 3.0 eV.

<Fluorescent Spectrum>

The fluorescent spectrum of a spin coat film of the compound 31 on an ITO transparent electroconductive glass was measured. The results correspond to a graph (0 wt %) of FIG. 8. The measurement was made by a fluorophotometer (trade name: RF-5300PC, manufactured by Shimadzu Corporation). The compound 31 emitted blue light having a fluorescent peak wavelength of 422 nm.

Example 5

Ink was produced which had a composition prepared by dissolving a carrier transport host material BTrSBF which was represented by the compound 31 and had an ionization potential of 6.2 eV, electron affinity of 3.0 eV, and Eg of 3.2 eV and 5 to 20 wt % of the compound 2 as a light emitting dopant in toluene. A film of the ink was formed on an ITO transparent electroconductive glass by spin coating and the fluorescent spectrum intensity was measured by a fluorophotometer (trade name: RF-5300PC, manufactured by Shimadzu Corporation) at an excitation spectrum of 340 nm.

Figure 8:
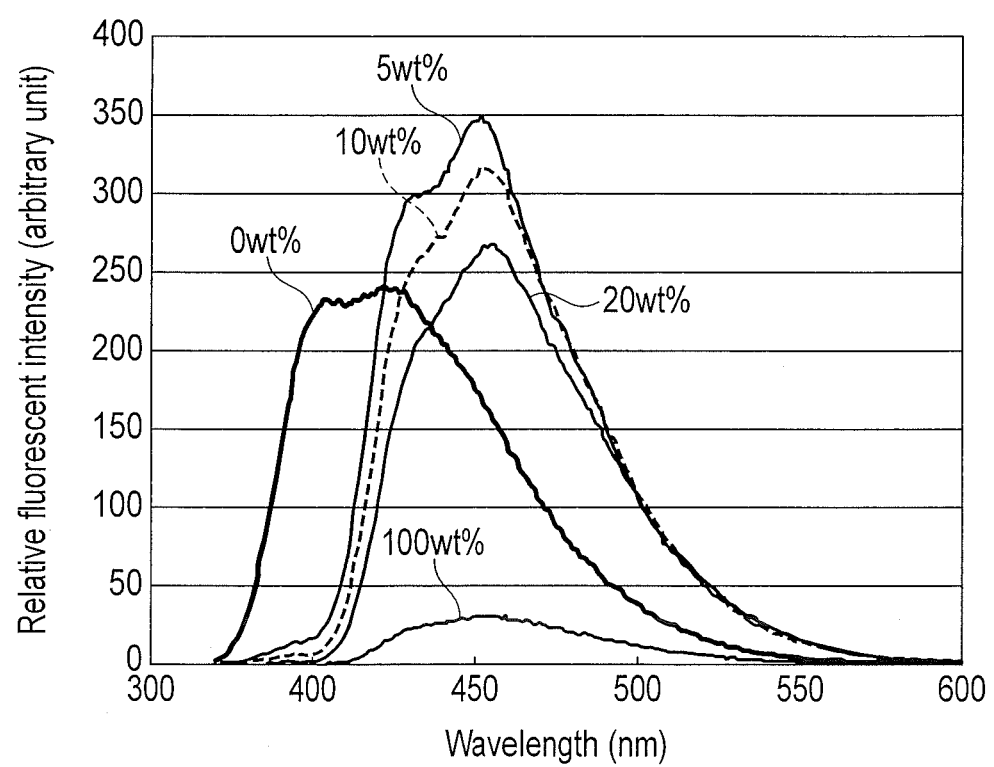
FIG. 8 is a fluorescent spectrum chart used to determine the concentration of a dopant in a light-emitting layer used in an organic electroluminescent device according to an embodiment of the present invention.

FIG. 8 shows each fluorescent spectrum (excitation spectrum: 340 nm) when the compound 31 is doped with the isomer component 1 of the compound 2 (the contents of the compound 2 were designed to be 0, 5, 10, 20, and 100 wt %, and the contents of the compound 31 in this case were designed to be 100, 95, 90, 80, and 0 wt %). It was found from FIG. 8 that when the host material BTrSBF having a larger Eg (3.2 eV) was doped with the compound 2 (Eg: about 2.9 eV), energy could be transferred from the host to the dopant highly efficiently and a light emitting film which was suppressed in concentration quenching and emitted intensive blue light from the dopant could be obtained.

Using a fluorophotometer (trade name: RF-5300PC, manufactured by Shimadzu Corporation) wherein the width of the slit for excitation light was changed to 1.5 nm, this light emitting film was successively irradiated with light having a wavelength of 340 nm for 1,000 sec, with the result that a single film of the isomer component 1 of the compound 2 was decreased in fluorescent intensity to 57% of the initial intensity and the single film of BTrSBF was decreased to 64% of the initial intensity whereas the film obtained by doping BTrSBF with 5 wt % of the compound 2 kept 74% of the initial intensity, showing that this film had the effect of suppressing the optical deterioration of fluorescent intensity.

Example 6

Synthesis of an Analogue of the Compound 31 (compound 32)

An intermediate K was synthesized in the same manner as in the synthetic example of an intermediate 1 except that 4-methylbenzonitrile was used in place of 4-tert-butylbenzonitrile. A compound 32 (HPLC purity: 100.0%) was synthesized in the same manner as in the synthesis of the compound 31 except that the intermediate K was used in place of the intermediate A.

Compound 32

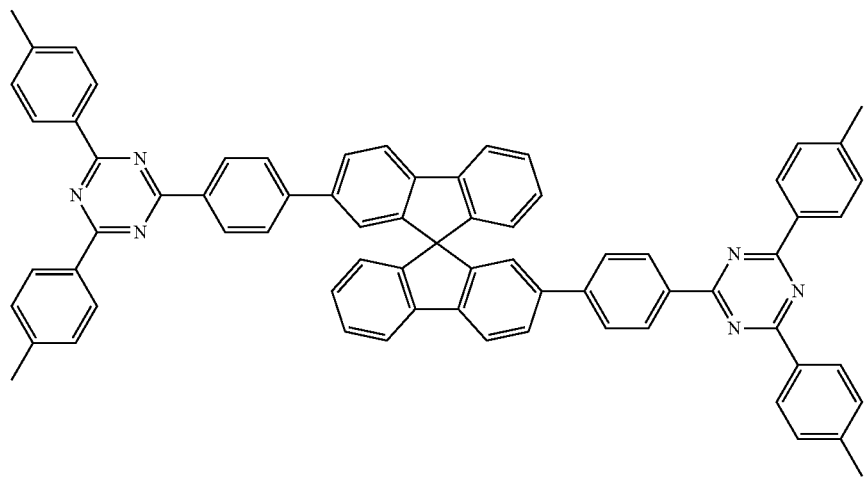

Analytical conditions of HPLC: when an HPLC column Mightysil RP-18 GP manufactured by Kanto Chemical Co., Inc., (particle diameter: 5 μm, diameter: 4.6 mm, length: 150 mm) was used and an eluent constituted of acetonitrile/tetrahydrofuran (80/20) was made to flow at a flow rate of 1.0 ml/min to detect by 254 nm UV, a single peak with a retention time of 16.34 min was obtained (purity: 100.0%).

Figure 9A:
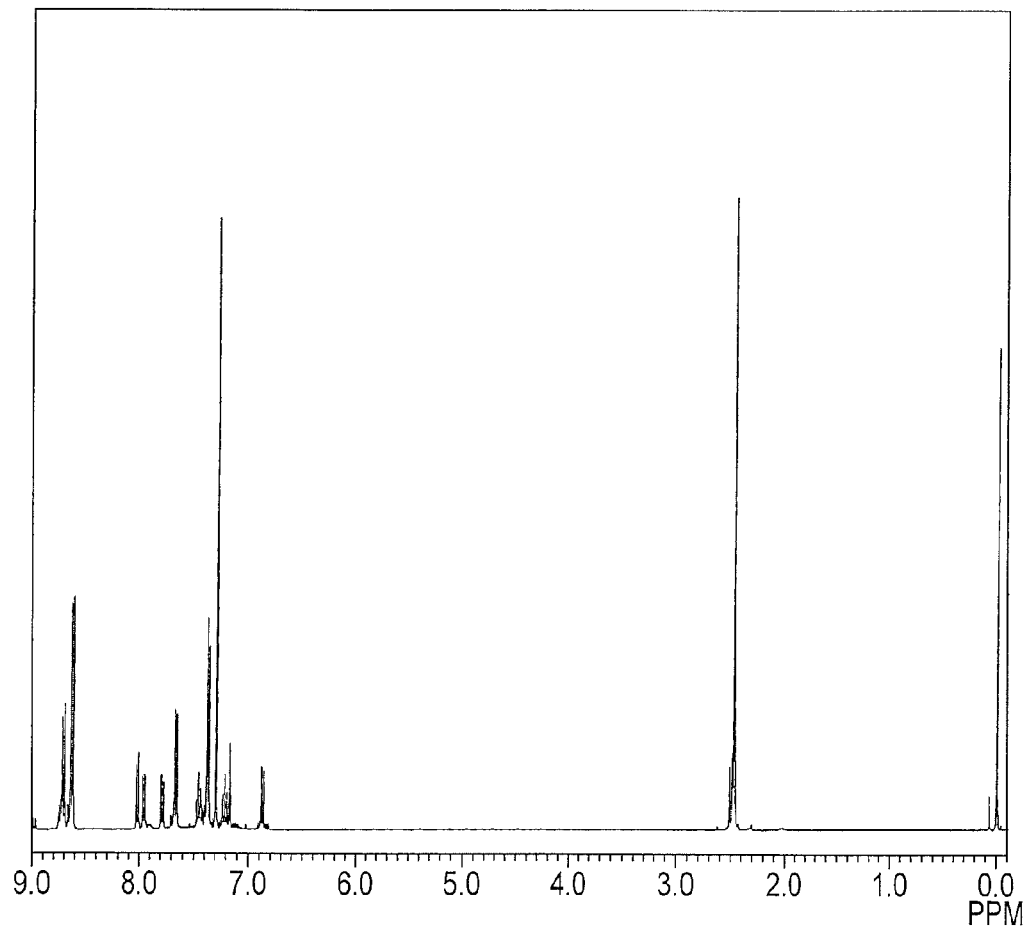
FIG. 9A is a $^1$H-NMR chart of a compound 32 according to an example of the present invention.
Figure 9B:
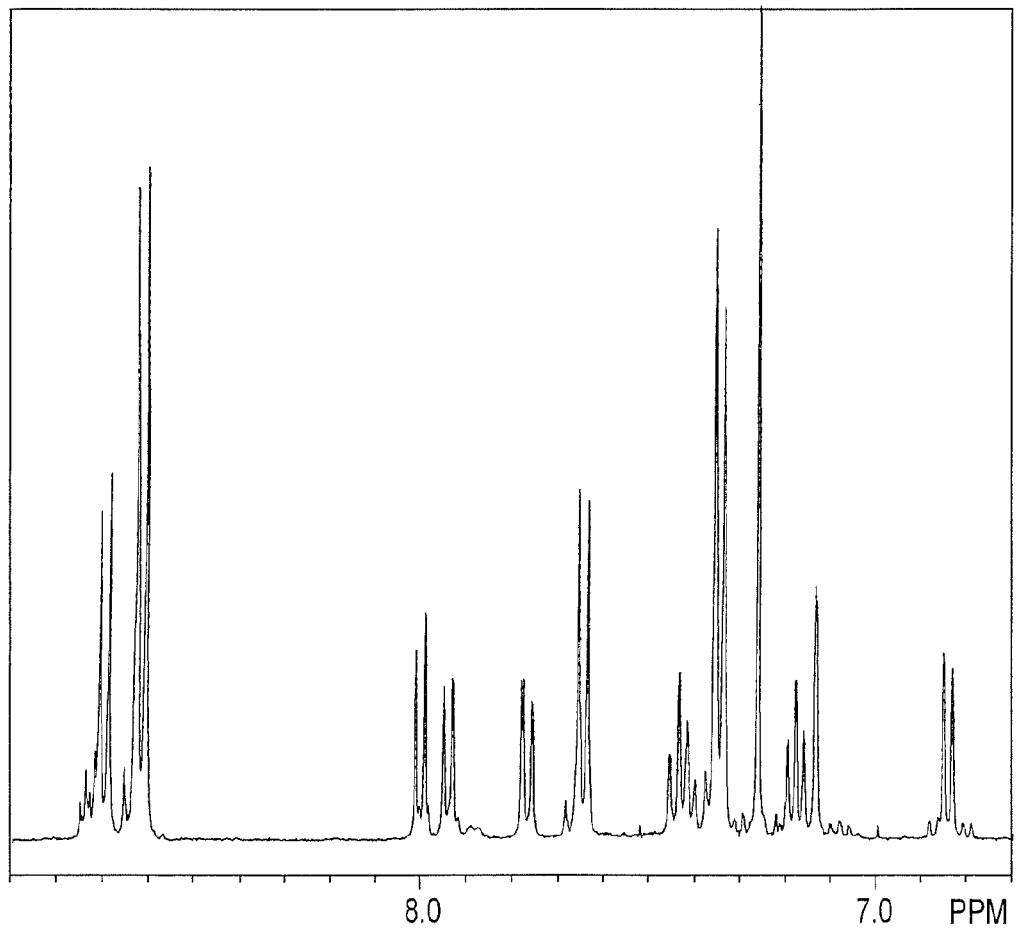
FIG. 9B is an enlarged view of the NMR chart of FIG. 9A.

A $^1$H NMR chart (400 MHz, d-CD$_2$Cl$_2$) of the compound 32 of the present invention is shown in FIG. 9A. Further, FIG. 9B is an enlarged view of FIG. 9A.

$^1$H NMR (400 MHz, d-CDCl$_3$): δ 2.47 (s, 12H), 6.83 (d, J=7.8 Hz, 2H), 7.13 (d, J=1.4 Hz, 2H), 7.17 (t, J=7.3 Hz, 2H), 7.34 (t, J=7.8 Hz, 8H), 7.43 (t, J=7.2 Hz, 2H), 7.65 (d, J=8.7 Hz, 4H), 7.76 (dd, J=8.0 Hz, 1.6 Hz, 2H), 7.93 (d, J=7.3 Hz, 2H), 7.99 (d, J=7.8 Hz, 2H), 8.61 (d, J=8.2 Hz, 8H), 8.70 (d, J=8.7 Hz, 4H).

The characteristics of the compound 32 are shown below.

<Thermal Analysis>

The glass transition temperature (Tg), crystallization temperature (Tc), and melting point (Tm) of the compound 32 were measured by an EXSTAR6000 Series DSC6200 manufactured by Seiko Instruments Inc. When the sample was heated at a rate of 20° C./min, then rapidly cooled to 0° C. from 375° C., and then, heated again at a rate of 20° C./min, the sample had a Tg of 205° C. to 221° C., a crystallization peak (Tc) of 320° C., and a Tm (peak 387° C.) from 369° C. to 397° C.

<Solubility>

The compound 32 was soluble in a concentration of 6 mg in 1 ml of toluene at ambient temperature. When the compound 32 was gradually added to dissolve while heating on a hot plate, 34 mg of the compound 32 was dissolved when the temperature was returned to ambient temperature. The compound 32 can be used as an electron transportable carrier transport material and may be dissolved in an organic solvent such as toluene, xylene, anisole, and tetralin to add the obtained solution to ink for forming each layer of an organic EL, thereby forming a coating film.

<Energy Level of the Compound 32>

A solution prepared by dissolving 10 mg of the compound 32 in 1 ml of toluene was applied to an ITO transparent electroconductive glass by spin coating to measure the ionization potential by a surface analyzer AC-1 manufactured by Riken Keiki Co., Ltd., to find that the ionization potential was 6.2 eV. The electron affinity obtained by subtracting absorption-edge energy from the ionization potential was 3.0 eV.

<Fluorescent Spectrum>

FIG. 10 shows a fluorescent spectrum chart (solid line) of the compound 32 and a fluorescent spectrum chart (dotted line) obtained when the compound 32 was doped with the compound 2. First, a fluorescent spectrum obtained when a film formed in a thickness of 41 nm by applying a solution of the compound 32 to the surface of an ITO transparent electroconductive glass by spin coating was excited by 340 nm light was obtained (solid line in FIG. 10). The measurement was made by a fluorophotometer (trade name: RF-5300PC, manufactured by Shimadzu Corporation). Blue light emission having a fluorescent peak wavelength of 424 nm was obtained.

A fluorescent spectrum obtained when a film was formed in the same manner as above by doping the compound 32 with 5 wt % of the compound 2 was measured in the same manner as above. The results are shown by the dotted line in FIG. 10. The fluorescent peak wavelength was 453 nm and pure blue light emission was obtained which was more intensified than the case where the compound 32 was not doped with the compound 2.

<Vacuum Deposition Temperature>

20 mg of the compound 32 was poured into an Mo boat Bu-6 (trade name, manufactured by Japan Vacs Metal Co., Ltd.), which was then set to a vacuum deposition apparatus to raise the temperature of the compound 32 under a vacuum of 1E-5 Torr or less while measuring the temperature by a thermocouple. As a result, the rate of film formation on a quartz substrate arranged above 30 cm apart from the boat was 0.1 nm/s at a boat temperature of 480° C.

Example 7

A method for fabricating a donor base material according to an embodiment of the present invention will be explained with reference to FIG. 11.

A transparent substrate 16 which had a low coefficient of expansion and was made of vycor glass or a ceramic glass was etched to make a spacer dividing wall 19 having a height of about 2 μm corresponding to the intervals between stripe lines of blue, red, green, and the like which form pixels on a display substrate. Next, after a liftoff resist was applied, a photoabsorptive film which had a thickness of 100 to 200 nm and was made of $CrO_x$ or $MoO_x$ (x is an optional number) between the divided walls by the sputtering method and the resist was removed to form a photoabsorptive layer 17. Then, aluminum was deposited in a thickness of 50 to 100 nm to form a light reflection layer 18.

Next, the compound 1 which had a molecular weight of 1169.5 and was obtained in Example 1 was blended as a dopant material in a ratio of 5 wt % in a host material made of the compound 31 having a molecular weight of 1155.5 and the mixture was dissolved in toluene to make blue light emitting layer ink, which was then applied to the surface of the photoabsorptive layer by the continuous nozzle printing method. The formed film was dried at 200° C. under vacuum to obtain a laser transfer donor base material for a blue light-emitting layer which was provided with a blue light-emitting layer transfer layer 20 having a thickness of 60 nm.

Example 8

The compound 8 which had a molecular weight of 1219.6 was blended as a dopant material in a ratio of 10 wt % in a host material which had a molecular weight of 1225.6 and was made of the compound 3 obtained in Example 3 and the mixture was dissolved in toluene to make green light emitting layer ink, to obtain a laser transfer donor base material provided with a 60-nm-thick transfer layer 20 for a green light-emitting layer in the same manner as in Example 7.

Example 9

The compound 11 which had a molecular weight of 1269.7 was blended as a dopant material in a ratio of 10 wt % in a host material which had a molecular weight of 1225.6 and was made of the compound 3 obtained in Example 3 and the mixture was dissolved in toluene to make red light emitting layer ink, to obtain a laser transfer donor base material provided with a transfer layer 20 for a red light-emitting layer in the same manner as in Example 7.

Example 10

Synthesis of 1,3,5-tris(4-(3,6-di-tert-butyl-N-carbazolyl)phenyl)benzene (compound 33)

In an argon atmosphere, 110 ml of dehydrated 1,4-dioxane was added in 0.99 g (1.8 mmol) of 1,3,5-tris(4-bromophenyl)benzene, 2.51 g (9.0 mmol) of 3,6-di-tert-butylcarbazol synthesized according to the method described in J. Am. Chem. Soc. 2006, vol 128, pp 5592-5593, 0.34 g (1.8 mmol) of copper (I) iodide, and 1.91 g (9.0 mmol) of potassium phosphate, and the mixture was stirred for several min. Then, 0.41 g (3.6 mmol) of trans-1,2-cyclohexanediamine was added to the mixture, which was then heated at 110° C. with stirring for 30 hr to react.

After the reaction was finished, a solvent was distilled from the reaction mixture, and the obtained residue was extracted with methylene chloride, washed with water, and dried with sodium sulfate anhydride. A solvent was distilled and the resulting residue was purified by silica gel chromatography using hexane-methylene chloride (4:1) as an eluent to obtain 1.13 g (0.99 mmol) of tris(4-(3,6-di-tert-butylcarbazolyl)phenyl)benzene having a purity of 99% at a yield of 55%.

A main peak of 1138 was obtained in mass analysis of the compound 33 and coincided with the calculated value ($C_{84}H_{87}N_3$: 1138.61) of the target product.

The signal of NMR is shown below.

$^1$H NMR (400 MHz, d-CDCl$_3$): δ 1.49 (s, 54H), 7.46 (d, J=8.70 Hz, 6H), 7.56-7.52 (m, 6H), 7.73 (d, J=8.70 Hz, 6H), 7.80 (d, J=8.24 Hz, 6H), 8.04 (s, 3H), 8.17 (s, 6H).

The characteristics of the compound 33 are shown below.

<Thermal Analysis>

The Tg, Tc, and Tm of the compound 33 measured by DSC were 240° C., 323° C., and 403° C. respectively.

<Energy Level>

The ionization potential measured by a surface analyzer AC-1 manufactured by Riken Keiki Co., Ltd. was 6.2 eV and the electron affinity obtained by subtracting absorption-edge energy from the ionization potential was 2.8 eV.

<Solubility>

The compound 33 was dissolved in an amount of 10 wt % or more in a general organic solvent or mixture solvent such as toluene, xylene, and tetralin, showing that it was easily soluble.

<Fluorescence of the Film>

Xylene solutions containing only the compound 31, only the compound 33, and a mixture of the compound 31:compound 33:compound 3 (10:2:1 ratio by weight) such that each solid content was 2 wt % were respectively applied to a quarts plate by spin coating (rotated at 500 rpm for 5 sec and then at 1200 rpm for 60 sec) to form films having almost the same thickness, thereby measuring a fluorescent spectrum. The results are shown in FIG. 12.

The compound 33 exhibited blue fluorescent light having a peak at 380 nm. The shape of fluorescent spectrum of the mixture film of the compound 31:compound 33:compound 3 (10:2:1) doped with 7.7 wt % of the compound 3 coincided with that of the compound 3. In the case of using the mixture, a blue light emission which was more intense than in the case of using only the compound 33 or 31 was obtained.

Example 11

A method for fabricating an electroluminescent device according to an embodiment of the present invention will be explained.

An ITO film 150 nm in thickness is formed on a glass substrate 0.7 mm in thickness by the sputtering method and a stripe-like ITO film pattern is formed by carrying out wet etching by a usual method. This substrate is washed ultrasonically by using an alkali detergent, then washed with purified water, dried, and plasma-cleaned using oxygen or argon gas to prepare a substrate for an electroluminescent device or display.

In succession, molybdenum trioxide is formed on the ITO film which is to be a light-emitting region by ion plating to form a hole injection transport layer 3 nm in thickness.

Next, after a toluene solution containing 0.5 wt % of the polymer 1 is formed on the hole injection transport layer by spin coating, the film in unnecessary parts such as the terminal part is wiped off and the film is subjected to crosslinking treatment by heating in vacuo at 200° C. for 60 min to obtain an approx. 30-nm-thick electron block hole transport layer insoluble in toluene.

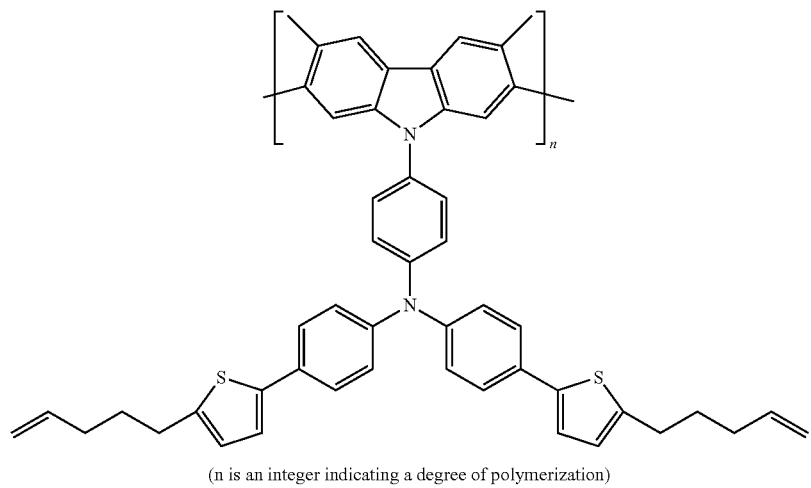

Polymer 1

(n is an integer indicating a degree of polymerization)

Next, BTrSBF represented by the compound 31 and used as a light-emitting host material is mixed with the isomer component 1 of the compound 2 obtained in Example 2 and used as a blue light-emitting dopant in a solid content ratio of 5 wt % and with a compound represented by the compound 33 as a hole transport material in a solid content ratio of 5 wt %, and the mixture is dissolved in a concentration of 1.5 wt % in toluene to form a blue fluorescent ink composition. The ink composition is applied to a crosslinked film of the polymer 1 by the spin coating method. Unnecessary film parts on, for example, the terminals are wiped off and the resulting film is heated under reduced pressure to dry it for 90 min to make a light-emitting layer having a thickness of about 60 nm.

Next, the compound 31 and lithium are codeposited in a thickness of 10 nm at a vapor deposition rate of 100:4 to form an electron injection transport layer.

Finally, LiF is deposited under vacuum in a thickness of 0.5 nm and Al is further deposited on LiF in a thickness of 150 nm to form a negative electrode.

When a DC voltage of 10 V is applied to the organic electroluminescent device fabricated in the above manner to emit light, blue light emission having high color purity is obtained.

Compound 33

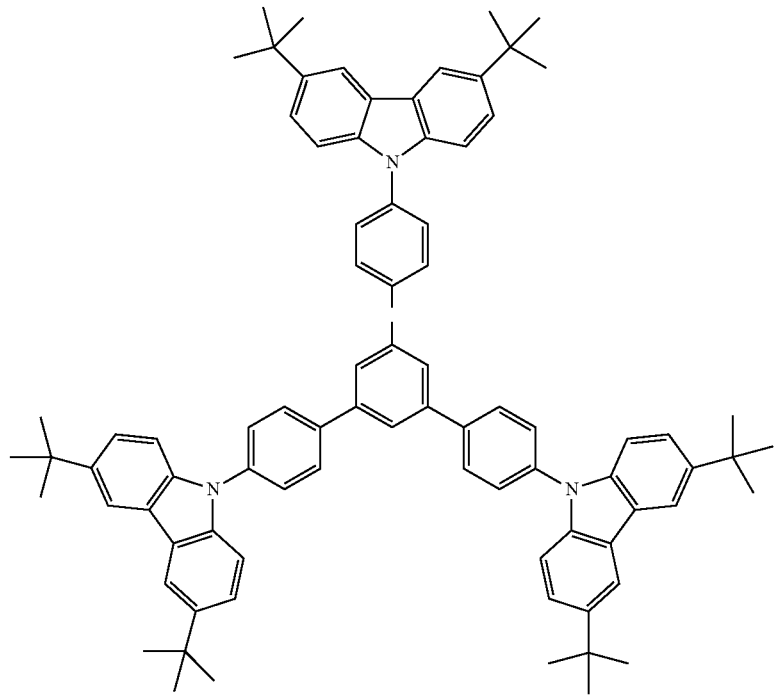

Example 12

The same procedures as in Example 11 are performed until the hole injection transport layer is formed. Next, a film of the polymer 1 is formed in a thickness of 20 nm by the slit coating method and irradiated with 365 nm ultraviolet light emitted from a 4 W low-pressure mercury lamp through a filter in an inert gas atmosphere by passing the light through a photomask in which a necessary part corresponding to the light-emitting part is opened, to undergo crosslinking reaction, thereby making the film insoluble. Then, the film is rinsed with toluene to remove the film on unnecessary parts such as a terminal part and dried to form an electron block hole transport layer.

Next, a poly(9-vinylcarbazol) which has a weight average molecular weight of 1,100,000 and is used as a thickener and a hole transport high-molecular host material in a ratio of 33 wt % on solid basis, the compound 31 which is used as an electron transport host material in a ratio of 52 wt % on solid basis, the isomer component 1 of the compound 2 obtained in Example 2 which is used as a blue light-emitting dopant material in a ratio of 5 wt % on solid basis, and a compound represented by the compound 33 which is used as a hole transport material in a ratio of 10 wt % on solid basis are mixed to prepare an ink of an anisole solution which has a total solid content ratio of 6 wt % and a viscosity of about 10 to 15 mPa·S.

This ink is applied to an anilox roll by slit coating, transferred to a projection portion on a printing precursor plate of relief printing system on which the projection portion corresponding to a pixel pattern is formed, carried out roll printing on a glass substrate on which the electron block hole transport layer is formed, and then, the film is dried to form a light-emitting layer of about 60 nm in thickness.

Next, on the light-emitting layer, the compound 31 and Al are codeposited in a thickness of 5 to 10 nm at a ratio of vapor deposition rate of 100:4 to form an electron injection transport layer.

Finally, Al is deposited in a thickness of 150 nm to form a negative electrode.

When a DC voltage of 10 V is applied to the organic electroluminescent device fabricated in the above manner, blue light emission having high color purity is obtained.

Example 13

The same procedures as in Example 11 are performed until the hole injection transport layer insolubilized by crosslinking the polymer 1 is formed.

Next, a poly(2-vinylnaphthalene) which has a weight average molecular weight of 1,200,000 and is used as a thickener in a ratio of 52 wt % on a solid basis, compound 31 which is used as an electron transport host material in a ratio of 52 wt % on a solid basis, the isomer component of the compound 3 having an Rf-value of 0.34 and obtained in Example 3 which is used as a blue light-emitting dopant material in a ratio of 5 wt % on a solid basis, and a compound represented by the compound 33 which is used as a hole transport material in a ratio of 10 wt % on a solid basis are mixed to prepare an ink of an anisole solution which has a total solid content ratio of 12 wt % and a viscosity of about 40 to 80 mPa·S.

This ink is applied to an anilox roll by roll coating, wherein the film is wound cylindrically around the roll, and transferred to a projection portion on a printing precursor plate of relief printing system, carried out roll printing on a glass substrate on which the electron block hole transport layer is formed, and then, the film is dried to form a light-emitting layer.

Next, on the light-emitting layer, the compound 31 and lithium are codeposited in a thickness of about 5 to 10 nm at a ratio of vapor deposition rate of 100:4 to form an electron injection transport layer.

Finally, Al is deposited in a thickness of 150 nm to form a negative electrode.

When a DC voltage of 10 V is applied to the organic electroluminescent device fabricated in the above manner, blue light emission having high color purity is obtained.

Example 14

A method for forming a light-emitting layer by the laser sublimation transfer method using a donor base material according to an embodiment of the present invention will be explained with reference to FIG. 13.

A display substrate 21 is manufactured in the same manner as in Example 11 before the electron block hole transport layer 4 is formed except that the positive electrodes 2 constituted of an ITO film are formed stripe-wise separately in three-color (blue, green, and red) light-emitting regions corresponding to a color display.

Next, when the donor base material which is used for the transfer of the blue light-emitting layer and manufactured in Example 7 is overlapped on an EL display substrate under vacuum to heat the backside of the donor base material corresponding to the light-emitting region by scan-applying a laser beam 22, compounds in the transfer layer 20 formed on the donor base material are sublimated, resulting in the formation of a light-emitting layer on the display substrate 21. In the case of transferring to the display substrate 21 larger than the donor base material, the donor substrate is overlaid on the display substrate to repeat the transfer operation while changing the position of the donor substrate.

Next, donor base materials which are used for the transfer of the green and red light emitting layer and manufactured in Examples 8 and 9 respectively are used one by one to carry out laser sublimation transfer to a part corresponding to each color emission region in the same manner as above to form green and red light-emitting layer lines.

Next, on the light-emitting layer, the compound 19 and Li oxine complex are codeposited in a thickness of 20 nm at a ratio of vapor deposition rate of 10:1 to form an electron injection transport layer.

Finally, LiF is deposited under vacuum in a thickness of 0.5 nm through a vapor deposition mask with a stripe-like hole in a direction perpendicular to the stripe line of ITO, and further, Al is deposited in a thickness of 150 nm to form a negative electrode.

When a DC voltage of about 10 V is applied across each ITO line and negative electrode line of the organic electroluminescent device manufactured in the above manner, EL emission is obtained from each light emitting layer (blue, green, and red) formed at the point of intersection between the positive electrode ITO line and negative line.

Example 15

The same procedures are carried out until the polymer 1 is used to form the electron block hole transport layer insoluble in toluene.

Next, the crosslinking type compound 21 is formulated in a xylene solution of the polymer 2 in a ratio of 10 wt % on a solid basis to produce ink, which is then applied to the electron block hole transport layer of the organic electroluminescent device substrate in a thickness of 60 nm by spin coating. A region corresponding to a light-emitting portion is exposed to 365 nm ultraviolet light emitted from a 4 W low-pressure mercury lamp through a filter by passing the light through a photomask for 60 sec, and the film is then rinsed with toluene to remove an unnecessary film and unreacted compound 21, followed by drying to thereby make a light-emitting layer insoluble in toluene.

The compound represented by the formulae (1) to (3) according to the present invention contains, as its skeleton, 9,10-diarylanthracene having high color purity of blue light emission.

Furthermore, because the compound represented by the formulae (1) to (3) according to the present invention contains a large and stiff substituent derived from a group of diphenyltriazine derivative on one or both of the ninth and tenth positions of the anthracene ring, the steric hindrance of the Polymer 2

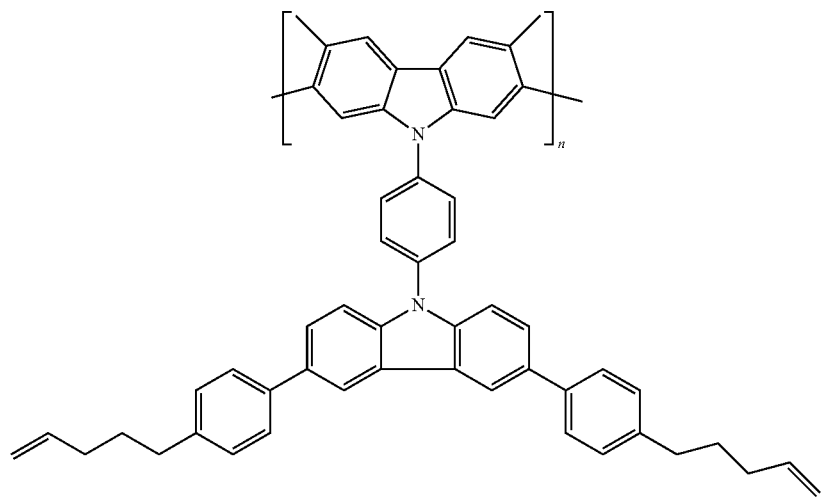

(n is an integer denoting the degree of polymerization)

Next, a toluene solution of the compound 19 was applied in a thickness of 10 nm by the spin coating method, an unnecessary organic film on the electrodes and the like is wiped off, and then the film is heated at 200° C. under vacuum for 30 min to dry it to make an electron injection transport layer.

Finally, LiF is vacuum-deposited in a thickness of 0.5 nm and Al is further deposited in a thickness of 150 nm to form a negative electrode.

When a DC voltage of about 10 V is applied to the organic electroluminescent device manufactured in the above manner, blue EL light emission is obtained.

Example 16

A method for fabricating an electroluminescent device provided with a liquid light-emitting layer according to an embodiment of the present invention will be explained.

A 10.5-μm-thick polyester film spacer is sandwiched between two 0.7-mm-thick non-alkali glass plates with a transparent electrode formed of an ITO film and the cell are bonded at the three sides. Orthodichlorobenzene in which 5 wt % of the compound 3 and 0.1 mol/L of $LiCF_3SO_3$ are dissolved is flowed into the cell from the remainder side. When a DC or AC voltage is applied across both electrodes, blue EL light emission is obtained.

The present invention was achieved to provide a light-emitting dopant for a light-emitting layer which is constituted of a fluorescent low-molecular weight material which can be dissolved in an organic solvent and can form film by applying it, and has a high Tg and high heat resistance, a host material for a light-emitting layer for a fluorescent or phosphorescent material, and a hole or electron carrier transport material.

substituent fulfills the expectation of the effect of limiting the deterioration based on the dimerization of anthracene rings due to close contact between anthracene rings, effect of inhibiting concentration quenching, and effect of inhibiting deterioration in color purity due to the generation of excimer emission of light having a long wavelength.

Further, the compound of the present invention can be utilized as a light-emitting material for a wet type electro-chemiluminescence device because a high luminous intensity can be obtained even if a high concentration solution is used.

Further, in the compound represented by the formulae (1) to (3) according to the present invention, the large and stiff substituent on one or both of the ninth and tenth positions of the anthracene ring cannot be freely rotated around the anthracene ring due to steric hindrance and there is therefore the case where a rotamer (atropisomer) exists. Moreover, even if the substituents at the ninth position and tenth position are the same, there is the case where a mixture of optical isomers is produced depending on the positions of substituents of $R_1$ to $R_8$. Because of this, it is considered that a film constituted of a mixture of these isomers is scarcely crystallized.

Further, since the compound represented by the formulae (1) to (3) according to the present invention contains a large and stiff substituent on one or both of the ninth position and tenth position of the anthracene ring, the whole molecule is steric and stiff and therefore, a compound expected to have a Tg higher than 200° C. or more can be easily synthesized, producing the effect of improving the heat resistance of an organic electroluminescen device.

Moreover, two neighboring substituents substitute the positions of $R_9$ to $R_{12}$ of the compound represented by the formula (1) or $R_9$ to $R_{16}$ of the compound represented by the formula (2), for example, the substituents of $R_{10}$ and $R_{11}$ can be combined with each other to form a ring, and a stiffer molecule can be obtained in the case of forming a naphthalene ring as a condensed ring.

Blue light fluorescence originated from an anthracene ring is obtained from the compound represented by the formulae (1) to (3) according to the present invention when adjacent groups of $R_1$ to $R_8$ on the anthracene ring are not combined with each other to form no condensed ring. Further, when adjacent groups of $R_1$ to $R_8$ are combined with each other to form a condensed ring, for example, a benzoanthracene ring or a dibenzoanthracene ring, the wavelength of a light emission spectrum is made longer, making it possible to obtain green or red color emission. Because of this, the compound of the present invention is useful as a light-emitting material for a full color display.

The effect of making the emission wavelength longer can be obtained also in the case of combining a monovalent group derived from an aryl group or heteroaryl group which can conjugate with an anthracene ring as the substituent for $R_2$, $R_3$, $R_6$, $R_7$ and the like on the anthracene ring, enabling the emission color to be controlled.

Further, the compound represented by the formulae (1) to (3) according to the present invention has electron transportability because it contains a triazine ring increasing electron affinity on one or both of the ninth and tenth position of the anthracene ring. The compound of the present invention which is further substituted with a heteroaryl group such as an oxadiazole ring, thiadiazole ring, pyrimidine ring, pyrazine ring, triazine ring, and benzoimidazole ring containing nitrogen is more increased in electron affinity and is therefore useful as an electron transport material.

As the substituent other than hydrogen on the compound represented by the formulae (1) to (3) according to the present invention, an appropriate one may be selected from the group consisting of deuterium, fluorine, cyano group, trifluoromethyl group, trimethylsilyl group, alkyl group, alkoxy group and polyoxyalkylene group having 15 or less carbon atoms, substituted or unsubstituted aryl group and heteroaryl group, and crosslinkable substituent.

The energy level of the compound can be controlled by substituting the substituent contained in the compound with a strong electron attractive group selected from fluorine, a trifluoromethyl group, and cyano group. At this time, the anthracene ring in the center of the molecule may be substituted at the positions symmetric thereto or each aromatic ring may be substituted at the positions symmetric to the center thereof by an even number of groups to offset a dipole moment to thereby increase the Ip and electron affinity (hereinafter abbreviated as "Ea") of the compound without any increase in the polarizability of the molecule, which increase leads to reduction in hole or electron carrier mobility.

Examples of the symmetric substitution include compounds substituted at a combination of $R_2$ and $R_6$ positions, a combination of $R_3$ and $R_7$ positions, a combination of four positions of $R_2$, $R_3$, $R_6$, and $R_7$ on the anthracene ring in the formulae (1) to (3), or at a combination of $R_{11}$ and $R_{15}$ positions on the compound represented by the formula (2).

Further, $R_1$ to $R_8$ on the anthracene ring in the formulae (1) to (3) may be substituted with deuterium to form a C-D bond. In this case, though there is the case where vibration from heat is more suppressed and heat inactivation in an excitated state is more suppressed, so that the intensity of fluorescence is more increased than in the case of the C—H bond, there is, on the contrary, the case where intersystem crossing to the triplet is promoted by the substitution with a heavy atom, resulting in deteriorated fluorescent intensity.

One or more crosslinkable substituents may be added as the substituent. A compound to which a crosslinkable group is added according to the present invention is doped as a light-emitting material in the host material which can be crosslinked by light or heat. When the compound is irradiated with light or a laser through a photomask, it is crosslinked together with the host material to form an insoluble film. A multicolor fine light emission array pattern can be obtained by repeating exposure and development for each color and can be utilized for the manufacture of a full-color display.

An appropriate selection of the substituent in the compound of the present invention can bring about high solubility in an aromatic organic solvent, with the result that a compound can be synthesized which is soluble in an organic solvent used in printing such as toluene, xylene, anisole, or tetralin in a concentration higher than a concentration of about 1 to 3 wt % which is usually used in coating or printing ink solutions.

Further, the compound of the present invention may be mixed with a high-molecular weight compound having a high degree polymerization and high viscosity, which is then dissolved in an organic solvent to form ink, to thereby adjust the solution to a viscosity adaptable to the printing method.

Because of this, the compound of the present invention can be applied to the selective vapor deposition method superior in mass-productivity, such as the relief-printing method, screen printing method, inkjet printing method, and continuous nozzle printing method and the coating method such as slit coating, capillary coating, or roll coating, and is also effective to reduce the production cost of an organic electroluminescent panel having a large size.

Moreover, the compound of the present invention can be utilized for the transfer method useful for the manufacture of a large-size organic electroluminescent panel. For example, ink comprising a polymer binder, such as, a polystylene or polyvinylnaphthalene which maintains the shape of a film during transfer or peeling and imparts heat transferability, a low-molecular hole transport material or electron transport material and a light-emitting material constituted of the compound of the present invention is applied and printed to form a film as a donor base material, which is interposed on a display substrate having a pixel drive circuit. The resulting display substrate is heated by means of, for example, a heat bar or laser beam to thermally transfer the film, whereby a light-emitting layer can be formed.

Moreover, ink constituted only of a low-molecular weight material containing the compound of the present invention is applied and printed to form a donor base material, which is then interposed on a display substrate having a pixel drive circuit for sublimation-transfer by sequentially moving the substrate, whereby a light-emitting layer can be formed on even a display substrate having a large size.

When the compound of the present invention is used for a donor base material used in sublimation transfer and formed by coating film formation, it is preferable to use a compound having a molecular weight of about 650 to 1300. A material in a film having a molecular weight less than 650 sometimes starts sublimating at a temperature of about 200° C. in vacuum drying. On the other hand, when the molecular weight exceeds 1300, the sublimation temperature becomes about 500° C., causing easy decomposition and denaturing of the organic compound.

When two or more compounds are blended to form a donor base material used in sublimation transfer, it is desirable to select and apply compounds having molecular weights close to each other such that these compounds have the same sublimation transfer temperature in order to obtain a uniform film composition. A dopant material having a molecular weight within ±10% and preferably ±5% of that of the host material is blended and applied to obtain a sublimation film having high compositional uniformity.

Further, in the case of forming a film having a graded composition in the direction of the thickness of the film, compounds differing in molecular weight may be blended upon use. If, for example, a low-molecular hole transport material having a molecular weight smaller by 10% or more than the low-molecular host material or light-emitting dopant material in the light-emitting layer is formulated, the concentration of the low-molecular weight hole transport material in the light-emitting layer on the electron block hole transport layer side can be raised and the concentration of the hole transport material in the light-emitting layer on the negative electrode side can be dropped, thereby enabling reduction in the resistance of the film to improve luminous efficiency.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A compound represented by a formula (2) below:

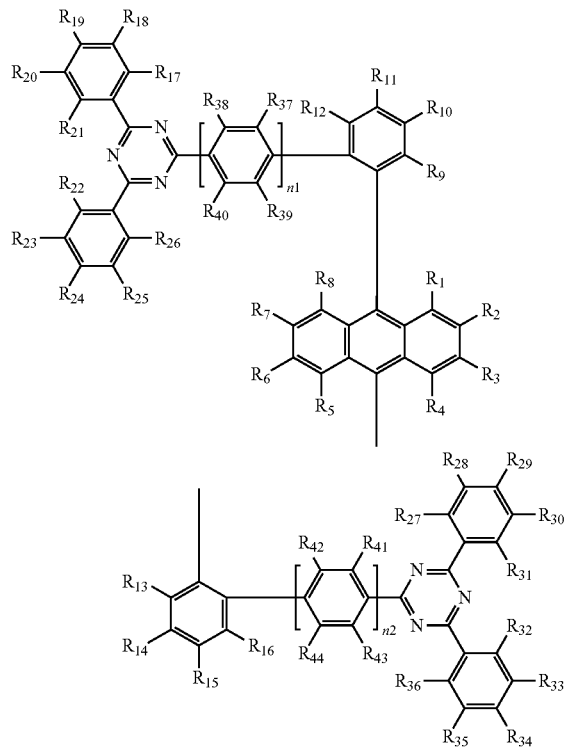

Formula (2)

wherein
each of $R_1$ to $R_{44}$ is independently selected from a group consisting of hydrogen, deuterium, fluorine, a cyano group, a trifluoromethyl group, a trimethylsilyl group, an alkyl group, an alkoxy group and a polyoxyalkylene group having 15 or less carbon atoms, a substituted or unsubstituted aryl group and heteroaryl group having 15 or less carbon atoms, and a crosslinkable substituent having 15 or less carbon atoms, and
each of n1 and n2 independently represents an integer of 0 or 1.

2. A compound represented by a formula (8) below:

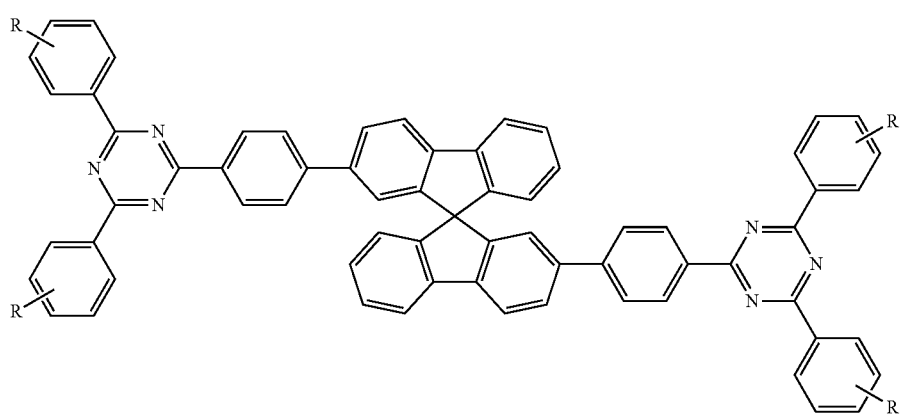

formula (8)

wherein R represents an alkyl group having 1 to 4 carbon atoms.

3. A solid or liquid composition, comprising:
a compound represented by a formula (9)

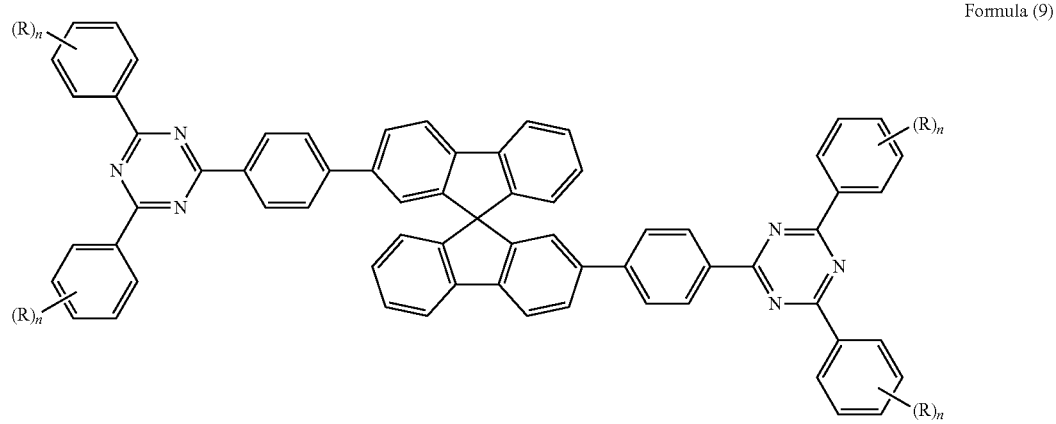

Formula (9)

wherein R represents an alkyl group and n represents an integer from 0 to 3 which indicates the number of substituents; and at least one compound represented by a formula (1) below:

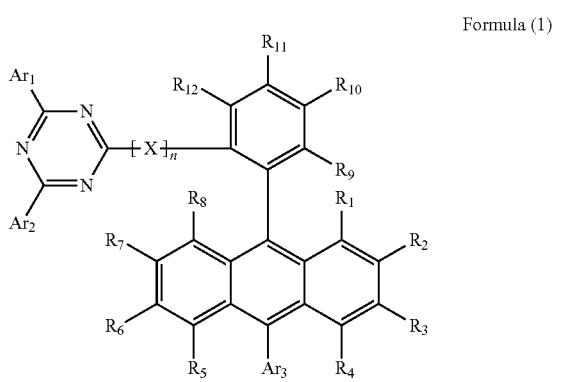

Formula (1)

wherein

X represents a residue derived from an aryl ring or a heteroaryl ring which may have one or more substituents, or a single bond, $Ar_1$ and $Ar_2$ respectively represent an unsubstituted or substituted phenyl group or heteroaryl group, $Ar_3$ represents a group having 60 or less carbon atoms, the group represents a structure in which six or less aryl or heteroaryl groups which may have one or more substituents are conjugatedly linked, or the same group as a substituent at the ninth or tenth position on the anthracene ring, the substituents on X and $Ar_1$ to $Ar_3$ and $R_1$ to $R_{12}$ are independently selected from a group consisting of hydrogen, deuterium, fluorine, a cyano group, a trifluoromethyl group, a trimethylsilyl group, an alkyl group, an alkoxy group and a polyoxyalkylene group having 15 or less carbon atoms, a substituted or unsubstituted aryl group and heteroaryl group having 15 or less carbon atoms, and a crosslinkable substituent having 15 or less carbon atoms, provided that $R_1$ to $R_{12}$ may have a structure in which adjacent substituents may be bonded to each other to thereby form a ring, and n represents an integer of 0 or 1.

4. An ink composition comprising at least one of the compounds according to claim 1 in a medium which is a liquid at room temperature.

5. An ink composition comprising at least one of the compounds according to claim 2 in a medium which is a liquid at room temperature.

6. A solid or liquid composition, comprising:
a compound represented by a formula (9), and
at least one of the compounds according to claim 1:

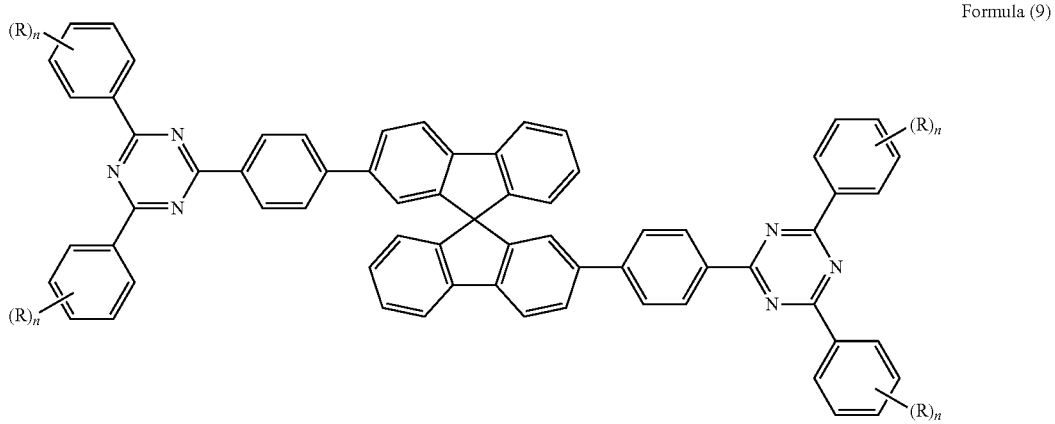

Formula (9)

wherein R represents an alkyl group and n represents an integer from 0 to 3 which indicates the number of substituents.

7. A light-emitting device comprising a light-emitting layer containing a light-emitting material as at least one layer between electrodes facing each other or between a positive electrode and a negative electrode, wherein the at least one layer between electrodes facing each other or between a positive electrode and a negative electrode contains the compound according claim 1.

8. A light-emitting device comprising a light-emitting layer containing a light-emitting material as at least one layer between electrodes facing each other or between a positive electrode and a negative electrode, wherein the at least one layer between electrodes facing each other or between a positive electrode and a negative electrode contains the compound according claim 2.

9. A solid or liquid composition, comprising:
a compound represented by a formula (9), and at least one of the compounds according to claim 2:

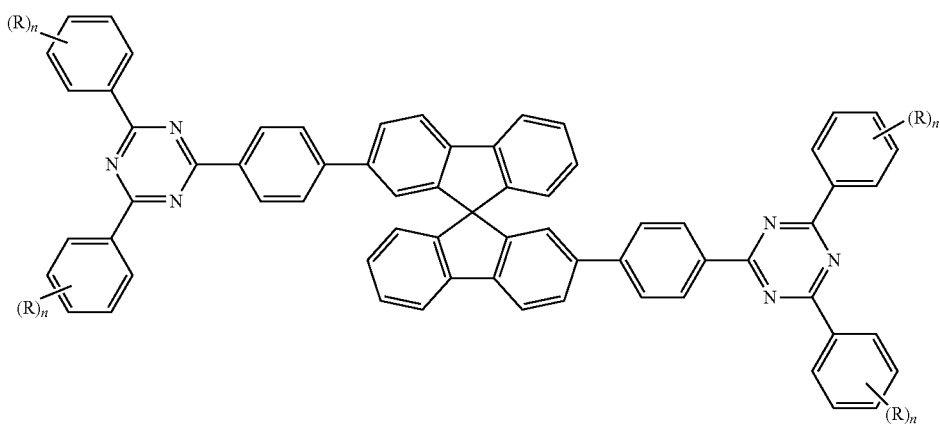

Formula (9)

wherein R represents an alkyl group and n represents an integer from 0 to 3 which indicates the number of substituents.

* * * * *

UNITED STATES PATENT AND TRADEMARK OFFICE
CERTIFICATE OF CORRECTION

PATENT NO. : 8,475,940 B2  
APPLICATION NO. : 13/495698  
DATED : July 2, 2013  
INVENTOR(S) : Yuichi Ito et al.

Page 1 of 1

It is certified that error appears in the above-identified patent and that said Letters Patent is hereby corrected as shown below:

Title Page 2 Col. 2 (Other Publications), Line 30, Delete "[9H-fluorenet]" and insert
-- [9H-fluorene] --, therefor.

In the Claims

In Col. 97, Line 45, In Claim 3, delete "moresubstituents," and insert -- more substituents, --, therefor.

In Col. 99, Line 10, In Claim 7, delete "according claim" and insert -- according to claim --, therefor.

In Col. 100, Line 7, In Claim 8, delete "according claim" and insert -- according to claim --, therefor.

Signed and Sealed this  
Fifth Day of November, 2013

Teresa Stanek Rea  
*Deputy Director of the United States Patent and Trademark Office*